United States Patent
Noon et al.

(10) Patent No.: US 11,678,919 B2
(45) Date of Patent: Jun. 20, 2023

(54) BONE DISTRACTION SYSTEM

(71) Applicant: DePuy Synthes Products, Inc., Raynham, MA (US)

(72) Inventors: John M. Noon, Swarthmore, PA (US); Joel Patrick Bales, Parkesburg, PA (US); Tushar Savaliya, Dumont, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 213 days.

(21) Appl. No.: 16/878,864

(22) Filed: May 20, 2020

(65) Prior Publication Data
US 2020/0281636 A1 Sep. 10, 2020

Related U.S. Application Data

(63) Continuation of application No. 14/668,443, filed on Mar. 25, 2015, now Pat. No. 10,695,112.

(60) Provisional application No. 62/132,113, filed on Mar. 12, 2015, provisional application No. 61/971,782, filed on Mar. 28, 2014.

(51) Int. Cl.
| | |
|---|---|
| *A61B 17/80* | (2006.01) |
| *A61B 17/66* | (2006.01) |
| *A61B 17/88* | (2006.01) |
| *A61B 90/00* | (2016.01) |

(52) U.S. Cl.
CPC .......... *A61B 17/8071* (2013.01); *A61B 17/66* (2013.01); *A61B 17/8009* (2013.01); *A61B 17/8875* (2013.01); *A61B 2090/031* (2016.02)

(58) Field of Classification Search
CPC ......... A61B 17/66–666; A61B 17/8004–8023; A61B 17/8071
See application file for complete search history.

(56) References Cited

U.S. PATENT DOCUMENTS

| | | | | |
|---|---|---|---|---|
| 5,704,938 A | * | 1/1998 | Staehlin | A61B 17/7216 606/86 R |
| 5,776,155 A | * | 7/1998 | Beaupre | G10K 11/24 606/169 |
| 6,033,412 A | * | 3/2000 | Losken | A61B 17/7216 606/57 |

(Continued)

FOREIGN PATENT DOCUMENTS

| | | |
|---|---|---|
| WO | 01/78612 A1 | 10/2001 |
| WO | 2006/023870 A2 | 3/2006 |
| WO | 2011/038209 A2 | 3/2011 |

OTHER PUBLICATIONS

ECA Medical Instruments, Trusted Surgical Solutions, www.ecamedical.com/productstechnology/orthopaedic-spine-instruments-procedural-kits-cranio-maxillofacial-cmf/; accessed and copied from website Jun. 12, 2015; 4 pages.

*Primary Examiner* — Eduardo C Robert
*Assistant Examiner* — Steven J Cotroneo
(74) *Attorney, Agent, or Firm* — BakerHostetler

(57) ABSTRACT

Instrumentation and methods are provided for orthopedic surgery, including bone distraction. The application describes a bone distraction system that can be used to both distract and retract, or increase and decrease, a gap between first and second bone segments. The instrumentation can include any one of, or any combination of, a distractor, a ratchet, a first footplate, a second footplate, a first torque application instrument, and a second torque application instrument.

23 Claims, 38 Drawing Sheets

(56) References Cited

U.S. PATENT DOCUMENTS

| | | | |
|---|---|---|---|
| 6,277,124 B1* | 8/2001 | Haag | A61B 17/663 |
| | | | 606/57 |
| 8,449,543 B2* | 5/2013 | Pool | A61B 17/7216 |
| | | | 606/62 |
| 8,574,273 B2 | 11/2013 | Russell et al. | |
| 9,782,202 B2* | 10/2017 | Knoepfle | A61B 17/663 |
| 10,166,053 B2* | 1/2019 | Kubis | A61B 17/663 |
| 2005/0021034 A1* | 1/2005 | Cohen | A61B 17/8019 |
| | | | 606/71 |
| 2005/0148905 A1* | 7/2005 | Frazee | A61B 17/8875 |
| | | | 601/2 |
| 2006/0058798 A1* | 3/2006 | Roman | A61B 17/66 |
| | | | 606/71 |
| 2010/0076444 A1* | 3/2010 | Staehler | A61B 17/8009 |
| | | | 606/90 |
| 2011/0092295 A1* | 4/2011 | Wernz | B25B 23/1427 |
| | | | 464/37 |
| 2012/0277749 A1* | 11/2012 | Mootien | A61B 17/8875 |
| | | | 606/70 |
| 2017/0156813 A1* | 6/2017 | Cutler | B25B 23/1427 |

* cited by examiner

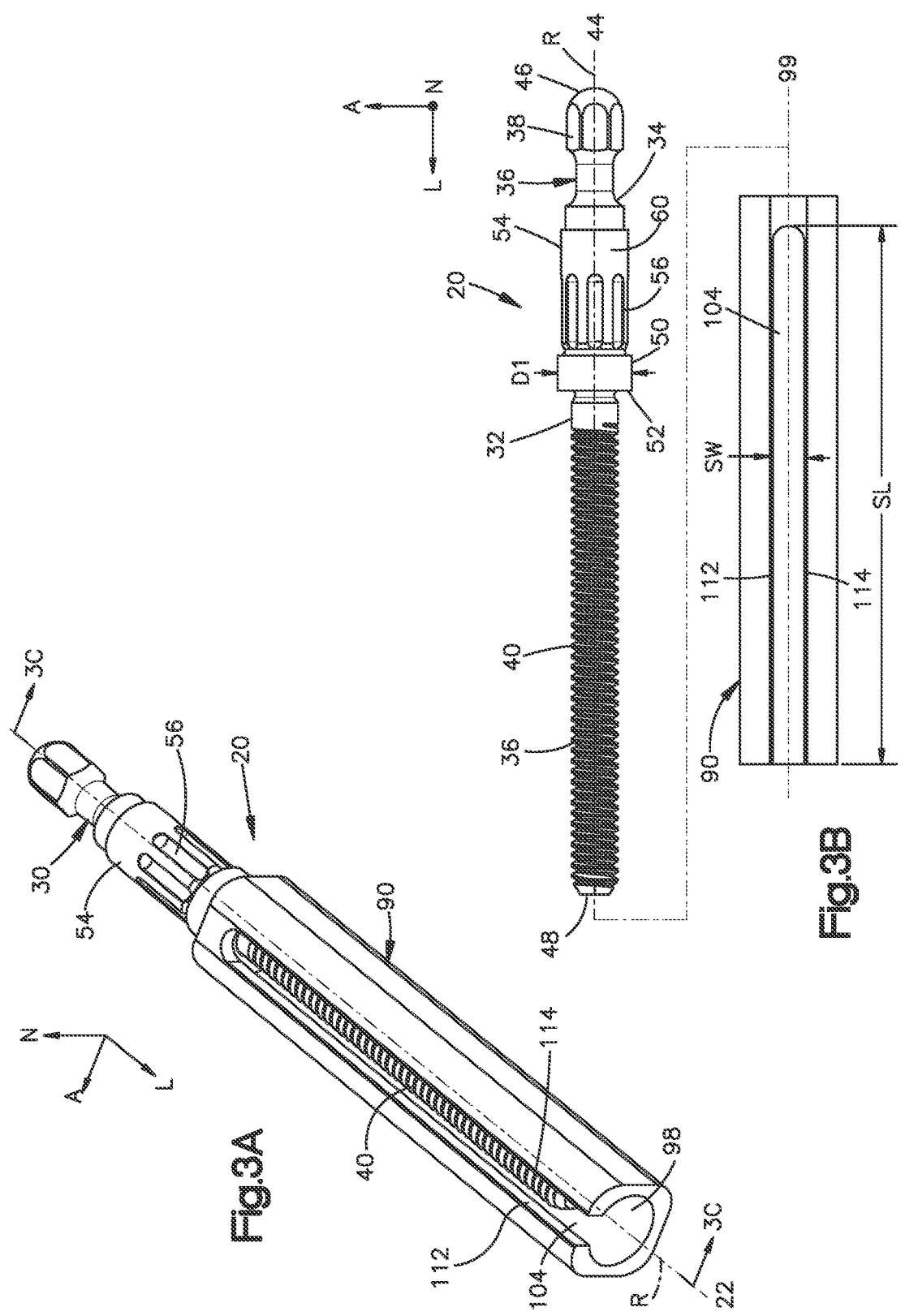

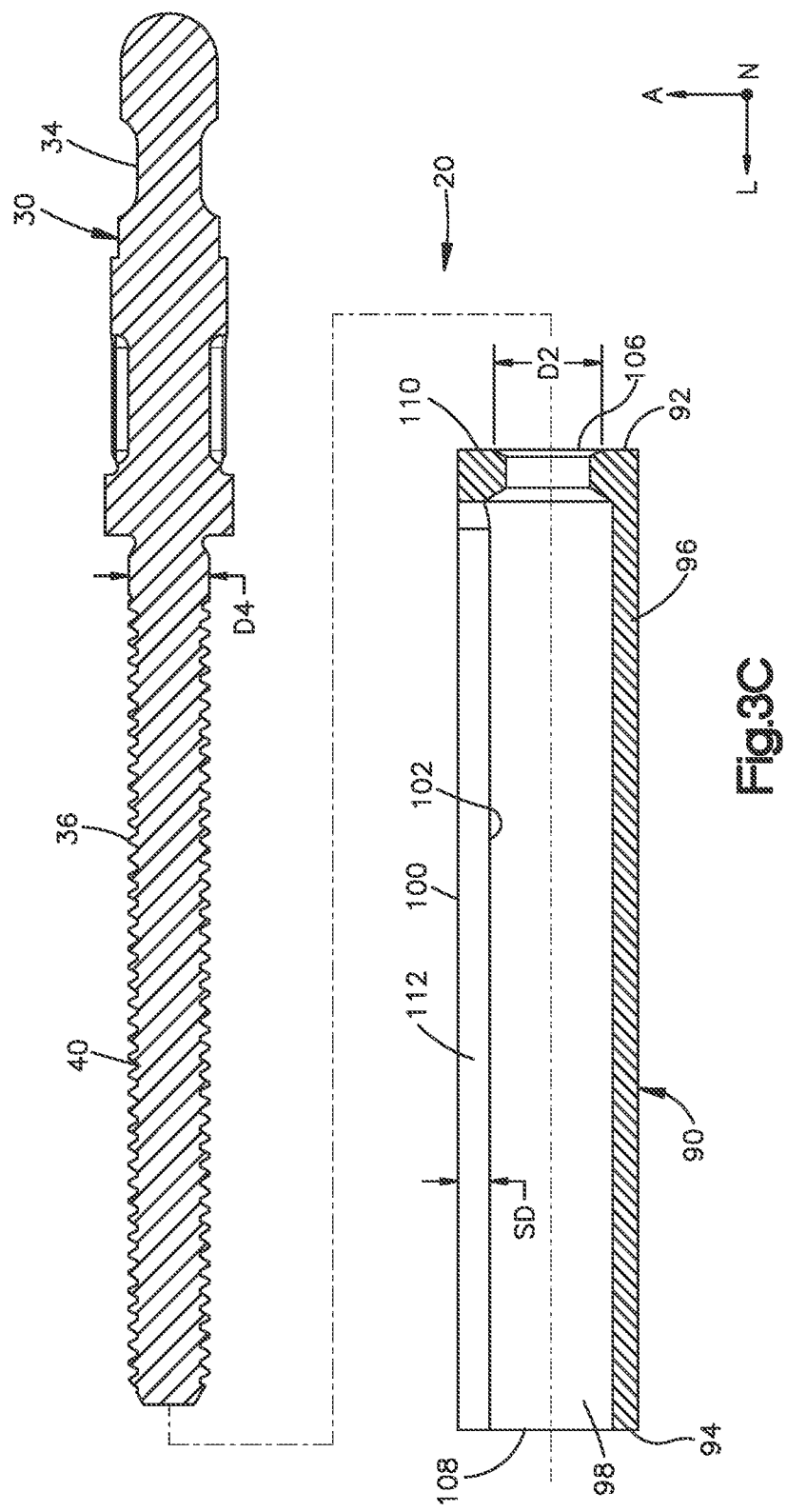

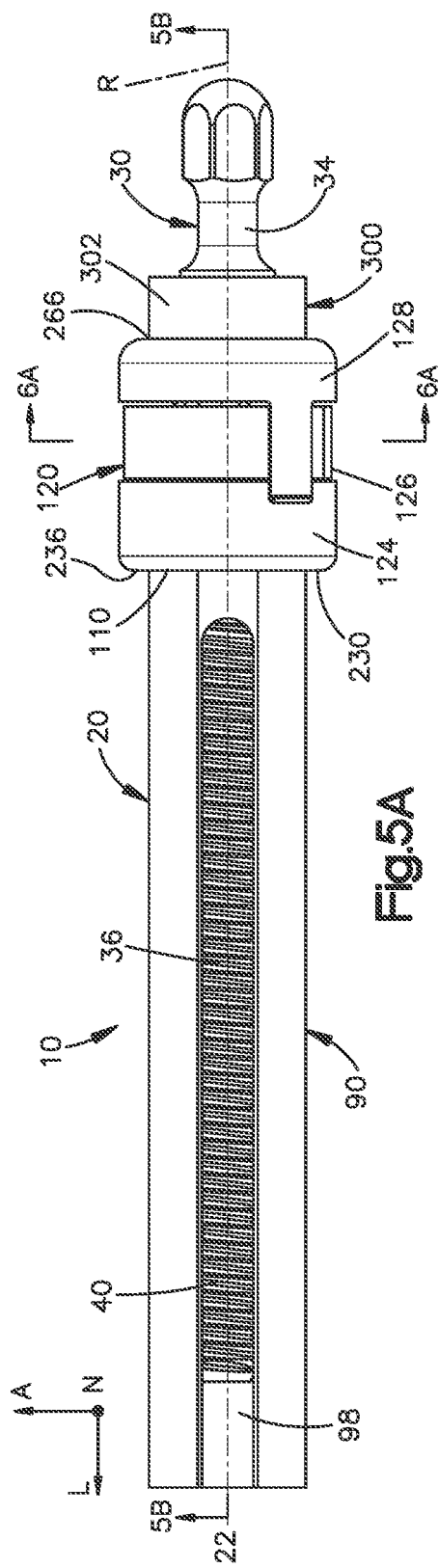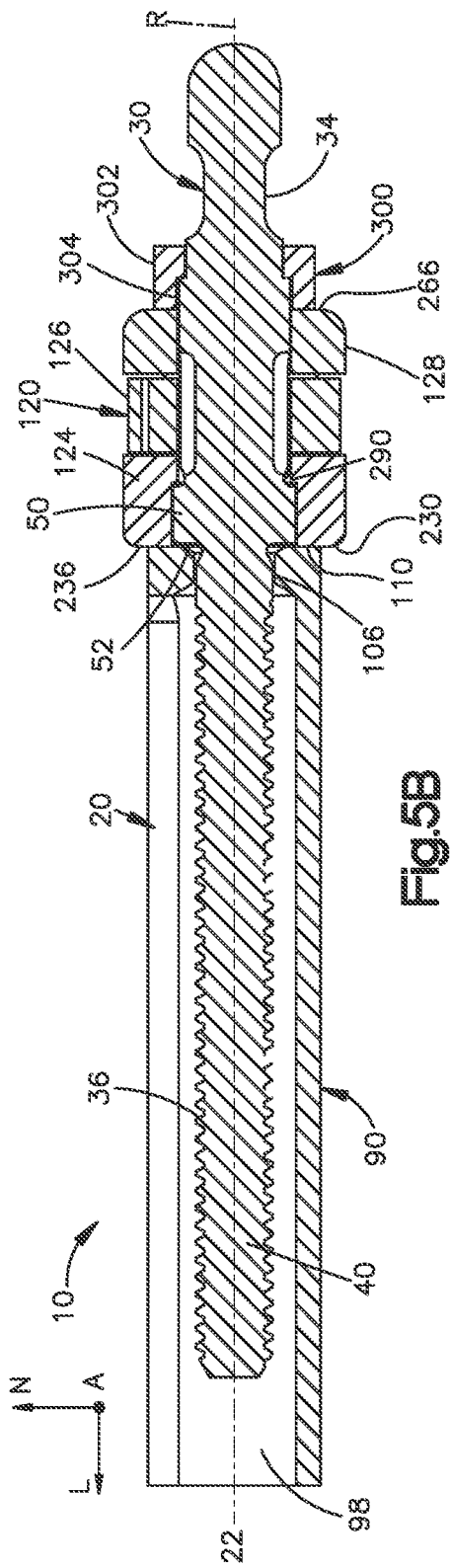

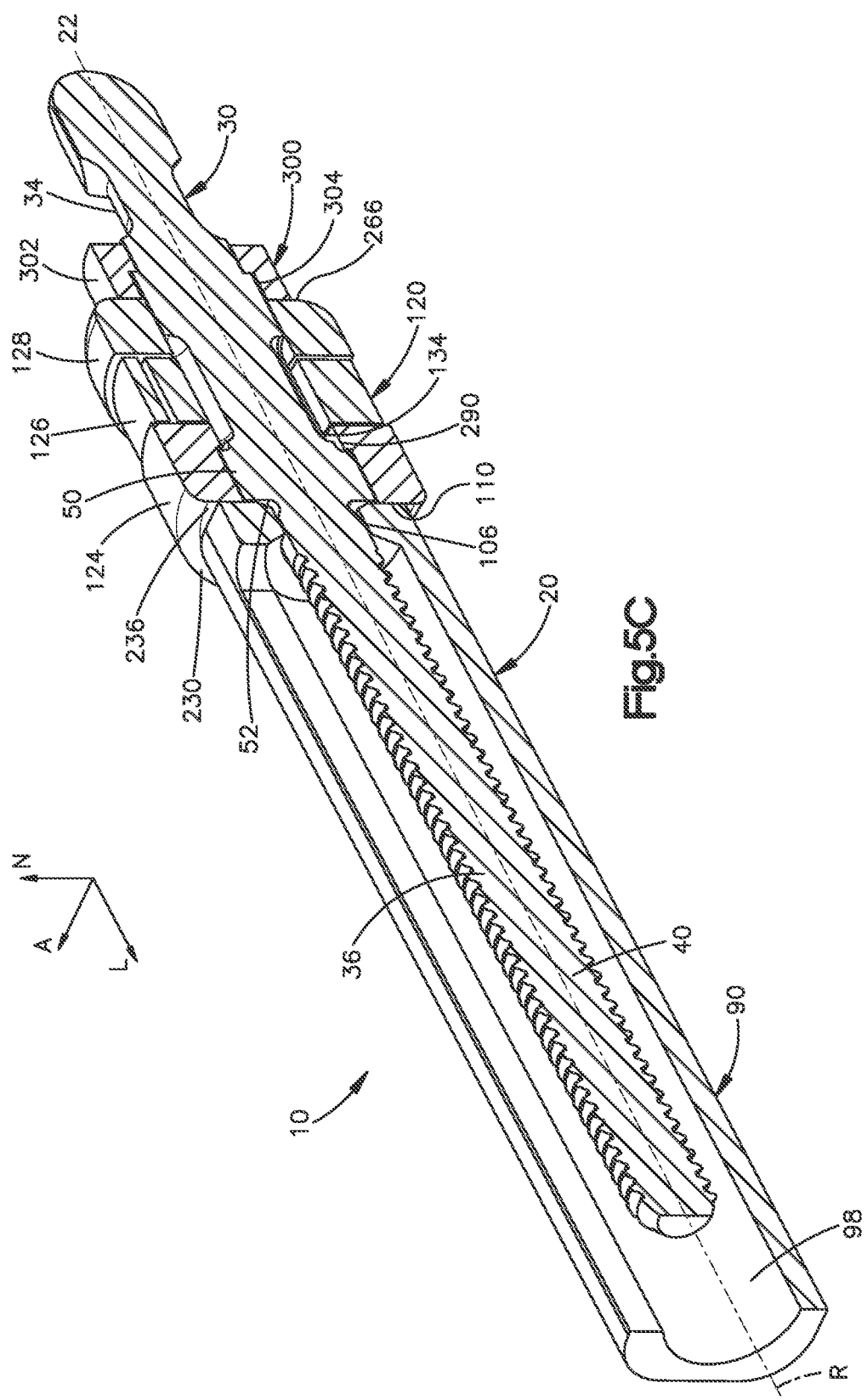

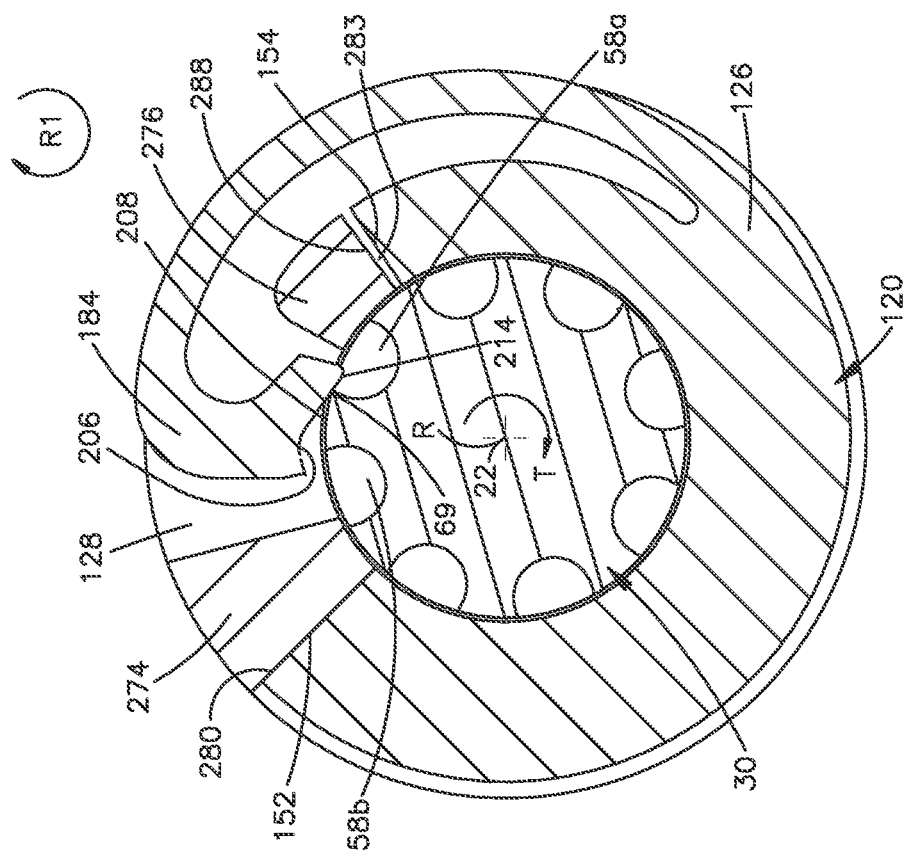
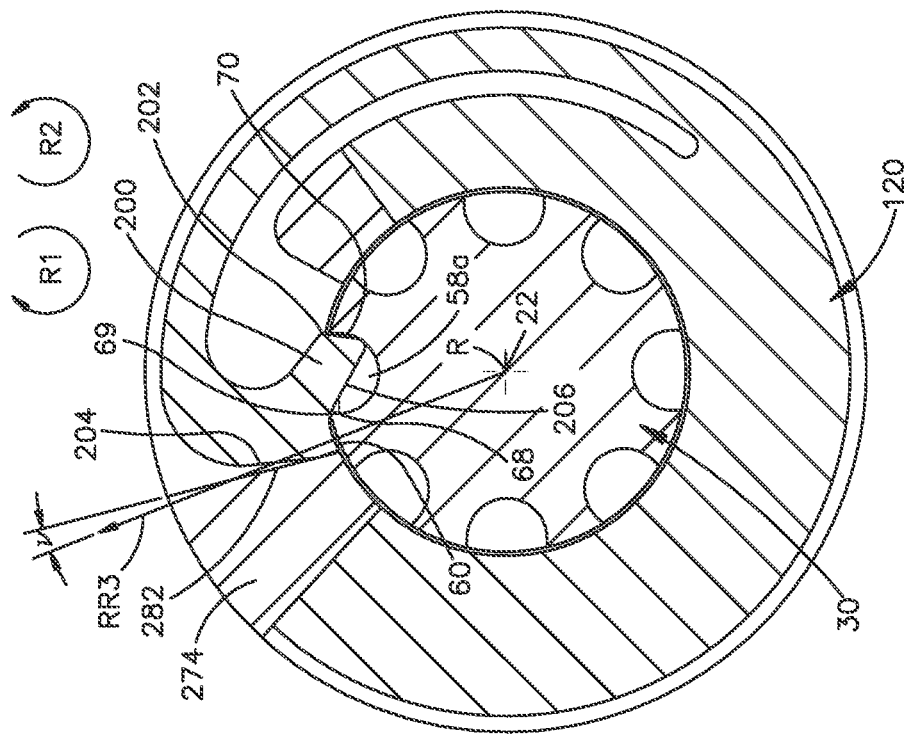

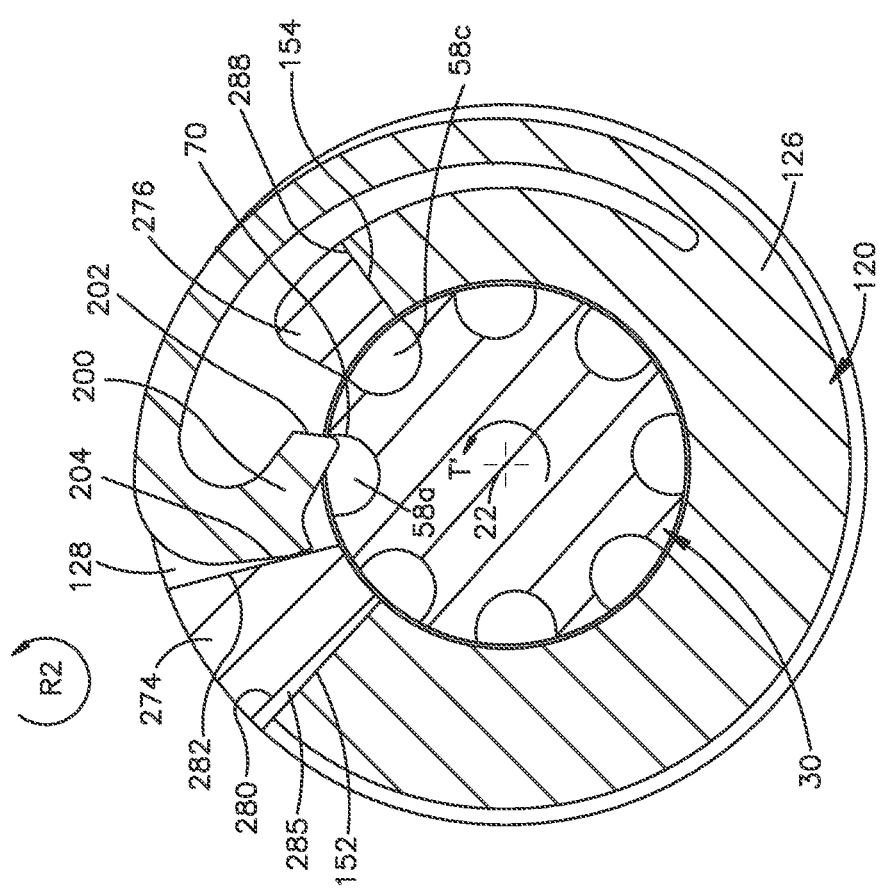

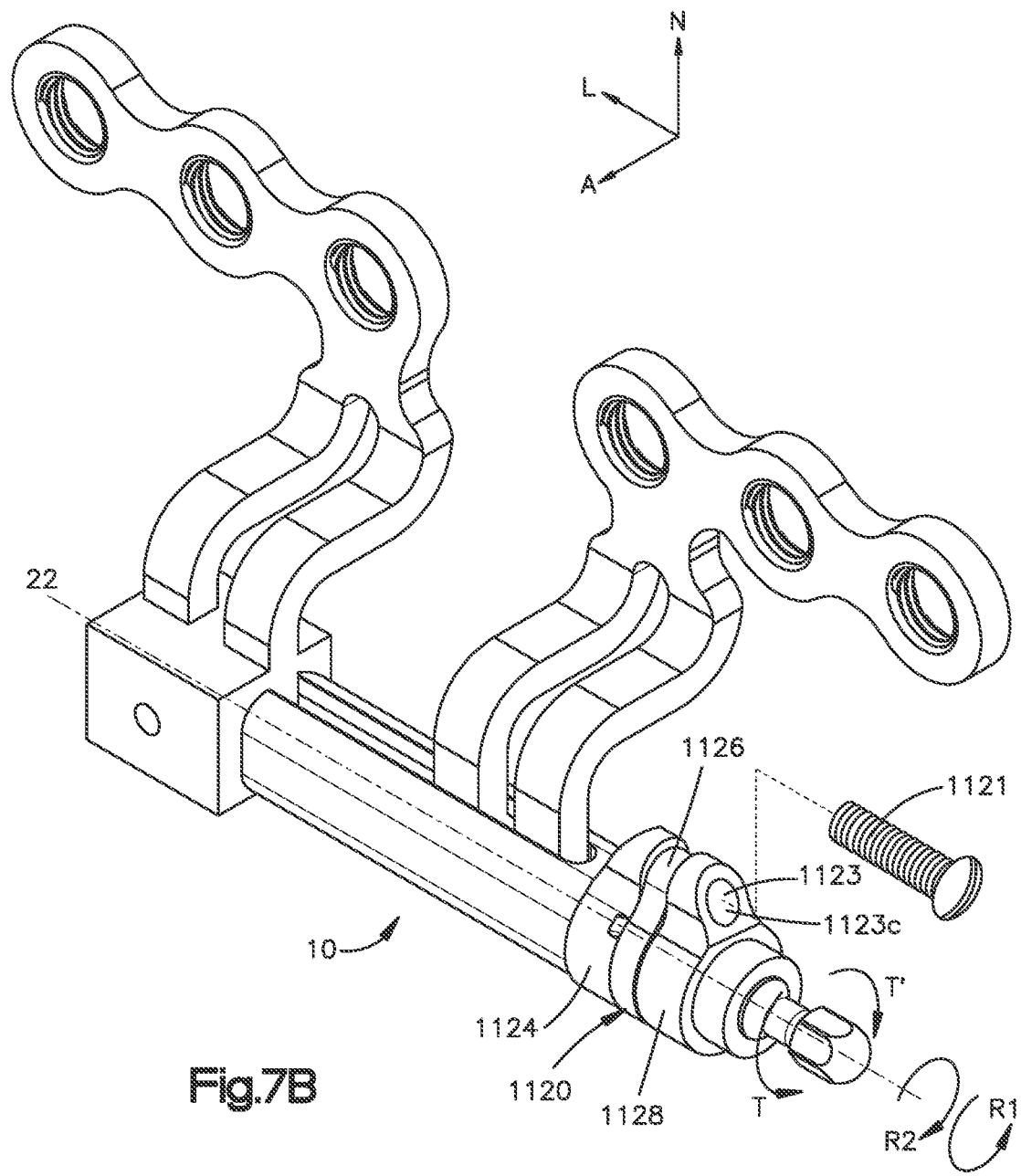

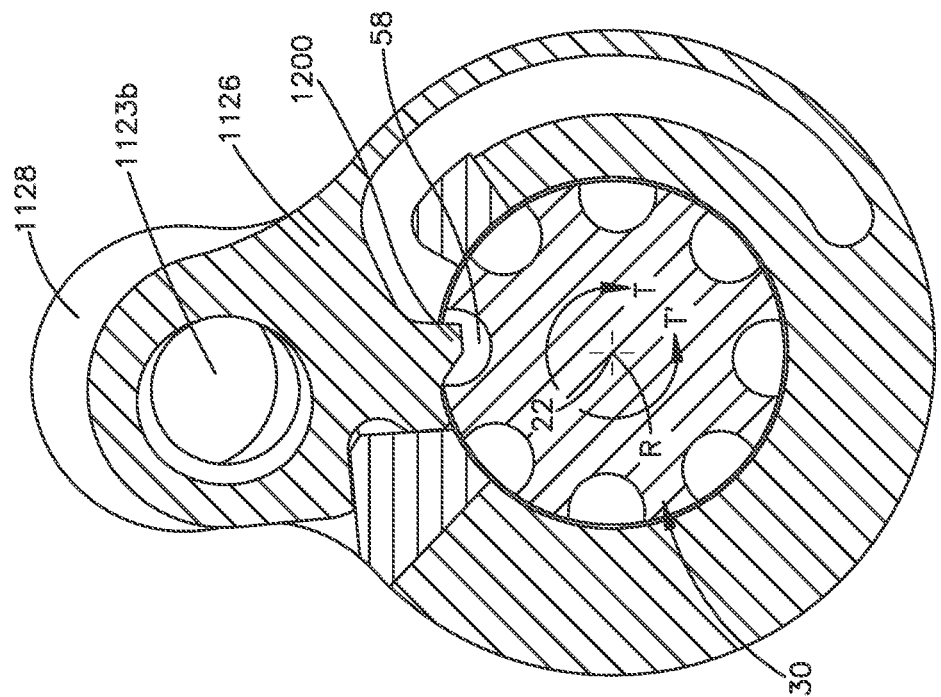
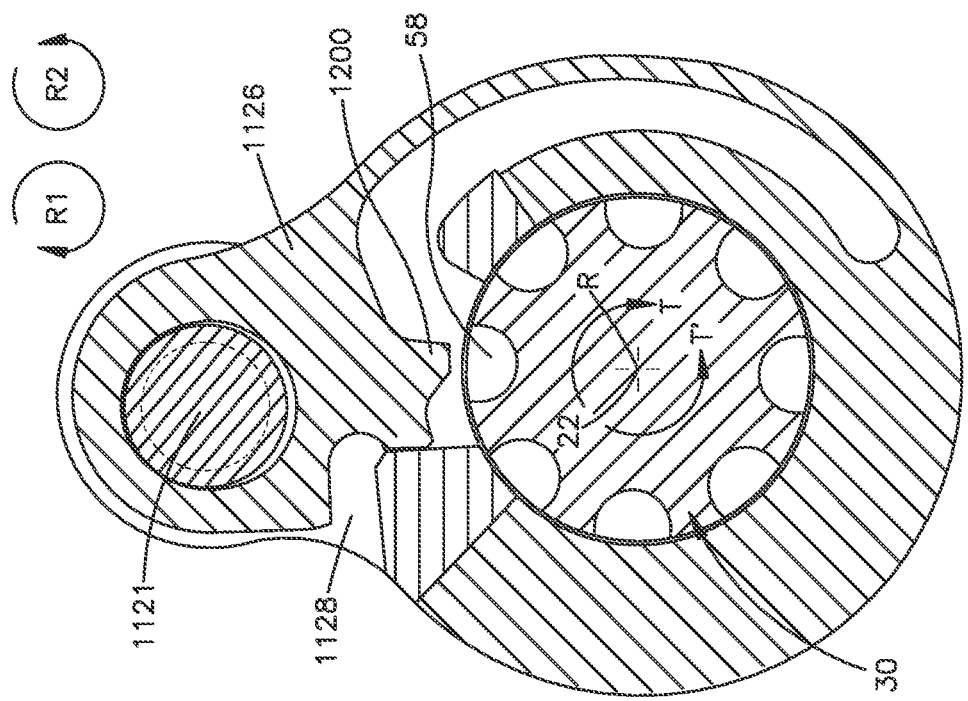

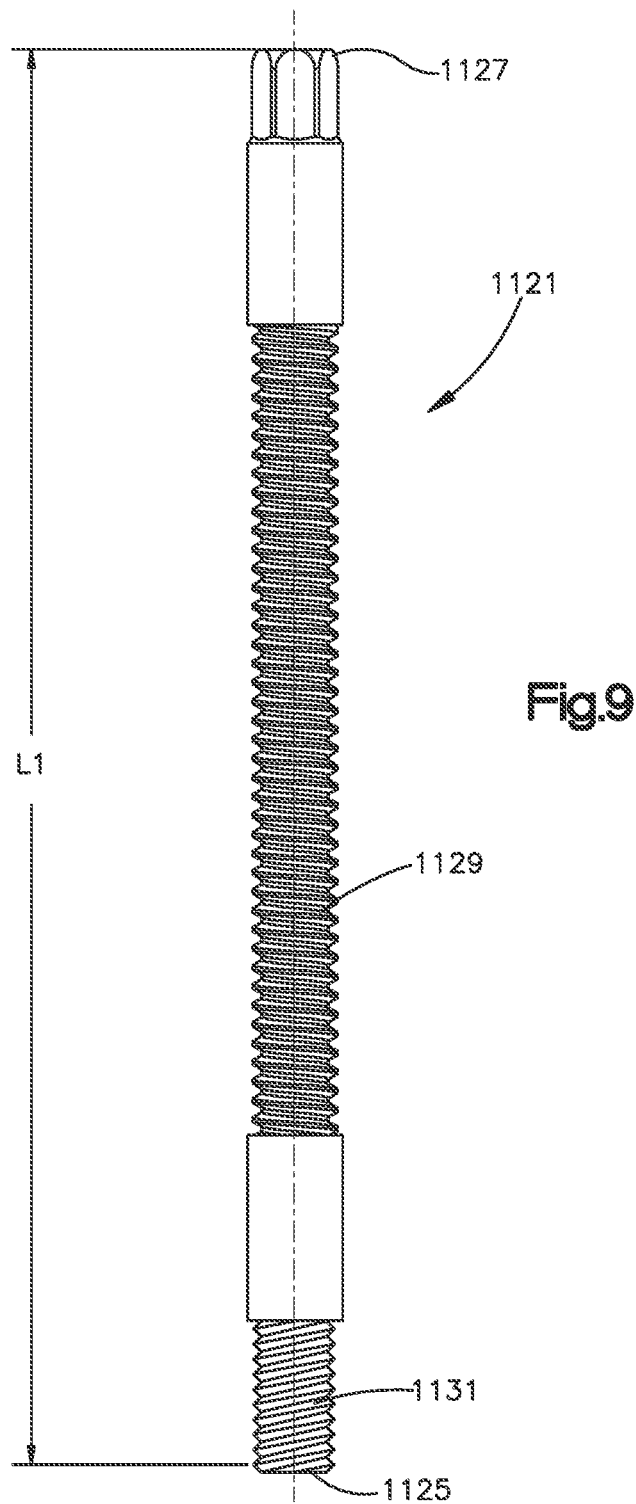

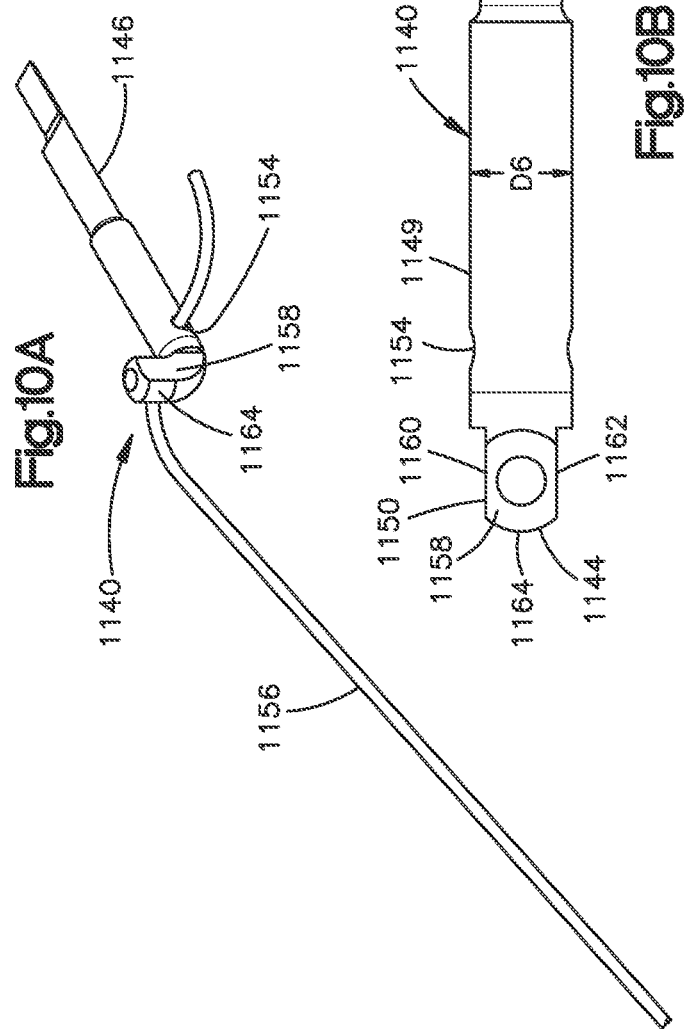
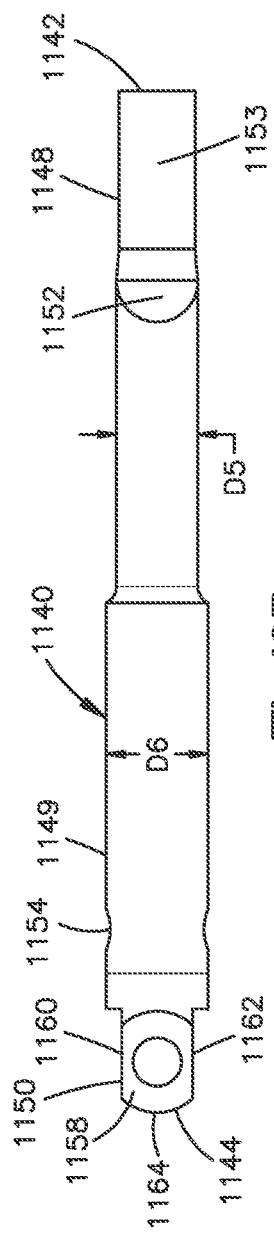
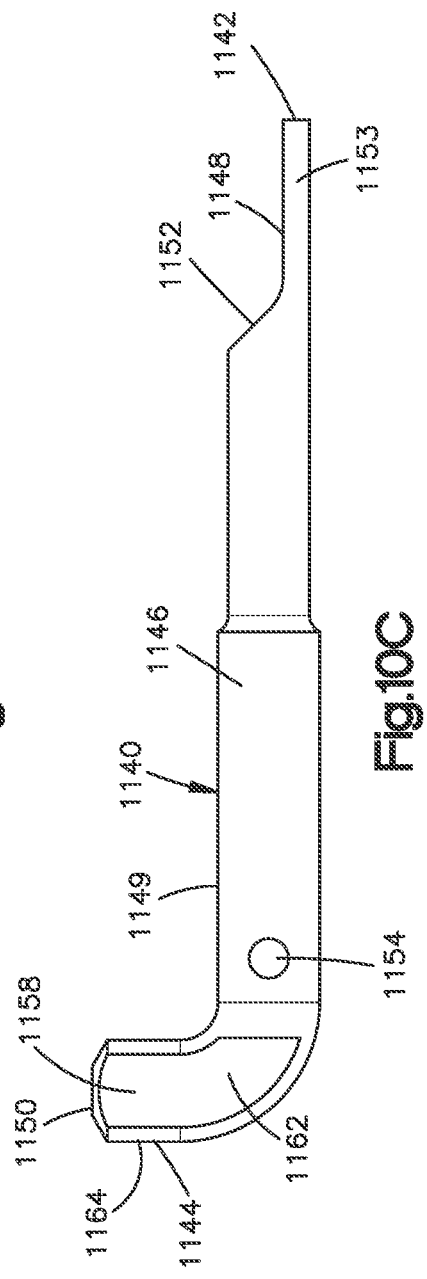
Fig.10A
Fig.10B
Fig.10C

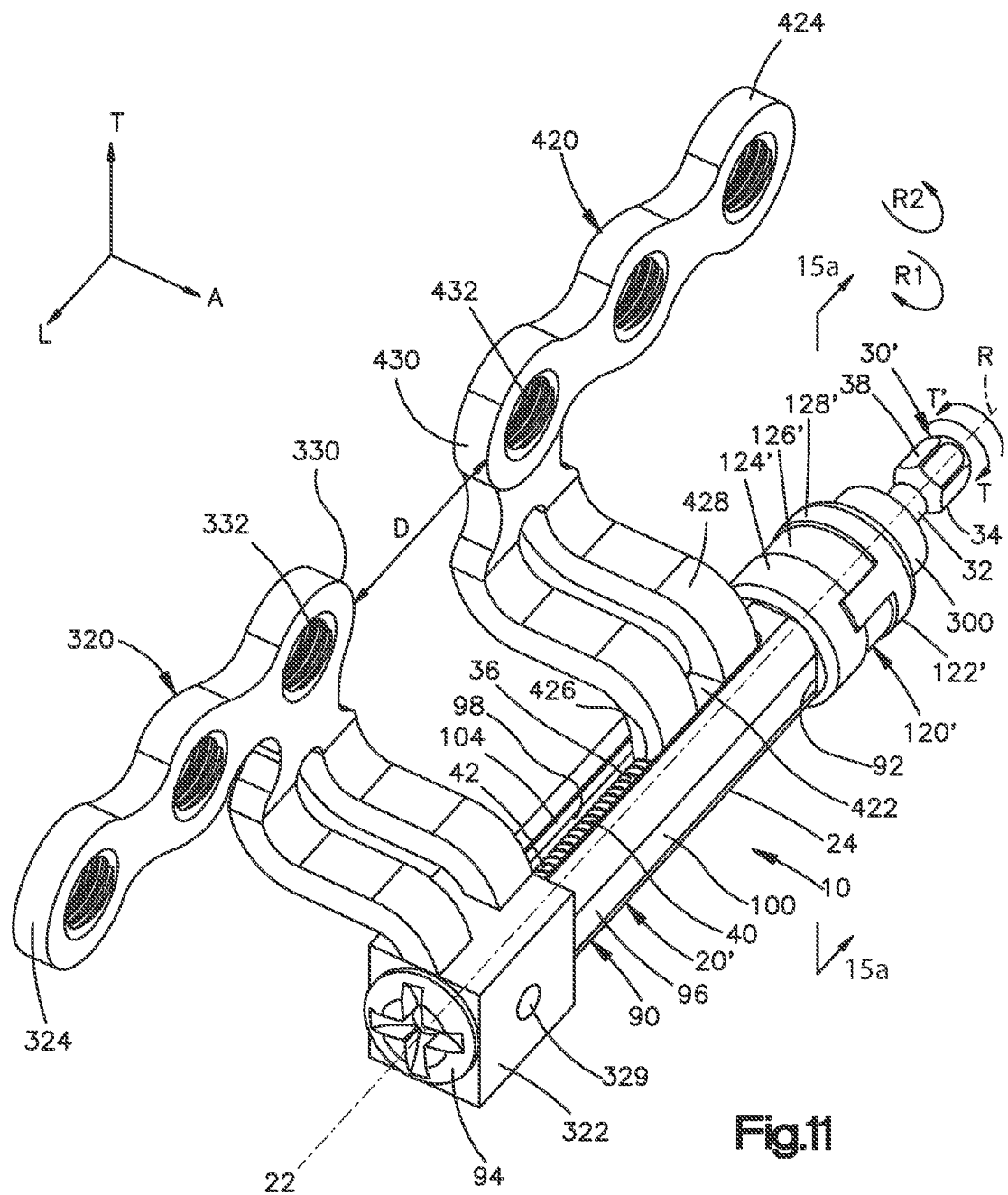

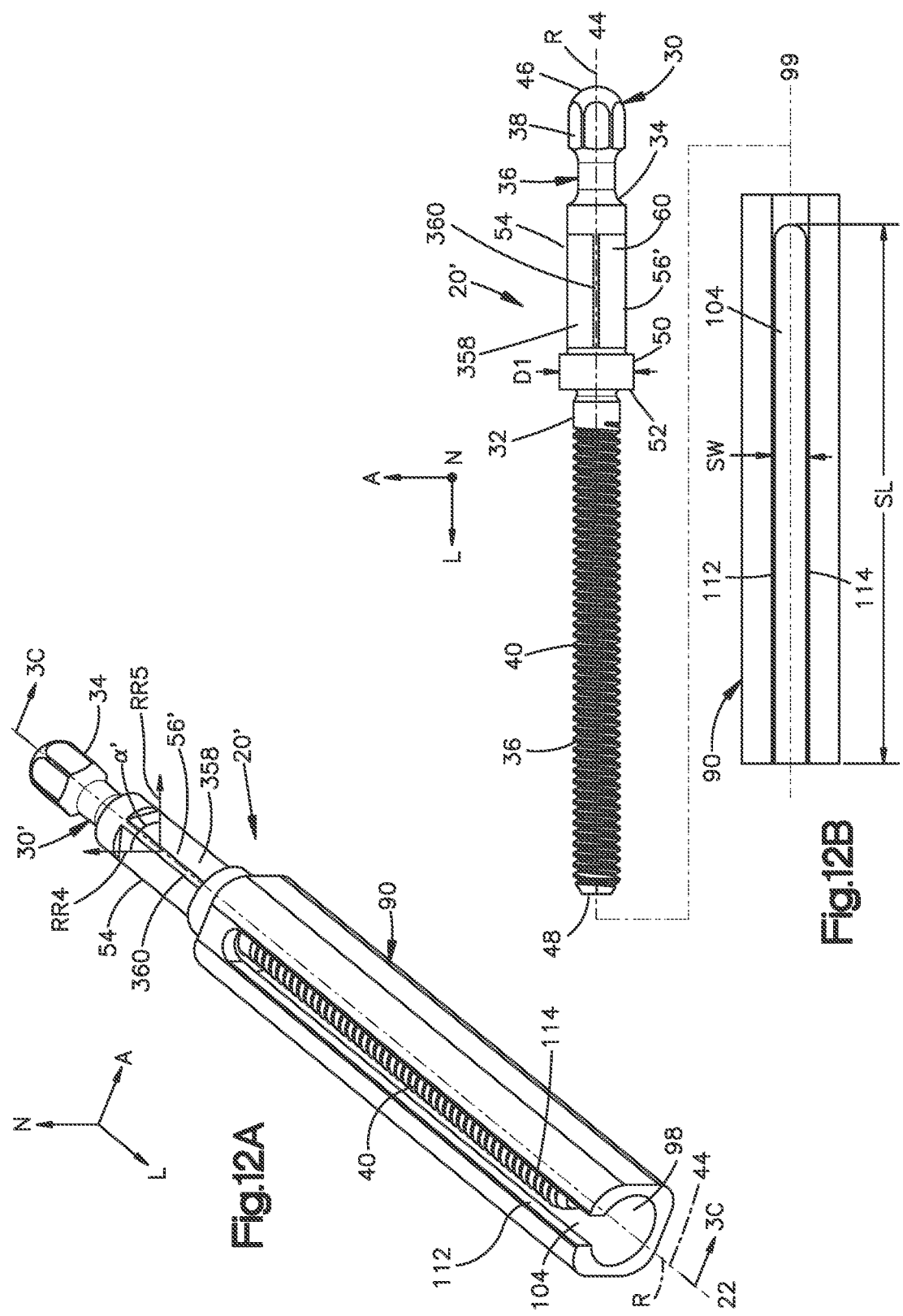

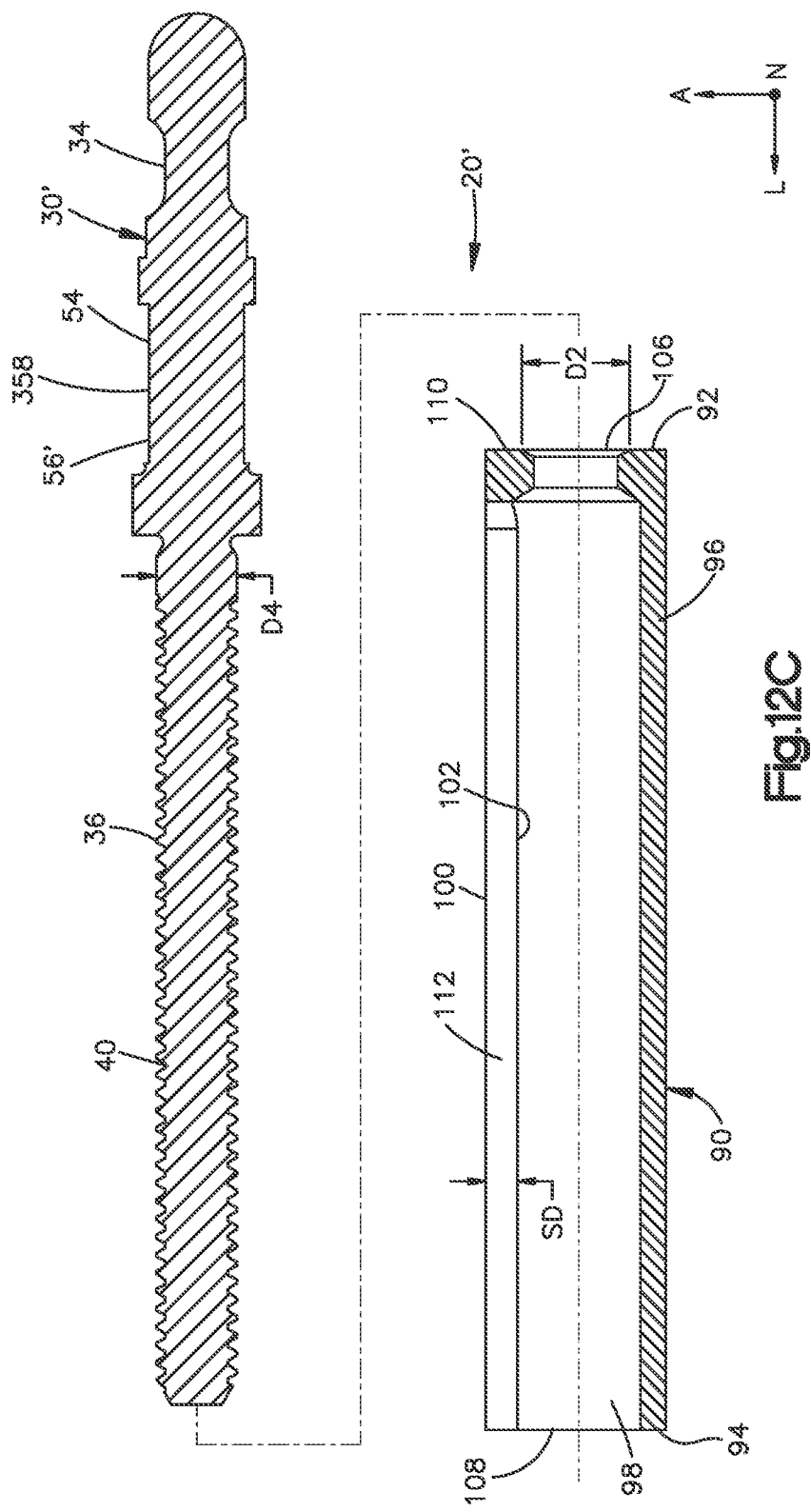

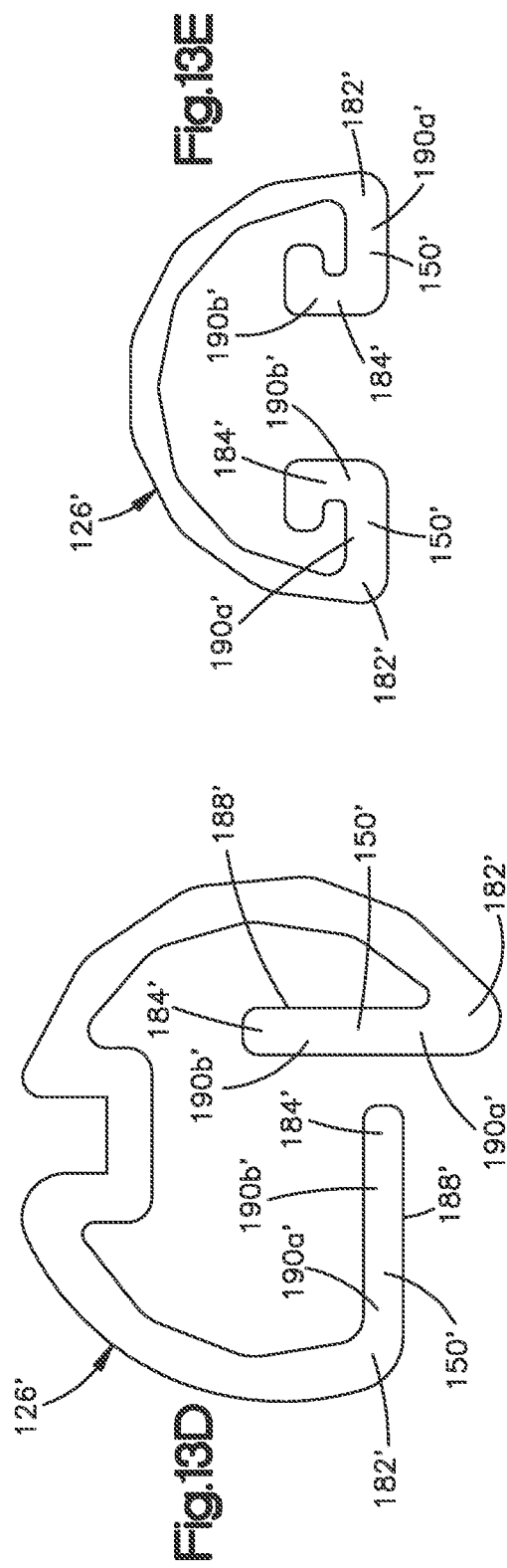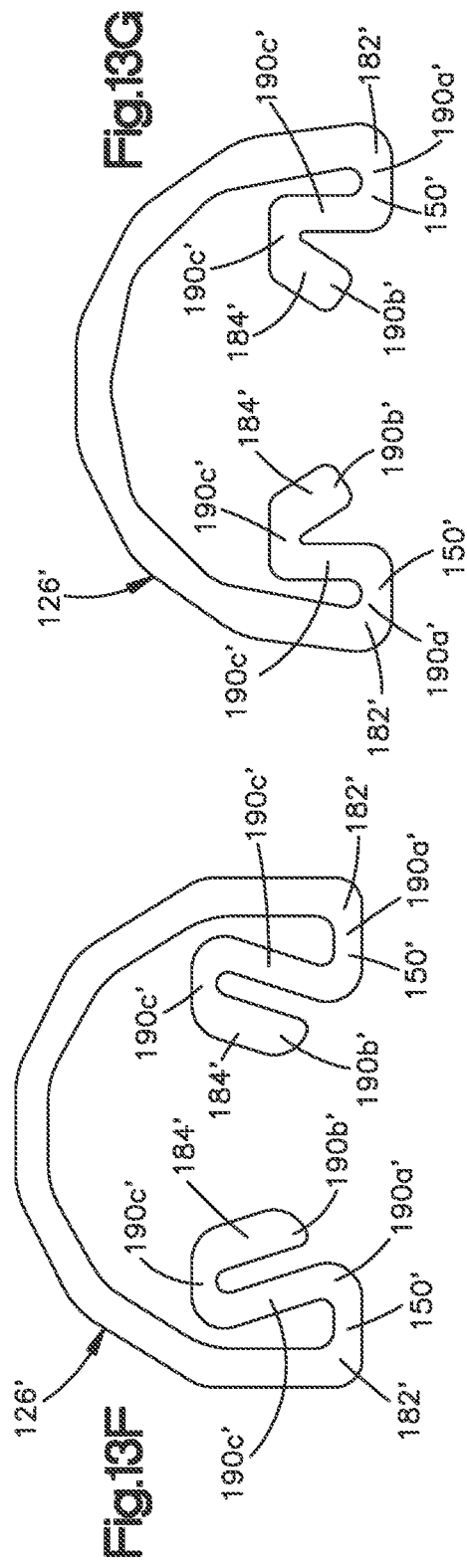

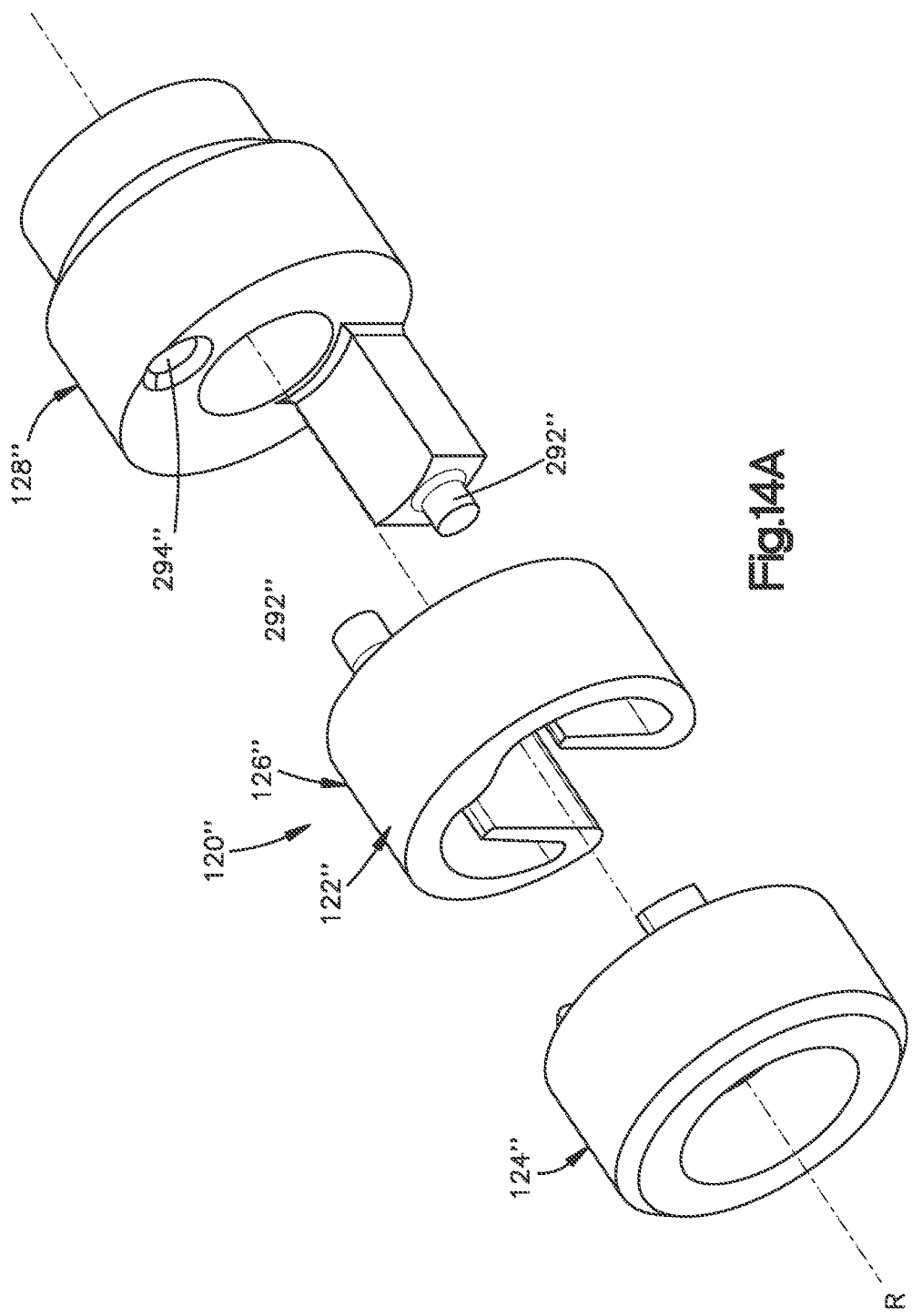

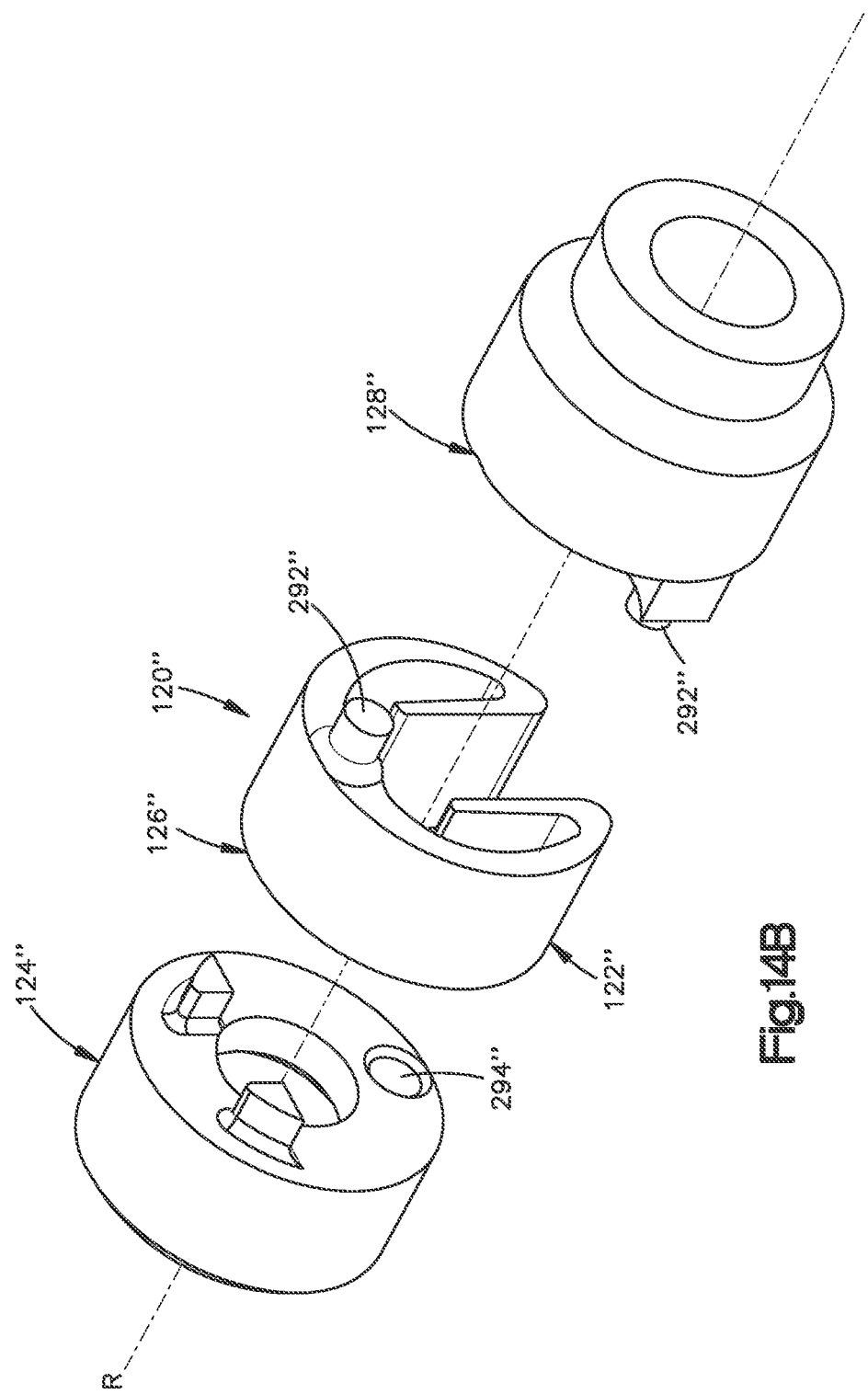

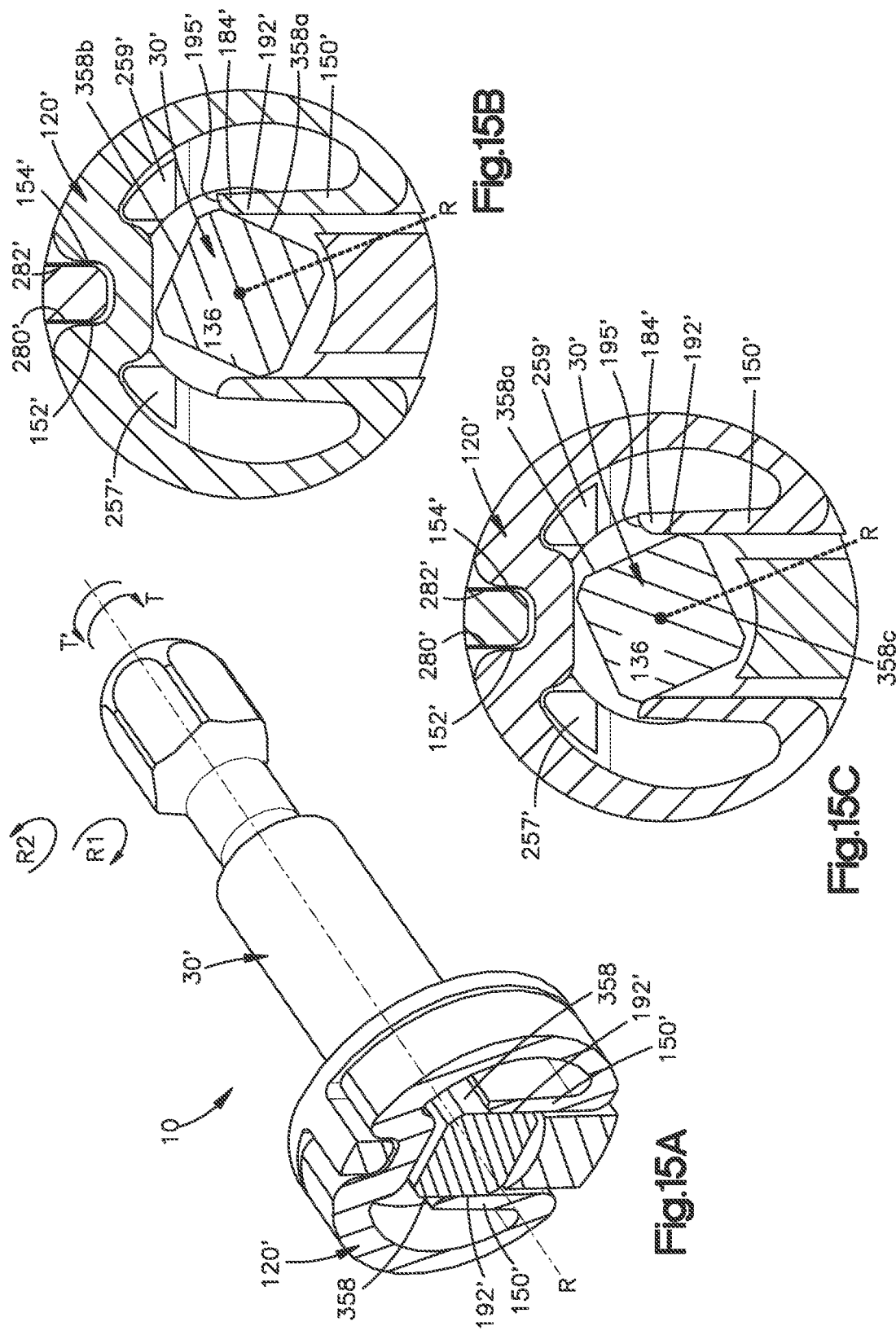

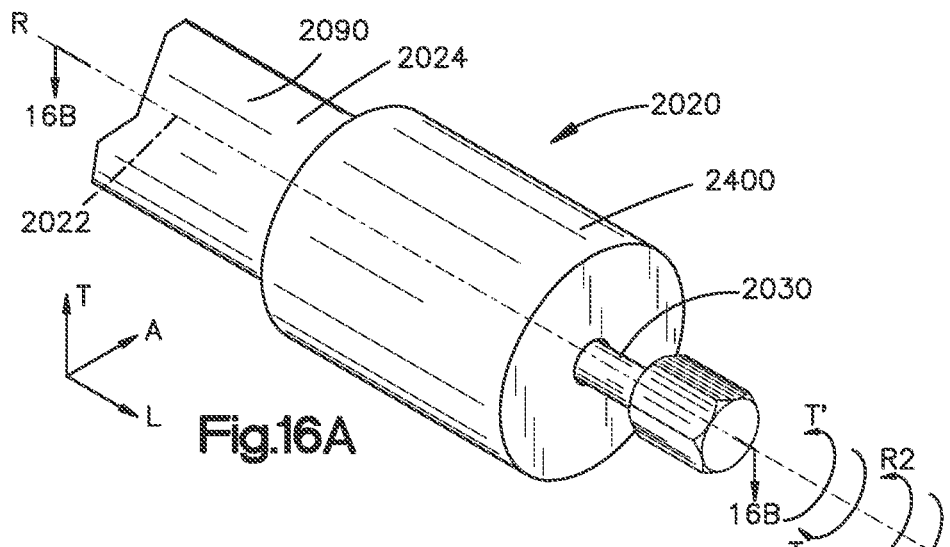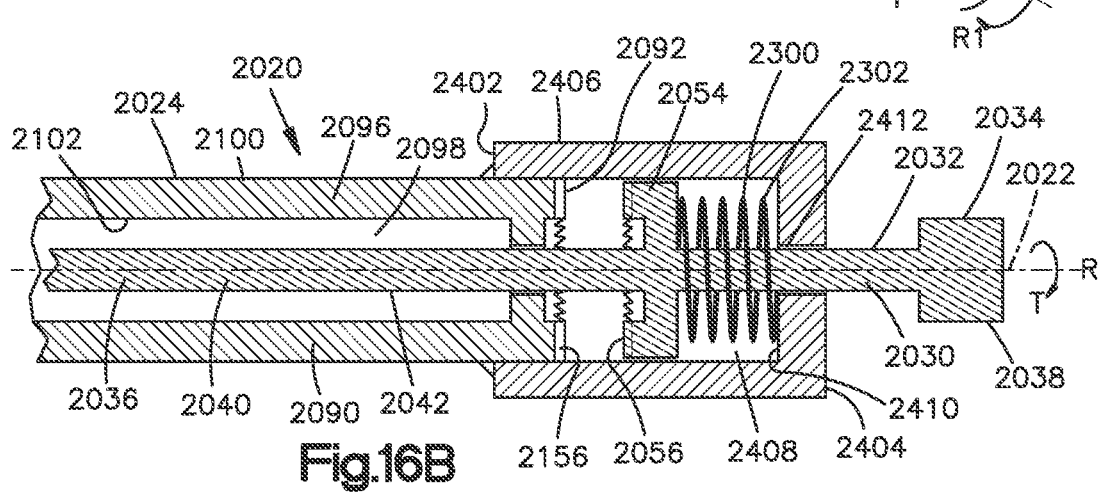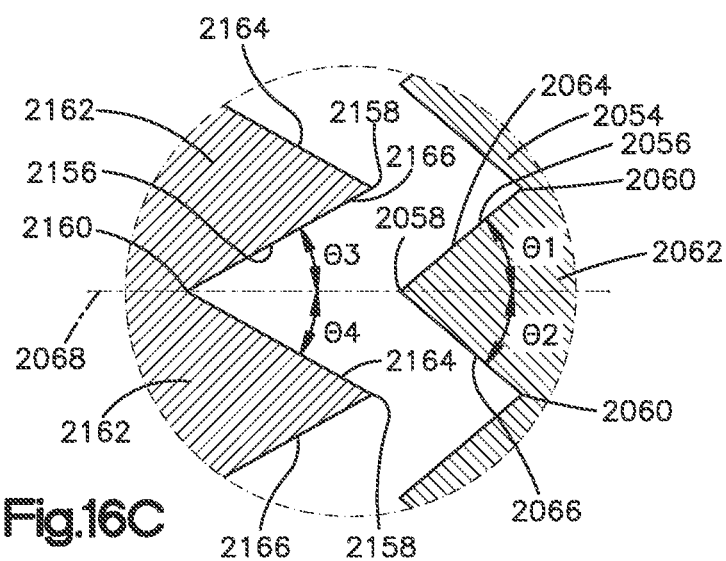

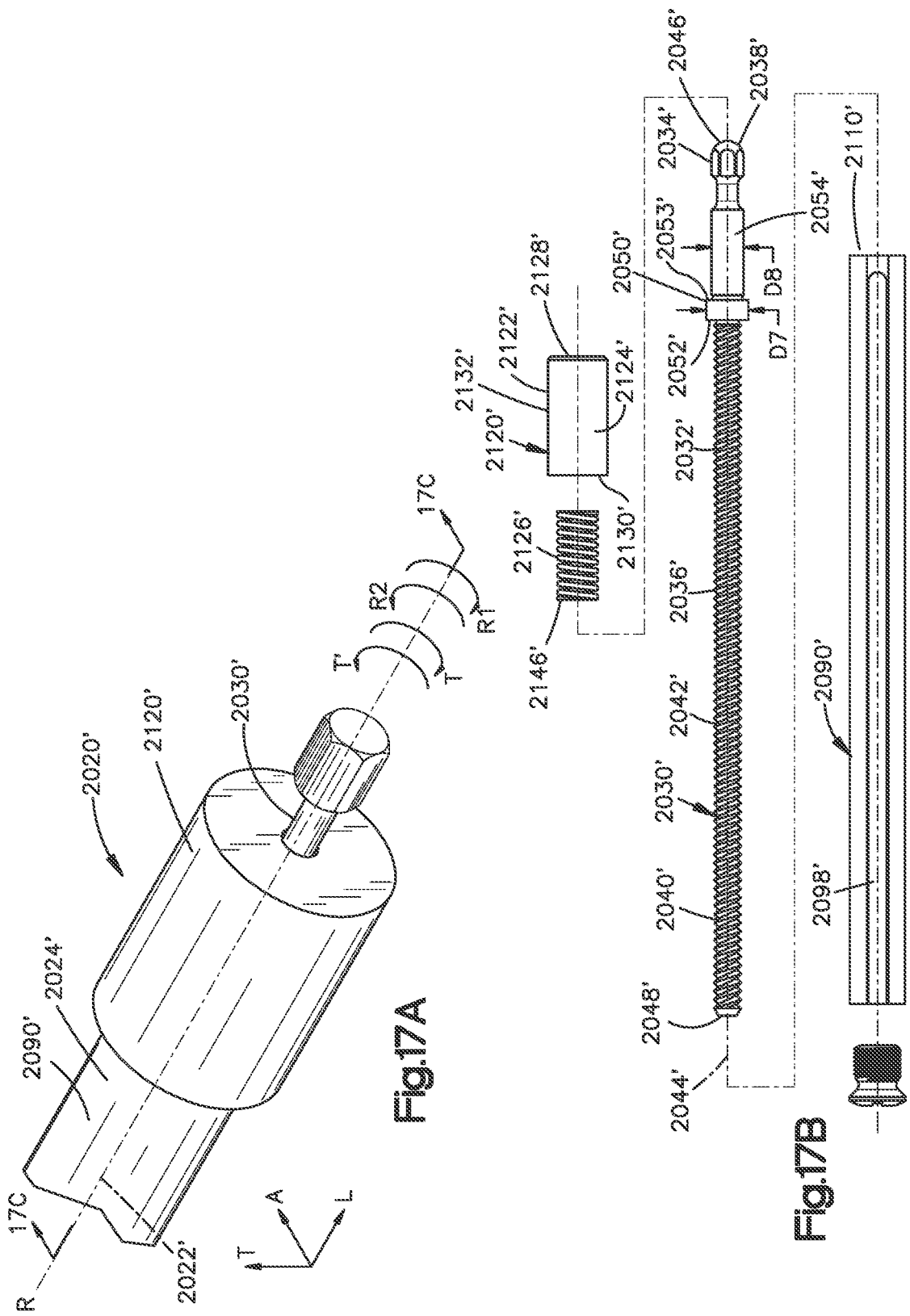

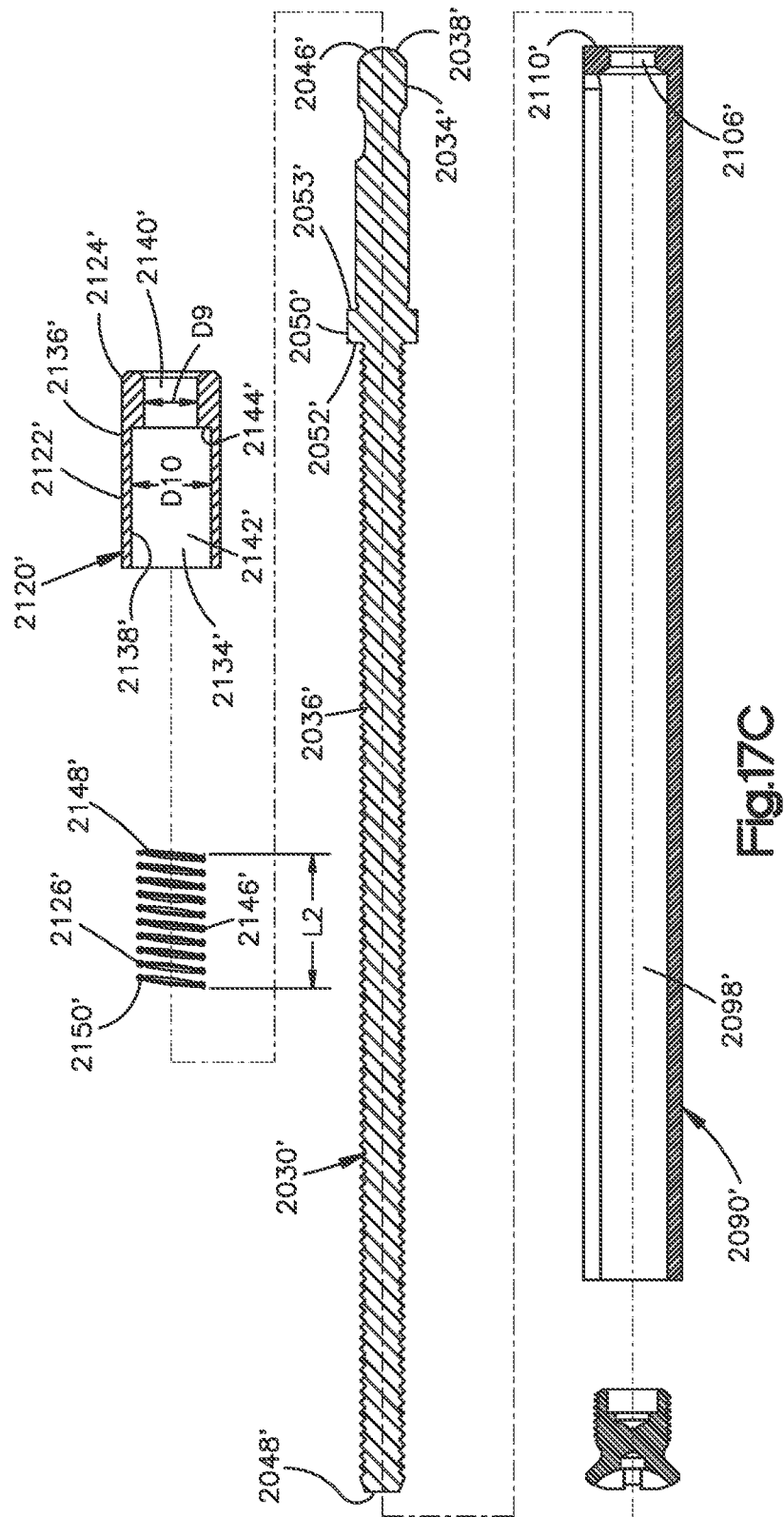

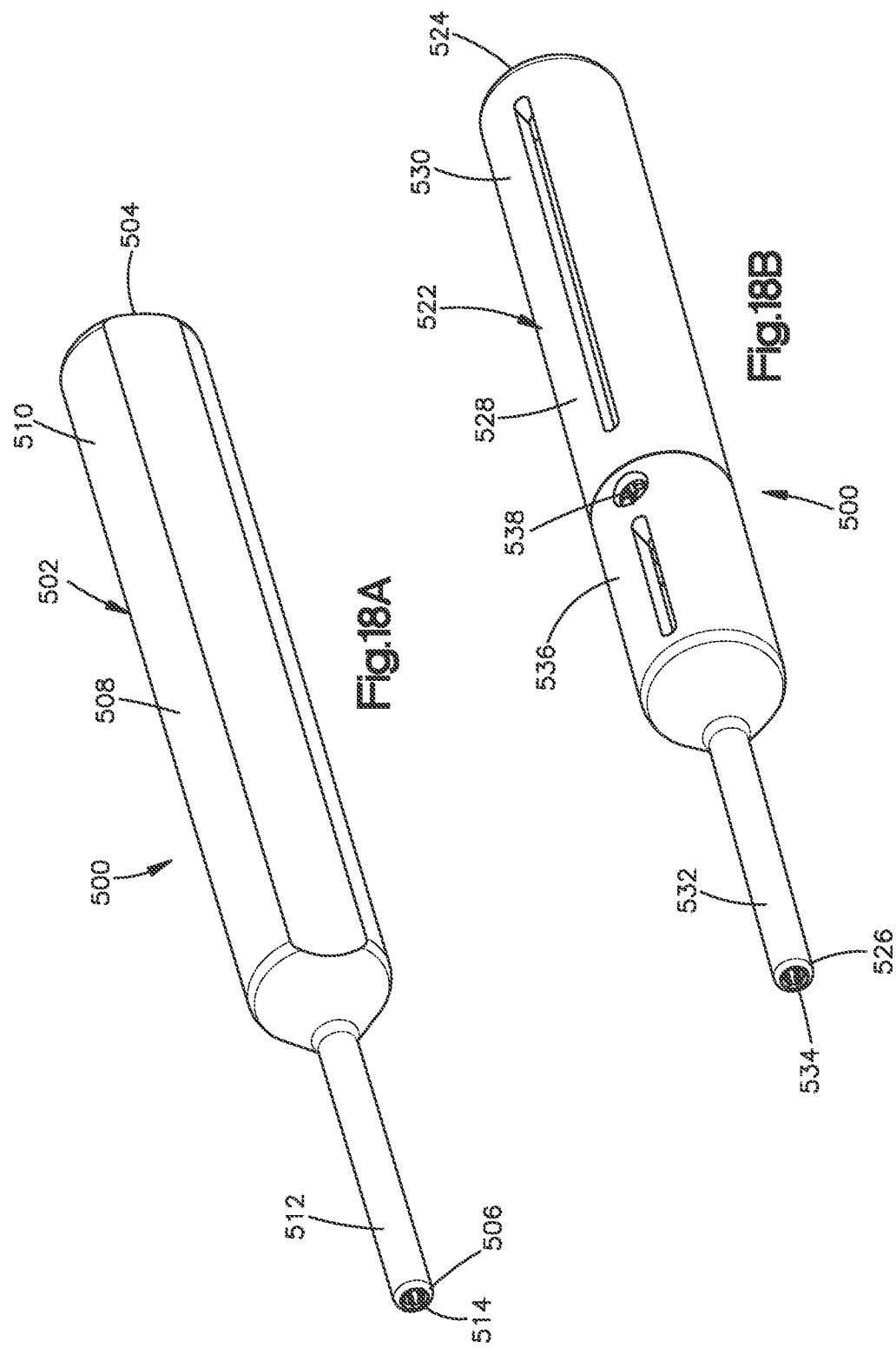

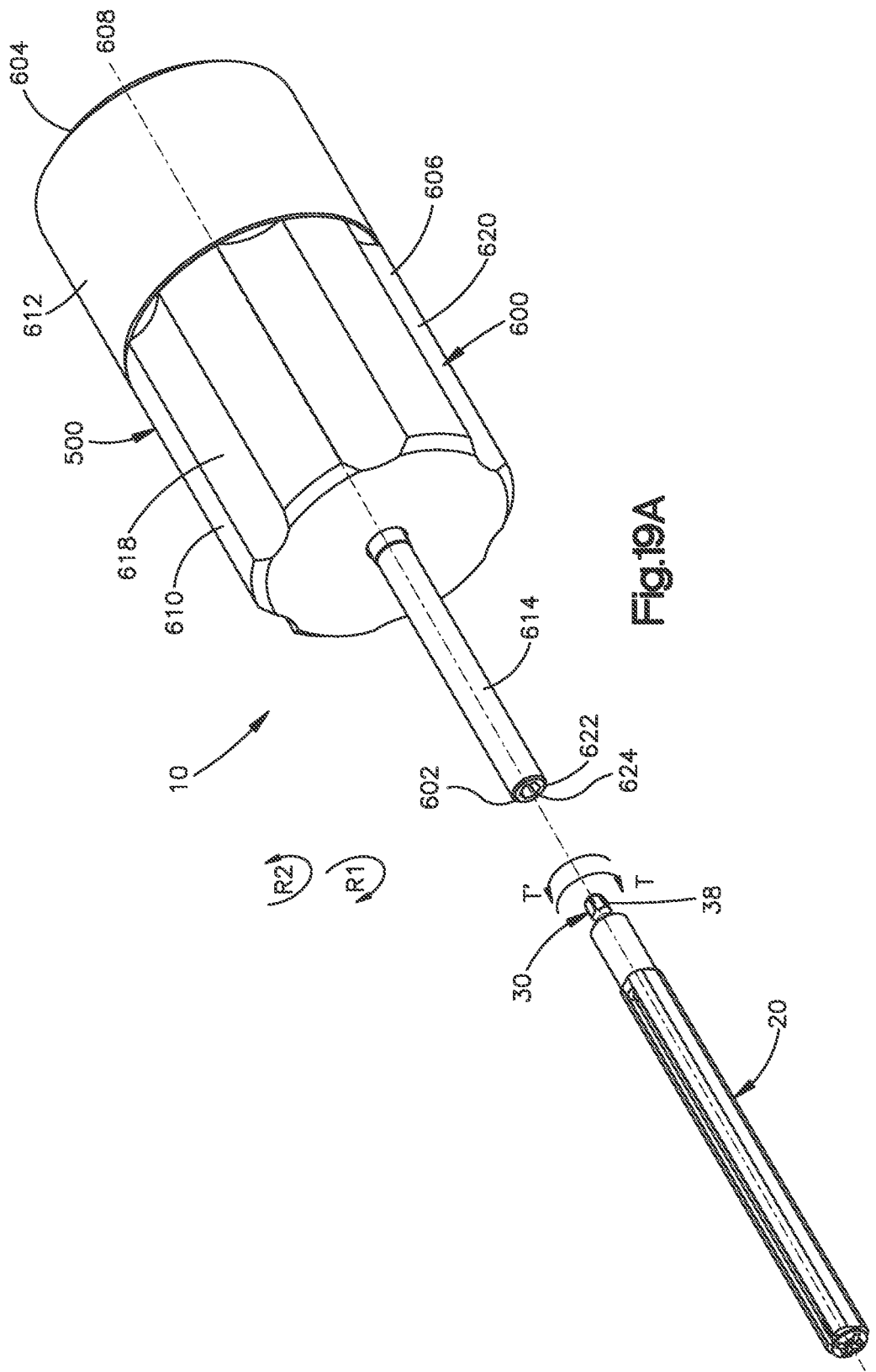

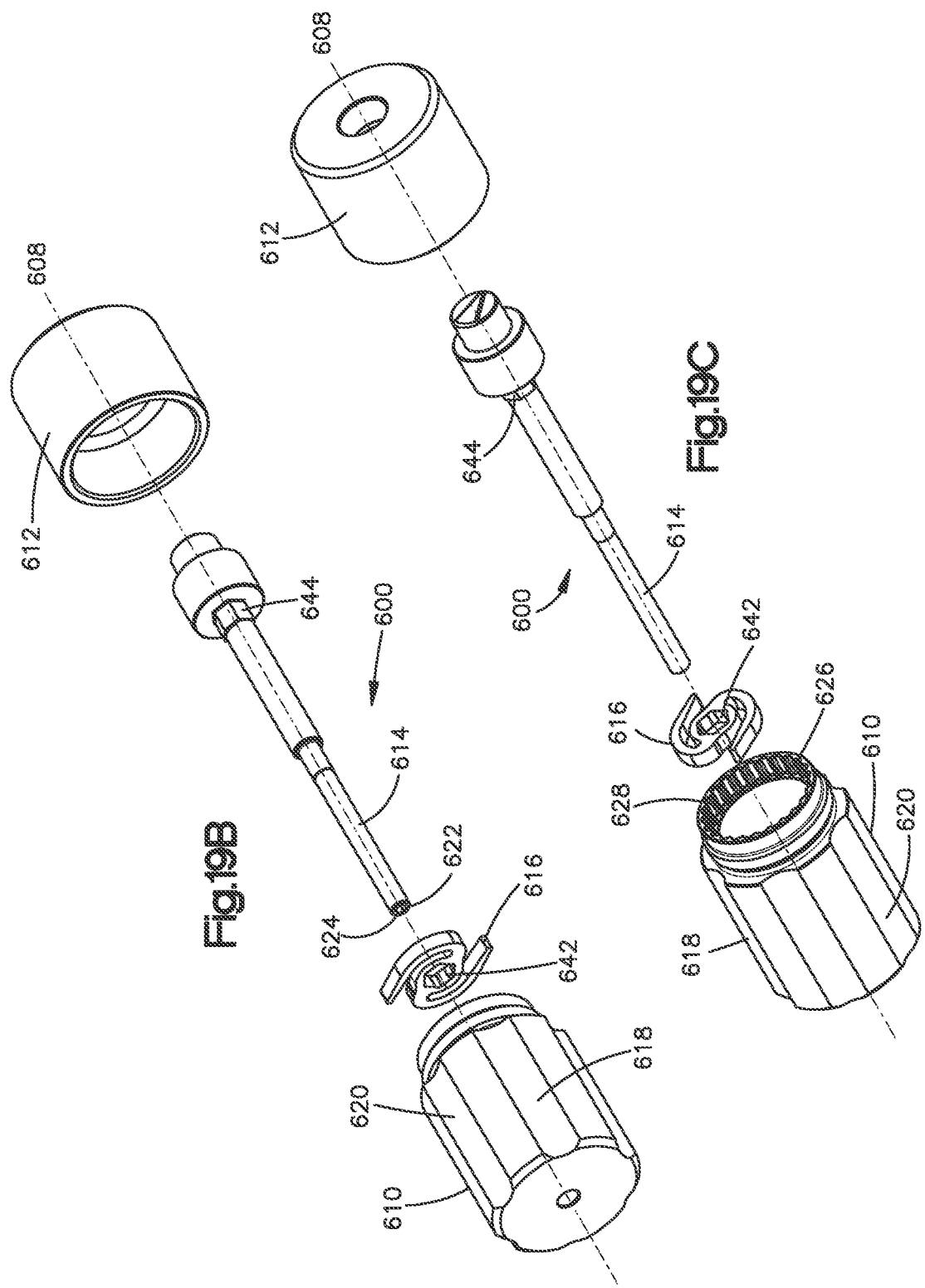

BONE DISTRACTION SYSTEM

CROSS REFERENCE TO RELATED APPLICATIONS

This is a continuation of U.S. patent application Ser. No. 14/668,443 filed Mar. 25, 2015, which claims benefit of U.S. Provisional Application No. 62/132,113 filed Mar. 12, 2015 and U.S. Provisional Application No. 61/971,782 filed Mar. 28, 2014, the disclosures of which are hereby incorporated by reference herein in their entireties.

TECHNICAL FIELD

The present application relates generally to orthopedics. More specifically, the present application relates to devices, kits, and methods for the repair of fractures or deformities in bones.

BACKGROUND

Craniofacial surgery can be used to correct a number of conditions of the jaw and face related to structure, growth, sleep apnea, correcting malocclusion problems owing to skeletal disharmonies or other orthodontic problems that cannot be easily treated with braces. During craniofacial surgery an osteotomy is often performed in which the bones can be cut, realigned, and held in place with either screws or plates and screws.

Distraction devices (commonly referred to as distractors), are used to gradually adjust the relative orientation and spacing of bone parts on opposing sides of an osteotomy. Distractors typically consist of transcutaneous pins or screws secured to the bone on either side of the osteotomy together with a mechanism that allows controlled incremental adjustment of the distance between parts of the distractor on opposing sides of the osteotomy and the bone segments the parts of the distractor are attached to. Typically, distractors are used to perform distraction osteogenesis (the formation of bone).

Some surgical procedures may include a series of adjustments to the bone segments that have been separated by the osteotomy. These adjustments may be spaced out over a relatively significant amount of time, for example a number of weeks or months. In some cases the patient of the surgical procedure may be instructed to perform a series of adjustments to the distractor to adjust the distance between the bone segments. For example the patient may be instructed to adjust the distractor to increase the distance between the bone segments by 1 mm (millimeter) once every day.

A typical distractor is adjustable such that the distance between the attached bone segments can be increased, for example by actuating the distractor in a first direction, and decreased, for example by actuating the distractor in a second direction. If the series of adjustments the patient is to perform are all in a single direction, for example, increasing the distance between the bone segments, a bone distraction system that prevents the patient from actuating the distractor in the incorrect direction may improve the results of the surgical procedure.

During the surgical procedure, the surgeon may wish to make adjustments to the distance between the bone segments in both directions, for example increasing and decreasing the distance. Thus, a bone distraction system that also allows the surgeon to actuate the distractor in both directions may improve the results of the surgical procedure.

SUMMARY

The present application discloses in accordance with one embodiment, a bone distraction system that includes a distractor including a distractor body, the distractor body having a sleeve and a screw, the screw positioned at least partially within the sleeve such that: 1) the screw is rotatable relative to the sleeve about an axis of rotation in a first direction of rotation only upon application of a first torque to the screw in the first direction of rotation, the first torque being equal to or greater than a first minimum torque value; and 2) the screw is rotatable relative to the sleeve about the axis of rotation in a second direction of rotation only upon application of a second torque to the screw in the second direction of rotation, the second torque being equal to or greater than a second minimum torque value, the second minimum torque value being greater than the first minimum torque value.

A bone distraction system is also provided that includes a distractor having a distractor body, the distractor body having a sleeve and a screw connected to the sleeve such that the screw is rotatable relative to the sleeve about an axis of rotation in a first direction of rotation and in a second direction of rotation that is opposite the first direction of rotation. The bone distraction system further includes a ratchet supported by the distractor body, the ratchet including a first surface and a second surface, wherein the first surface is positioned to interfere with the screw so as to block rotation of the screw relative to the ratchet about the axis of rotation in the first direction of rotation until a first torque equal to or greater than a first minimum value is applied to the screw, thereby causing the screw to cam over the first surface; and the second surface is positioned to interfere with the screw so as to block rotation of the screw relative to the ratchet about the axis of rotation in the second direction of rotation until a second torque equal to or greater than a second minimum value is applied to the screw, thereby causing the screw to cam over the second surface.

A bone distractor is also provided that includes a sleeve, and a screw that is extends at least partially into the sleeve such that: 1) the screw is rotatable relative to the sleeve about an axis of rotation in a first direction of rotation only upon application of a first minimum torque value to the screw; and 2) the screw is rotatable relative to the sleeve about an axis of rotation in a second direction of rotation only upon application of a second minimum torque value to the screw, the second minimum torque value being greater than the first minimum torque value.

A method is also provided including the steps of applying a first torque to a screw of a distractor that causes the screw to rotate relative to a sleeve of the distractor about an axis of rotation in a first direction of rotation, the first torque being equal to or greater than a first minimum torque value; applying a second torque to the screw of the distractor in a second direction of rotation that is opposite the first direction of rotation, such that the second torque results in no rotation of the screw relative to the sleeve about the axis of rotation in the second direction of rotation, the second torque being equal to the first minimum torque value; and applying a third torque to the screw of the distractor in the second direction of rotation causing the screw to rotate relative to the sleeve about the axis of rotation in the second direction, the third torque being equal to or greater than a second minimum torque value that is greater than the first minimum torque value.

A bone distraction system is provided that includes a distractor that has a distractor body, the distractor body having a sleeve and a screw, the screw positioned at least partially within the sleeve such that: 1) the screw is rotatable relative to the sleeve about an axis of rotation in a first direction of rotation only upon application of a first torque to the screw in the first direction of rotation, the first torque being equal to or greater than a first minimum torque value; and 2) the screw is rotatable relative to the sleeve about the axis of rotation in a second direction of rotation only upon application of a second torque to the screw in the second direction of rotation, the second torque being equal to or greater than a second minimum torque value, wherein both the first minimum torque value and the second minimum torque value is greater than zero.

BRIEF DESCRIPTION OF THE DRAWINGS

The foregoing summary, as well as the following detailed description of illustrative embodiments of the bone distraction system of the present application, will be better understood when read in conjunction with the appended drawings. For the purposes of illustrating the bone distraction system of the present application, there is shown in the drawings illustrative embodiments. It should be understood, however, that the application is not limited to the precise arrangements and instrumentalities shown. In the drawings:

FIG. 3A is a perspective view of the distractor illustrated in FIG. 2A, the distractor including a screw and a sleeve;

FIG. 3B is an exploded top plan view of the distractor illustrated in FIG. 3A;

FIG. 3C is an exploded cross sectional view of the distractor illustrated in FIG. 3A, along line 3C-3C;

FIG. 5A is a top plan view of the distractor and ratchet illustrated in FIG. 2A;

FIG. 5B is a side cross-sectional view of the distractor and ratchet illustrated in FIG. 5A along line 5B-5B;

FIG. 5C is a perspective cross-sectional view of the distractor and ratchet illustrated in FIG. 5A along line 5B-5B;

FIG. 6B is a front cross-sectional view of the distractor and ratchet illustrated in FIG. 5A along line 6A-6A, the ratchet and distractor in the first orientation;

FIG. 6C is a front cross-sectional view of the distractor and ratchet illustrated in FIG. 5A along line 6A-6A, the ratchet and distractor in a second orientation;

FIG. 6D is a front cross-sectional view of the distractor and ratchet illustrated in FIG. 5A along line 6A-6A, the ratchet and distractor in a third orientation;

FIG. 7B is another perspective view of the bone distraction system illustrated in FIG. 7A;

FIG. 8A is a front cross-sectional view of the distractor and the ratchet illustrated in FIG. 7A along line 8A-8A, the distractor including a securing element, and the distractor and the ratchet in a disengaged configuration;

FIG. 8B is a front cross-sectional view of the distractor and the ratchet illustrated in FIG. 7A along line 8A-8A, the distractor and the ratchet in an engaged configuration;

FIG. 9 is a side elevation view of the securing element illustrated in FIG. 7A according to one embodiment;

FIG. 10A is a perspective view of the securing element illustrated in FIG. 7A according to another embodiment, the securing element including a stepped pull pin and a wire;

FIG. 10B is a top plan view of the stepped pull pin illustrated in FIG. 10A;

FIG. 10C is a side elevation view of the stepped pull pin illustrated in FIG. 10A;

FIG. 11 is a perspective view of the bone distraction system illustrated in FIG. 1, the bone distraction system including a distractor according to another embodiment, a ratchet according to another embodiment, and the first footplate and the second footplate illustrated in FIG. 2A;

FIG. 12A is a perspective view of the distractor illustrated in FIG. 11;

FIG. 12B is a top plan exploded view of the distractor illustrated in FIG. 12A;

FIG. 12C is an exploded cross-sectional view of the distractor illustrated in FIG. 12A along line 12C-12C;

FIG. 13D is a front view of the ratchet tab of the ratchet illustrated in FIG. 11, according to another embodiment;

FIG. 13E is a front view of the ratchet tab of the ratchet illustrated in FIG. 11, according to another embodiment;

FIG. 13F is a front view of the ratchet tab of the ratchet illustrated in FIG. 11, according to another embodiment;

FIG. 13G is a front view of the ratchet tab of the ratchet illustrated in FIG. 11, according to another embodiment;

FIG. 14A is an exploded perspective view of the ratchet according to another embodiment, the ratchet including a first collar member, a ratchet tab, and a second collar member;

FIG. 14B is another exploded perspective view of the ratchet illustrated in FIG. 14A;

FIG. 15A is a perspective cross-sectional view of the distractor and ratchet illustrated in FIG. 11 along line 15A-15A, the ratchet and distractor in a first orientation;

FIG. 15B is a front cross-sectional view of the distractor and ratchet illustrated in FIG. 15A, the ratchet and distractor in a second orientation;

FIG. 15C is a front cross-sectional view of the distractor and ratchet illustrated in FIG. 15A, the ratchet and distractor in a third orientation;

FIG. 16A is a perspective view of a distractor according to another embodiment, the distractor including a screw, a sleeve, and a collar.

FIG. 16B is a side cross-sectional side view of the distractor illustrated in FIG. 16A along line 16B-16B, the distractor in a disengaged configuration;

FIG. 16C is an enlarged view of a portion of the distractor illustrated in FIG. 16B;

FIG. 17A is a perspective view of a distractor according to another embodiment and a friction assembly.

FIG. 17B is a top exploded view of the distractor and friction assembly illustrated in FIG. 17A;

FIG. 17C is an exploded cross-sectional view of the distractor and friction assembly illustrated in FIG. 17A along line 17C-17C;

FIG. 18A is a perspective view of a first instrument configured to actuate the distractor;

FIG. 18B is a perspective view of a second instrument configured to actuate the distractor;

FIG. 19A is a perspective view of an instrument configured to actuate the distractor, according to another embodiment;

FIG. 19B is an exploded perspective view of the instrument illustrated in FIG. 19A;

FIG. 19C is another exploded perspective view of the instrument illustrated in FIG. 19A;

DETAILED DESCRIPTION OF ILLUSTRATIVE EMBODIMENTS

Certain terminology is used in the following description for convenience only and is not limiting. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. Further, reference to values stated in ranges includes each and every value within that range. All ranges are inclusive and combinable. Certain features of the invention which are described herein in the context of separate embodiments may also be provided in combination in a single embodiment. Conversely, various features of the invention that are described in the context of a single embodiment may also be provided separately or in any subcombination.

A radial or polar coordinate system is provided and described herein. The polar coordinate system includes a two dimensional radial plane that is centered on and normal to a reference axis, for instance an axis of elongation or an axis of rotation. The polar coordinate system defines a radial component that is measured as the distance from the reference axis along the plane. Accordingly, the term "radial length" refers to a length measured along a radial ray that extends from the reference axis. The words "inner" and "outer" designate locations closer to and farther away from the reference axis respectively.

The polar coordinate system further defines an angular component that is measured as the angular position about the reference axis. Accordingly, the term "angular length" refers to a length measured along a curved line that is a constant radial distance away from the reference axis. The radial length can be measured in degrees such that the radial length of a circle centered on a reference axis would be 360°.

Reference to multiple components being "translationally secured" relative to an axis or a direction means the identified components are prevented from translating relative to one another along the identified axis or direction. Reference to multiple components being "rotationally secured" relative to an axis or a direction of rotation means the identified components are prevented from rotating relative to one another about the identified axis or direction of rotation.

The polar coordinate system can be converted to a three dimensional coordinate system, for instance a right-hand coordinate system that includes a longitudinal direction L that is coincident with the reference axis, a lateral direction A that is perpendicular to the longitudinal direction L, and a transverse direction N that is perpendicular to both the longitudinal direction L and the lateral direction A. The longitudinal direction L and the lateral direction A collectively define a plane that corresponds to or is parallel to the radial plane.

Figure 1:
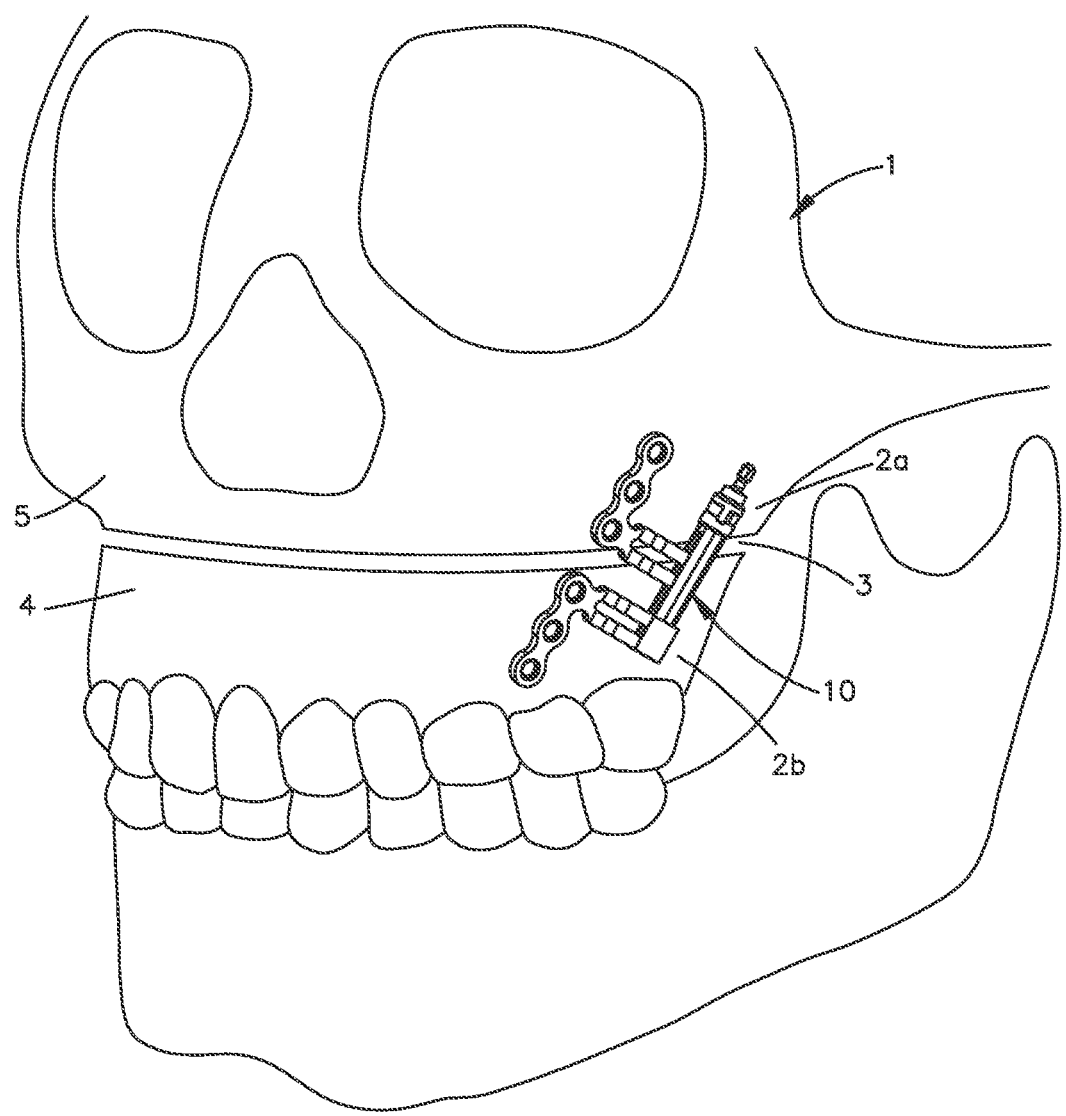
FIG. 1 is a perspective view of a conventional skull and a bone distraction system according to one embodiment secured to the skull, the skull including a maxilla and a remaining portion of the skull that has been separated from the maxilla by an osteotomy.

Referring to FIG. 1, a bone distraction system 10 can be constructed to as to attach to a first bone segment 2a and a second bone segment 2b that is separated from the first bone segment 2a by a gap 3. As shown in the illustrated embodiment, the bone distraction system 10 is configured to be attached to a skull 1 that includes a maxilla 4, and a remaining portion 5 that has been separated from the maxilla 4 by an osteotomy that has been performed on the skull 1. After a surgical procedure has been performed, for example an osteotomy that separates the first bone segment 2a from the second bone segment 2b by a gap 3, it may be desirable to control the size of the gap 3 over an extended period of time.

For example, as the first bone segment 2a and the second bone segment 2b heal and grow new bone towards each other to close the gap 3, it may be desired to incrementally increase the size of the gap 3 to result in the eventual elongation of the original underlying boney structure that includes the first bone segment 2a and the second bone segment 2b. The bone distraction system 10 is configured to be secured to the first bone segment 2a and the second bone segment 2b, and then actuated to either increase or decrease the size of the gap 3 between the first bone segment 2a and the second bone segment 2b.

In one embodiment it may be desirable for the size of the gap 3 to be adjustable such that the size of the gap 3 can be increased in size and decreased in size in the same surgical procedure, for instance by a surgeon performing the initial placement of the bone distraction system 10 and setting the initial size of the gap 3. In another embodiment it may further be desirable for the gap 3 to only be adjustable in a single direction, either to be increased in size or decreased in size, by a patient over the course of a period of time after the initial placement of the bone distraction system 10 by the surgeon. Accordingly, in one embodiment, the bone distraction system 10: 1) is configured to be actuated by a first user to both increase or decrease the gap 3 between the first bone segment 2a and the second bone segment 2b; and 2) is also configured to be actuated by a second user to either increase or decrease the gap 3.

Figure 2A:
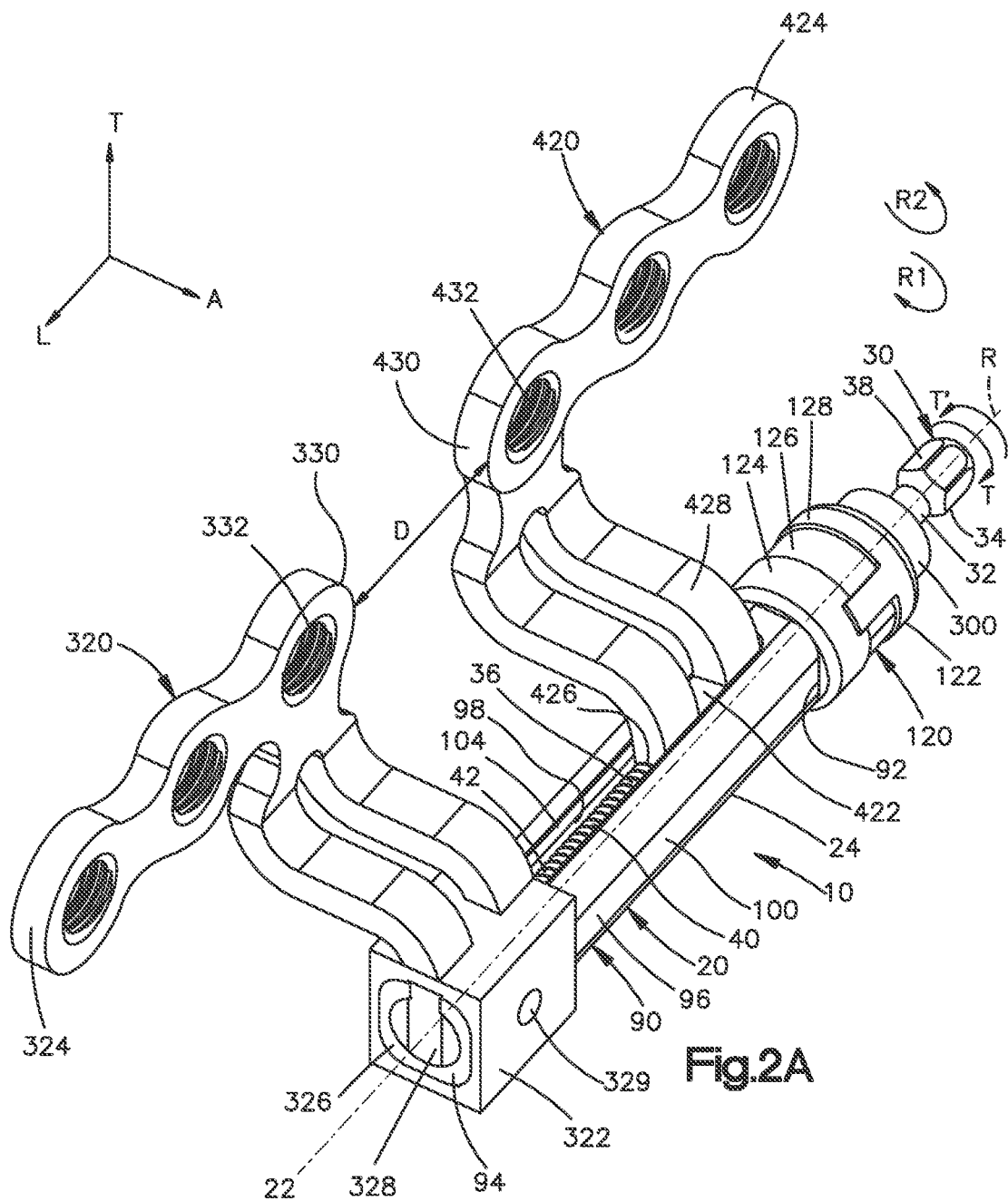
FIG. 2A is a perspective view of the bone distraction system illustrated in FIG. 1, the bone distraction system including a distractor according to one embodiment, a ratchet according to one embodiment, a first footplate and a second footplate, the first footplate spaced from the second footplate by a first distance.
Figure 2B:
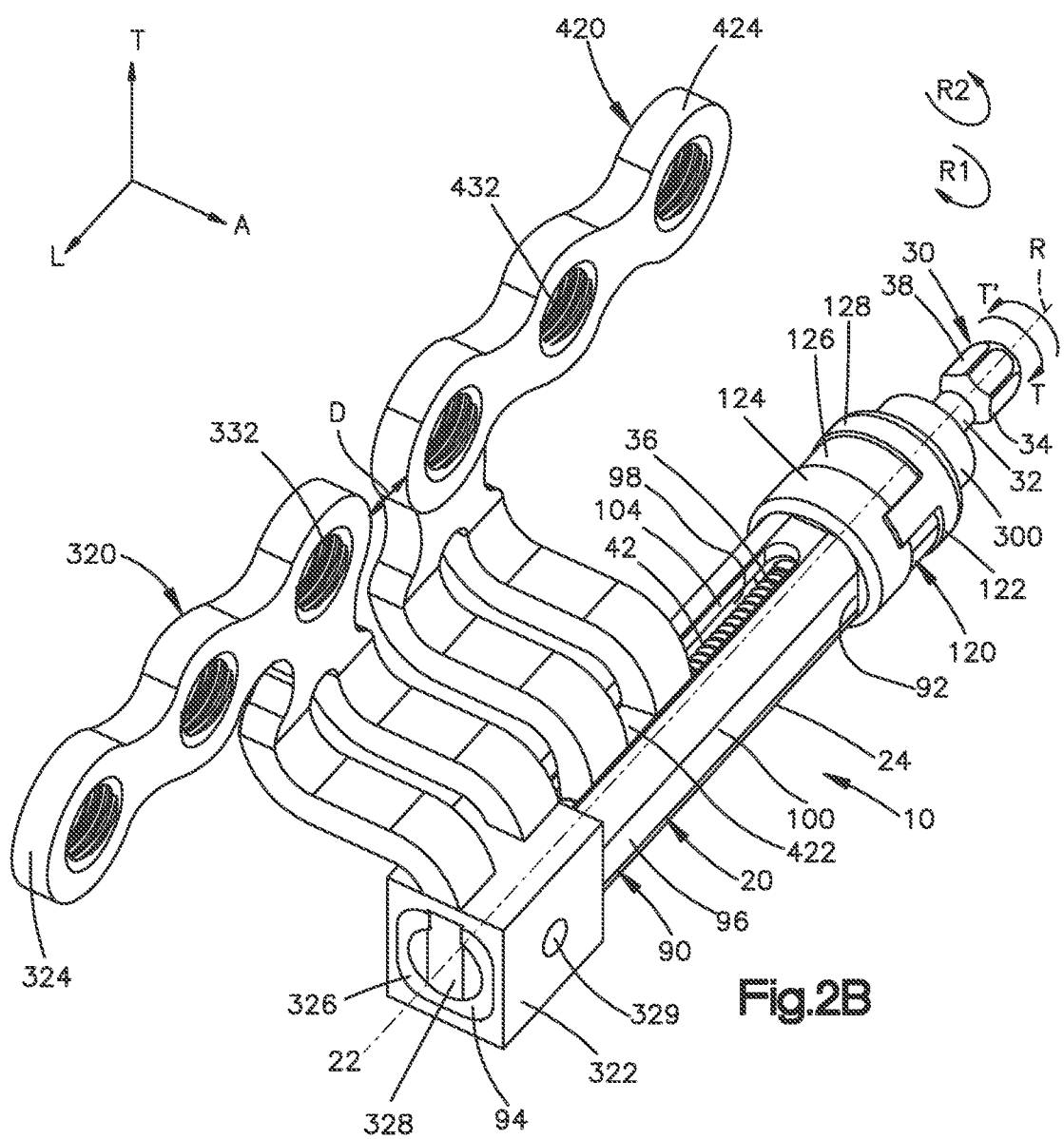
FIG. 2B is a perspective view of the bone distraction system illustrated in FIG. 2A, the first footplate spaced from the second footplate by a second distance.

Referring to FIGS. 1 and 2A-2B, the bone distraction system 10 includes, in one embodiment, a distractor 20, a ratchet 120, a first footplate 320, and a second footplate 420. In another embodiment the bone distraction system 10 includes any one of or any combination of the distractor 20, the ratchet 120, the first footplate 320, and the second footplate 420. The bone distraction system 10 is configured to be attached to the first bone segment 2a and the second bone segment 2b such that actuation of the bone distraction system 10 adjusts the gap 3 between the first bone segment 2a and the second bone segment 2b. As shown in the illustrated embodiment, the first footplate 320 is configured to be attached to the first bone segment 2a and the second footplate 420 is configured to be attached to the second bone segment 2b, such that actuation of the distractor 20 adjusts a distance D between the first footplate 320 and the second footplate 420 which adjusts the size of the gap 3 between the first bone segment 2a and the second bone segment 2b.

The distractor 20 is elongate along a distractor axis 22 and includes a distractor body 24. In one embodiment, the distractor axis 22 is a straight line extending in the longitudinal direction L. In another embodiment the distractor axis 22 extends centrally through the distractor 20. The distractor body 24 includes a screw 30 and a sleeve 90 that are configured to be connected to one another such that the screw 30 is rotatable relative to the sleeve 90 about the distractor axis 22. As shown in the illustrated embodiment, the sleeve 90 includes a first end 92, a second end 94 spaced from the first end 92, and a sleeve body 96 that extends from the first end 92 to the second end 94. The sleeve 90 further includes a sleeve borehole 98 that extends through the sleeve body 96 between the first end 92 and the second end 94, for example from the first end 92 to the second end 94.

Figure 3D:
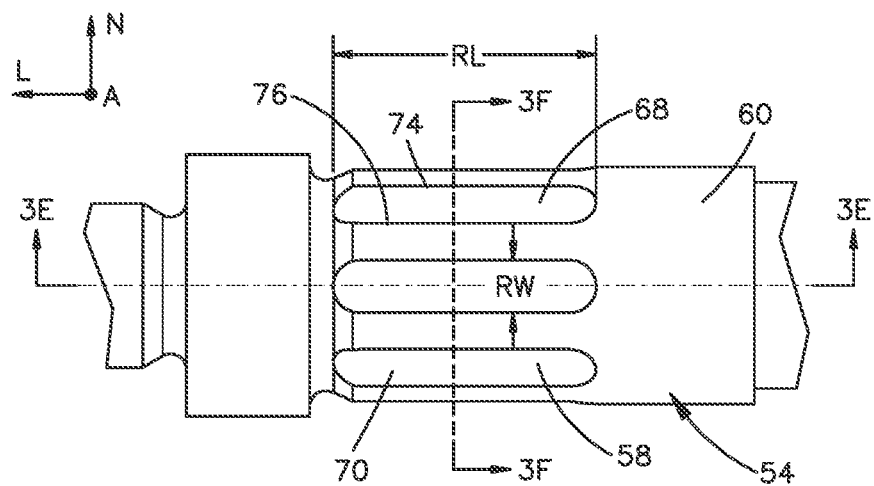
FIG. 3D is an enlarged top plan view of a portion of the distractor illustrated in FIG. 3A.
Figure 3E:
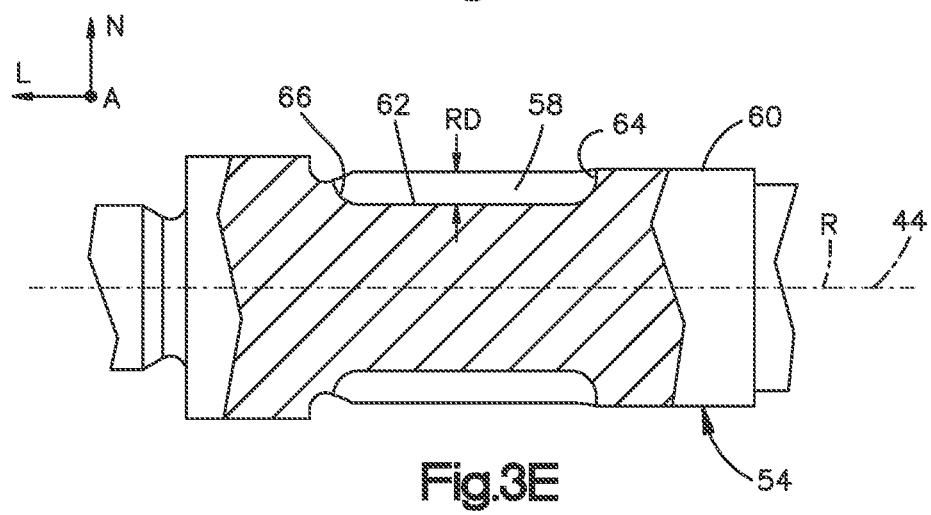
FIG. 3E is an enlarged side cross sectional view of the portion of the distractor illustrated in FIG. 3D, along line 3E-3E.
Figure 3F:
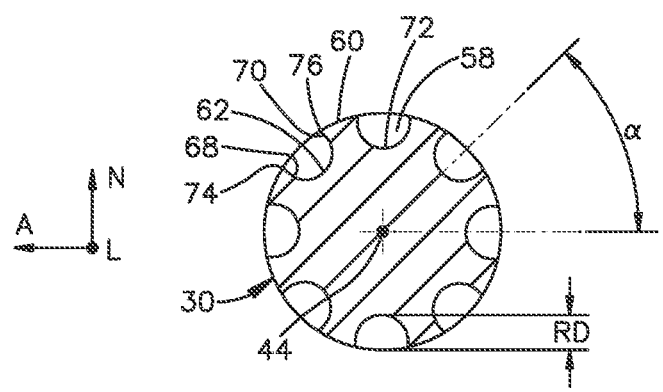
FIG. 3F is an enlarged front cross sectional view of the portion of the distractor illustrated in FIG. 3D, along line 3F-3F.

The sleeve body 96 includes an outer surface 100 that extends between the first end 92 and the second end 94. The sleeve body 96 further includes an inner surface 102 that is opposite the outer surface 100 and that extends between the first end 92 and the second end 94 such that the inner surface 102 at least partially defines the sleeve borehole 98. The sleeve 90 defines a slot 104 that extends through the sleeve body 96 in a direction perpendicular to the distractor axis 22, for example the transverse direction T, from the outer surface 100 to the inner surface 102 such that the sleeve borehole 98 is open to an exterior of the sleeve 90 through the slot 104. The slot 104 also extends between the first end 92 and the second end 94 in a direction parallel to the distractor axis 22, for example the longitudinal direction L, such that the slot 104 defines a length SL (see FIG. 3B).

The screw 30 includes a screw body 32 having a first portion 34 and a second portion 36. The first portion 34 includes an actuation mechanism 38 configured to receive a sufficient torque T that rotates the screw 30 about an axis of rotation R when the screw 30 is connected to the sleeve 90. In one embodiment the distractor 20 is configured such that the sufficient torque T is applied in a first direction of rotation R1 to rotate the screw 30 about the axis of rotation R in the first direction of rotation R1. The distractor 20 can further be configured such that the screw 30 is configured to receive a sufficient torque T' applied in a second direction of rotation R2, for example opposite the first direction of rotation R1, to rotate the screw 30 about the axis of rotation R in the second direction of rotation R2. Thus, in accordance with one embodiment, the system 10 includes a distractor 20 including a screw 30 and a sleeve 90, the screw 30 configured to receive a sufficient torque T that is required to rotate the screw 30 relative to the sleeve 90 in the first direction of rotation R1. The screw 30 further configured to receive a sufficient torque T' that is required to rotate the screw 30 relative to the sleeve in a second direction of rotation R2. As described in greater detail below, the sufficient torque T and the sufficient torque T' can be the same in one embodiment, or they can be different in another embodiment.

As shown in the illustrated embodiment, the axis of rotation R can be coincident with the distractor axis 22. In another embodiment the axis of rotation R can be displaced from the distractor axis 22. In one embodiment the second portion 36 includes a shaft 40 having external threads 42. As shown in the illustrated embodiment, the screw 30 is configured to be connected to the sleeve 90 such that the second portion 36 is disposed within the sleeve borehole 98 and the first portion 34 is disposed outside of the sleeve borehole 98.

The first footplate 320 includes a base portion 322 and an attachment portion 324. The base portion 322 defines a first opening 326. As shown in the illustrated embodiment, the first opening 326 has a shape that corresponds to a shape of the outer surface 100 of the sleeve body 96, such that the first opening 326 is configured to receive the outer surface 100 of the sleeve body 96. In one embodiment the shape of the outer surface 100 and the first opening 326 are non-circular such that when the outer surface 100 is inserted into the first opening 326, the first footplate 320 and the sleeve 90 are rotationally secured such that the first footplate 320 and the sleeve 90 cannot rotate with respect to each other about the axis of rotation R. In another embodiment the shape of the outer surface 100 and the first opening 326 are circular such that when the outer surface 100 is inserted into the first opening 326, the first footplate 320 and the sleeve 90 are rotatable with respect to each other about the axis of rotation R.

The bone distraction system 10, in one embodiment, further includes a securing screw 328. The securing screw 328 is configured to be inserted into the sleeve borehole 98 to translationally secure the first footplate 320 and the sleeve 90 such that the first footplate 320 and the sleeve 90 cannot translate relative to each other along the axis of rotation R. In another embodiment the bone distraction system 10 can include a set screw 329 configured to be inserted through the base portion 322 to translationally secure the first footplate 320 to the sleeve 90 such that the first footplate 320 and the sleeve 90 cannot translate relative to each other along the axis of rotation R.

The second footplate 420 includes a base portion 422 and an attachment portion 424. The base portion 422 defines a second opening 426 and a neck portion 428. As shown in the illustrated embodiment, the second opening 426 has a shape that corresponds to a shape of the shaft 40 of the screw 30. In one embodiment, the second opening 426 includes internal threads that correspond to the external threads 42 such that when the shaft 40 is inserted into the second opening 426, the screw 30 and the second footplate 420 are secured such that the screw 30 is rotatable relative to the second footplate 420 about the axis of rotation R, and vice versa.

As shown in the illustrated embodiment the ratchet 120 includes a ratchet body 122, the ratchet body 122 can have a first collar member 124, a ratchet tab 126, and a second collar member 128. In one embodiment, the ratchet 120 is configured to be secured to the distractor body 24: such that the screw 30, the sleeve 90, and the ratchet 120 are all translationally secured such that each of the screw 30, the sleeve 90, and the ratchet 120 cannot translate relative to the other two of the screw 30, the sleeve 90, and the ratchet 120 along the axis of rotation R. In another embodiment the ratchet 120 is rotationally secured to the sleeve 90 such that the ratchet 120 and the sleeve 90 cannot rotate relative to each other about the axis of rotation R, and the screw 30 is rotatable relative to both the ratchet 120 and the sleeve 90 about the axis of rotation R.

In one embodiment the ratchet 120 is configured to be secured to the distractor body 24 such that a portion of the ratchet 120 engages a portion of the screw 30. The interference of the portion of the ratchet 120 and the portion of the screw 30 restricts relative rotation of the ratchet 120 and the screw 30 such that a minimum torque value, referred to herein as a sufficient torque T, must be applied to the screw 30 to rotate the screw 30 relative to the ratchet 120, or vice versa, about the axis of rotation R.

In one embodiment the ratchet 120 and the screw 30 are configured such that the minimum torque value required to rotate the screw 30 relative to the ratchet 120 in the first direction of rotation R1, for example clockwise, is different than the minimum torque value required to rotate the screw 30 relative to the ratchet 120 in the second direction of rotation R2, for example counterclockwise. In another embodiment the ratchet 120 and the screw 30 are configured such that the minimum torque value required to rotate the screw 30 relative to the ratchet 120 in the first direction of rotation R1 is substantially the same as the minimum torque value required to rotate the screw 30 relative to the ratchet 120 in the second direction of rotation R2. In one embodiment rotation of the screw 30 relative to the sleeve 90 in the first direction of rotation R1 actuates the distractor 20 so as to distract the distractor 20, and rotation of the screw 30 relative to the sleeve 90 in the second direction actuates the distractor so as to contract the distractor 20.

As shown in the illustrated embodiment, the bone distraction system 10 can further include a securing collar member 300 that is configured to provide additional securement of the ratchet 120 to the distractor body 24 such that the ratchet 120 is prevented from translating relative to the distractor body 24 along the axis of rotation R. In one embodiment the securing collar member 300 is secured to the screw 30 such that the securing collar member 300 and the screw 30 are rotationally and translationally secured relative to each other such that the securing collar member 300 and the screw 30 cannot rotate relative to each other about the axis of rotation R or translate relative to each other along the axis of rotation R. As shown, the securing collar member 300 can be configured to translationally capture the ratchet 120 between the securing collar member 300 and the sleeve 90 with respect to the direction parallel to the axis of rotation R, for example the longitudinal direction L, while still permitting the screw 30 to rotate relative to the ratchet 120 about the axis of rotation R.

As shown in the illustrated embodiment, the bone distraction system 10 is configured to be assembled such that:

1) the screw 30 is translationally secured to the sleeve 90 by inserting the screw 30 into the sleeve borehole 98 of the sleeve 90 such that the first portion 34 of the screw 30 is positioned outside the sleeve borehole 98 and the second portion 36 of the screw 30 is positioned within the sleeve borehole 98; 2) the ratchet 120 is translationally and rotationally secured to the sleeve 90 relative to the axis of rotation R; 3) the ratchet 120 and the screw 30 are engaged such that the ratchet 120 restricts relative rotation of the ratchet 120 and the screw 30 about the axis of rotation R until a minimum torque value, for example the sufficient torque T, is applied to the screw 30; 4); the first footplate 320 is translationally and rotationally secured to the sleeve 90, relative to the axis of rotation R, by first inserting the outer surface 100 through the first opening 326, and second by inserting the securing screw 328 into the sleeve borehole 98; and 5) the second footplate 420 is secured to the screw 30 by inserting the shaft 40 through the second opening 426 and positioning the neck portion 428 of the second footplate 420 within the slot 104 of the sleeve 90.

Once the bone distraction system 10 has been assembled, for example as described above, the bone distraction system 10 can be used to adjust the distance D between the first footplate 320 and the second footplate 420 as described below. When the first footplate 320 is attached to the first bone segment 2a and the second footplate 420 is attached to the second bone segment 2b adjusting the distance D will also adjust the gap 3 between the first bone segment 2a and the second bone segment 2b.

The first footplate 320 is positioned along the shaft 40 of the screw 30 such that the first footplate 320 is separated from the second footplate 420 by the distance D. As shown in the illustrated embodiment the distance D is measured in the longitudinal direction, in a straight line, between a facing surface 330 of the attachment portion 324 of the first footplate 320 and a facing surface 430 of the attachment portion 424 of the second footplate 420. In another embodiment the distance D can be measured between other relative surfaces of the first footplate 320 and the second footplate 420.

Once the first footplate 320 has been spaced from the second footplate 420 by the selected distance D, the first footplate 320 is attached to the first bone segment 2a and the second footplate 420 is attached to the second bone segment 2b. One or more fasteners, including for example a bone screw, can be inserted through a hole 332 in the attachment portion 324 of the first footplate 320 to secure the first footplate 320 to the first bone segment 2a. One or more fasteners, including for example a bone screw, can also be inserted through a hole 432 in the attachment portion 424 of the second footplate 420 to secure the second footplate 420 to the second bone segment 2b.

When the second footplate 420 is secured to the screw 30 such that the shaft 40 is inserted through the second opening 426, the neck portion 428 extends through the slot 104 of the sleeve 90. The neck portion 428 is captured within the slot 104 such that the second footplate 420 can translate within the slot 104 along the axis of rotation R, but cannot rotate relative to the sleeve 90 about the axis of rotation R. Once the sufficient torque T is applied to the actuation mechanism 38 of the screw 30, the screw 30 rotates about the axis of rotation R relative to the rest of the bone distraction system 10 that is secured to the first bone segment 2a and the second bone segment 2b.

As the screw 30 rotates in the desired direction of rotation, the shaft 40 of the screw 30 rotates within the second opening 426 of the second footplate 420 causing the corresponding threads of the shaft 40 and the base portion 422 to interact. The interaction of the corresponding threads of the shaft 40 and the base portion 422 translates the second footplate 420 along the axis of rotation R within the slot 104 relative to the screw 30, the sleeve 90, and the first footplate 320. As the second footplate 420 translates relative to the first footplate 320, the distance D between the first footplate 320 and the second footplate 420 is adjusted. Adjustment of the distance D between the first footplate 320 and the second footplate 420 adjusts the size of the gap 3 between the first bone segment 2a and the second bone segment 2b.

Referring to FIGS. 3A-3C, the distractor 20 according to one embodiment, is constructed so as to include a screw 30 and a sleeve 90 that are configured to be connected to each other such that the screw 30 is rotatable relative to the sleeve 90 about the axis of rotation R, and vice versa.

As shown in the illustrated in embodiment, the screw 30 is elongate along a screw axis 44. The screw 30 defines a first end 46 and a second end 48 spaced from the first end 46 along the screw axis 44 in a first direction. The screw body 32 extends from the first end 46 to the second end 48. In one embodiment the screw body 32 can include a first portion 34 and a second portion 36. As shown, the first portion 34 extends from the first end 46 toward the second end 48, and the second portion 36 extends from the second end 48 toward the first end 46. In one embodiment the first portion 34 extends from the first end 46 to the second portion 36, and the second portion 36 extends from the second end 48 to the first portion 34.

The first portion 34 includes an actuation mechanism 38 that is configured to receive a torque T that rotates the screw 30 about an axis of rotation R. As shown in the illustrated embodiment, the axis of rotation R can be the screw axis 44. The first portion 34 can further include a shoulder portion 50, the shoulder portion 50 including an abutment surface 52. The abutment surface 52 faces the second end 48 of the screw 30, and the abutment surface defines an outer dimension D1 measured in a direction perpendicular to the axis of rotation R along a straight line that passes through the axis of rotation R. As shown, the shoulder portion 50 and abutment surface 52 each define a circular shape such that the outer dimension D1 is a diameter. In another embodiment the shoulder portion 50 and abutment surface 52 each define a non-circular shape.

Referring to FIGS. 2A-2B and 3A, the screw 30 further includes a third portion 54 that includes at least one ratchet engagement structure 56. The ratchet engagement structure 56 is configured to engage the ratchet 120 such that interference between the ratchet 120 and the third portion 54 of the screw 30 restricts relative rotation of the ratchet 120 and the screw 30 such that a minimum torque value, for example the sufficient torque T, must be applied to the screw 30, to rotate the screw 30 relative to the ratchet 120, or vice versa, about the axis of rotation R.

As shown in the illustrated embodiment, the third portion 54 can be disposed within the first portion 34 such that when the screw 30 and sleeve 90 are assembled to form the distractor 20, the third portion 54 is positioned outside the sleeve borehole 98 of the sleeve 90. In another embodiment the third portion 54 can be disposed within the second portion 36 such that when the screw 30 and sleeve 90 are assembled to form the distractor 20, the third portion 54 is positioned inside the sleeve borehole 98 of the sleeve 90. In yet another embodiment the third portion 54 can be disposed between the first portion 34 and the second portion 36 such that when the screw 30 and sleeve 90 are assembled to form the distractor 20, the third portion 54 is positioned partially inside the sleeve borehole 98 and partially outside the sleeve borehole 98.

Referring to FIGS. 3A-3F, in one embodiment the ratchet engagement structure 56 includes at least one recess 58 that extends into the screw body 32 toward the screw axis 44. In another embodiment the ratchet engagement structure 56 can include a plurality of recesses 58 that are radially spaced about the screw axis 44 from adjacent ones of the plurality of recesses 58 by an angle α (alpha).

As shown in the illustrated embodiment, the ratchet engagement structure 56 includes eight recesses 58, each of the recesses 58 being equidistantly spaced about 45° from adjacent ones of the recesses 58. In another embodiment the plurality of recesses 58 can include from between one and twelve recesses 58. In another embodiment the angle α (alpha) between adjacent ones of the plurality of recesses 58 can vary such that each of the plurality of recesses 58 is not equidistantly spaced from adjacent ones of the plurality of recesses 58. In yet another embodiment the ratchet engagement structure 56 includes projections that extend out from the screw body 32 away from the screw axis 44.

As shown in the illustrated embodiment, the at least one recess 58 (hereinafter "the recess 58") extends into an outer surface 60 of the screw body 32 in a direction toward the screw axis 44, and the recess 58 terminates at a base surface 62 of the screw body 32 such that the base surface 62 at least partially defines the recess 58. The base surface 62 includes a first end wall 64 and a second end wall 66 that is spaced from the first end wall 64 in the longitudinal direction L so as to define a recess length RL. The base surface 62 further includes a first side wall 68 and a second side wall 70, the first side wall 68 and the second side wall 70 each extend between the first end wall 64 and the second end wall 66. The second side wall 70 is spaced from the first side wall 68 in a radial direction with respect to the screw axis 44 so as to define a recess width RW. The base surface 62, as shown, further includes an apex 72 that is a portion of the base surface 62 that is closest to the screw axis 44. The apex 72 is spaced from the outer surface 60 in the transverse direction N so as to define a recess depth RD.

In one embodiment the base surface 62 further includes a first side edge 74 and a second side edge 76 spaced from the first side edge 74 in the radial direction with respect to the screw axis 44. As shown in the illustrated embodiment, the first side edge 74 can be formed at an intersection of the first side wall 68 and the outer surface 60, and the second side edge 76 can be formed at an intersection of the second side wall 70 and the outer surface 60.

In one embodiment the screw 30 can be constructed such that the recess length RL is between about 0.5 mm to about 5 mm. In another embodiment the screw 30 can be constructed such that the recess width RW is between about 0.05 mm to about 1.5 mm. In another embodiment the screw 30 can be constructed such that the recess depth RD is between about 0.05 mm to about 1 mm. In another embodiment the screw 30 can be constructed such that the recess length RL is between about 1.5 mm to about 3 mm, the recess width RW is between about 0.4 mm to about 0.6 mm, and the recess depth RD is between about 0.3 mm and about 0.4 mm.

Referring again to FIGS. 3A-3C, the sleeve 90 is configured to receive the screw 30, such that the screw 30 and sleeve 90 are rotatable relative to each other about the axis of rotation R. As shown in the illustrated embodiment, the sleeve body 96 is a tubular member and the sleeve borehole 98 extends through the sleeve body 96 between the first end 92 and the second end 94 along the longitudinal direction L, such that the sleeve 90 is elongate along a sleeve axis 99. The sleeve borehole 98 is at least partially defined by the inner surface 102 of the sleeve body 96. In one embodiment the sleeve borehole 98 can include a first opening 106 proximate the first end 92 such that the sleeve borehole 98 is open to the first end 92 of the sleeve 90. In another embodiment, the sleeve borehole 98 can include a second opening 108 proximate the second end 94 such that the sleeve borehole 98 is open to the second end 94 of the sleeve 90.

The sleeve body 96 can further include an abutment surface 110 that at least partially defines the first opening 106. As shown in the illustrated embodiment, the abutment surface 110 is configured to face the abutment surface 52 of the screw 30 when the screw 30 is inserted into the sleeve 90. The first opening 106 defines an outer dimension D2 that is measured along a straight line that passes through the sleeve axis 99 and is perpendicular to the sleeve axis 99. In one embodiment the first opening 106 is circular in shape such that the outer dimension D2 is a diameter. In another embodiment the first opening 106 is non-circular in shape. The second opening 108 defines an outer dimension D3 measured along a straight line that passes through the sleeve axis 99 and is perpendicular to the sleeve axis 99.

In one embodiment the sleeve 90 includes a slot 104 that is configured to receive a footplate, such as the second footplate 420 (as shown in FIGS. 2A-2B). The sleeve body 96 can include a first sleeve side wall 112 and a second sleeve side wall 114 that collectively at least partially define the slot 104. The second sleeve side wall 114 is spaced from the first sleeve side wall 112, for example in the lateral direction A, such that a slot width SW is defined. The first sleeve side wall 112 and the second sleeve side wall 114 each extend between the first end 92 and the second end 94 so as to define the slot length SL. In one embodiment, the slot 104 is open to or passes through the second end 94 and is closed to or terminates prior to passing through the first end 92.

The first sleeve side wall 112 and the second sleeve side wall 114 can each extend between the outer surface 100 and the inner surface 102, for example in the transverse direction N, so as to define a slot depth SD. In one embodiment, the first sleeve side wall 112 and the second sleeve side wall 114 each extend from the outer surface 100 to the inner surface 102 such that the slot depth SD extends through the sleeve body 96 and into the sleeve borehole 98 such that the sleeve borehole 98 is open to the exterior of the sleeve 90 through the slot 104.

According to one embodiment, the distractor 20 is configured to be assembled such that the second portion 36 of the screw 30 is positioned within the sleeve borehole 98, and the first portion 34 is positioned outside the sleeve borehole 98. As shown in the illustrated embodiment, the shaft 40 defines an outer dimension D4, for example an outer diameter, that is less than the outer dimension D2 of the first opening 106, allowing the shaft 40 to be inserted through the first opening 106, into the sleeve borehole 98. The shaft 40 is inserted in a direction toward the second end 94 of the sleeve 90 until the abutment surface 52 of the screw 30 comes into contact with the abutment surface 110 of the sleeve 90. In one embodiment, the outer dimension D1 of the abutment surface 52 is greater than the outer dimension D2 of the first opening 106 such that interference between the abutment surface 52 of the screw 30 and the abutment surface 110 of the sleeve 90 prevent further insertion of the screw 30 into the sleeve 90. Alternatively, the shaft 40 can be inserted in a direction toward the second end 94 of the sleeve 90 until the abutment surface 52 of the screw body 32 and the abutment surface 110 of the sleeve 90 each contacts an intermediate surface positioned between the abutment surface 52 of the screw 30 and the abutment surface 110 of the sleeve 90.

Referring to FIGS. 4A-4D, in one embodiment, the ratchet 120 includes a first end 130, a second end 132 spaced from the first end 130 in a direction, for example the longitudinal direction L, and a ratchet body 122 extending from the first end 130 to the second end 132. The ratchet 120 defines a ratchet borehole 134 that extends through the ratchet body 122 from the first end 130 to the second end 132 along a ratchet axis 136. As shown, the ratchet axis 136 can be positioned centrally within the ratchet borehole 134.

Referring to FIGS. 2A-2B and 4A-4C, according to one embodiment, the ratchet body 122 includes a ratchet tab 126 that is configured to be connected to the distractor 20 such that the ratchet tab 126 is translationally and rotationally secured to the sleeve 90 such that translation of the ratchet 120 along the axis of rotation R relative to the sleeve 90 and rotation of the ratchet 120 about the axis of rotation R relative to the sleeve 90 are both prevented. Additionally, the ratchet tab 126 is translationally secured and rotatable relative to the screw 30 such that translation of the ratchet 120 along the axis of rotation R relative to the screw 30 is prevented, but rotation of the ratchet 120 about the axis of rotation R relative to the screw 30 is permitted.

Referring to FIG. 4A-4D, the ratchet tab 126 includes a first end 138, a second end 140 spaced from the first end 138 along a first direction, for example the longitudinal direction L, and a ratchet tab body 142 that extends from the first end 138 to the second end 140 along the ratchet axis 136. The ratchet borehole 134 extends through the ratchet tab body 142 from the first end 138 of the ratchet tab 126 to the second end 140 of the ratchet tab 126. As shown in the illustrated embodiment, the ratchet tab body 142 can include an inner surface 144 that faces the ratchet axis 136 and at least partially defines the ratchet borehole 134. As shown, the ratchet tab body 142 can further include an outer surface 146 that faces opposite the inner surface 144 of the ratchet tab body 142.

Figure 4A:
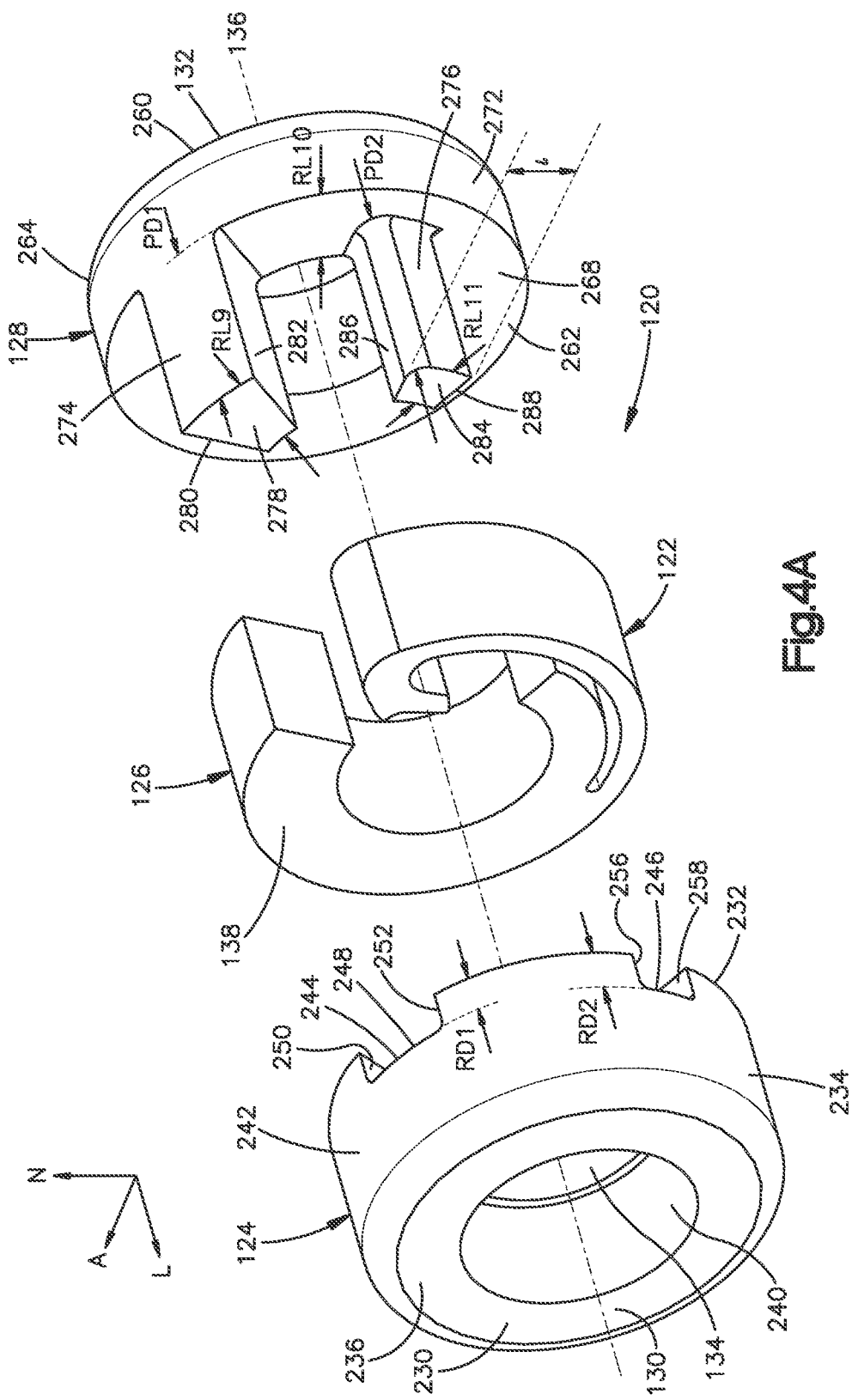
FIG. 4A is an exploded perspective view of the ratchet illustrated in FIG. 2A, the ratchet including a first collar member, a ratchet tab, and a second collar member.
Figure 4B:
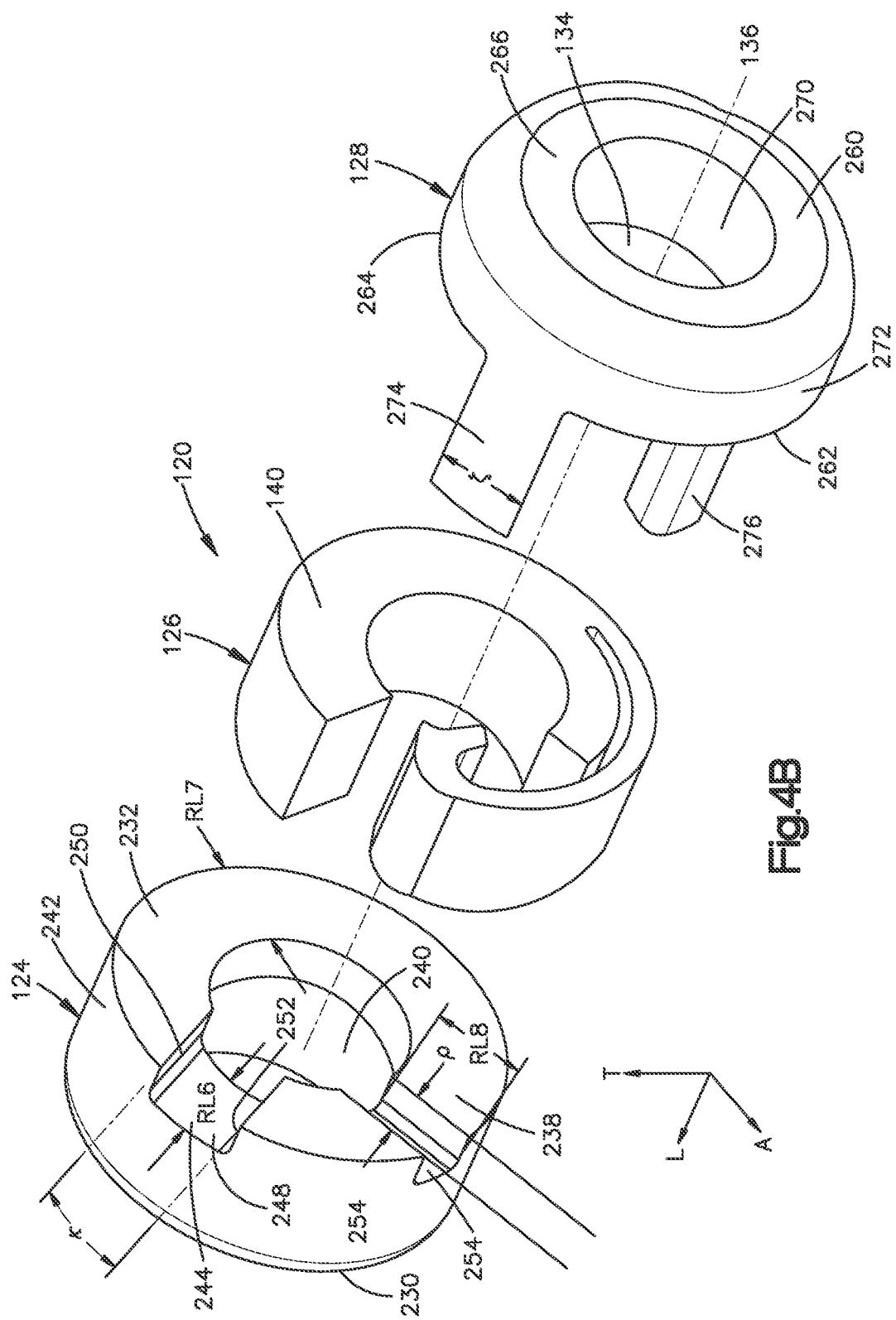
FIG. 4B is another exploded perspective view of the ratchet illustrated in FIG. 4A.
Figure 4C:
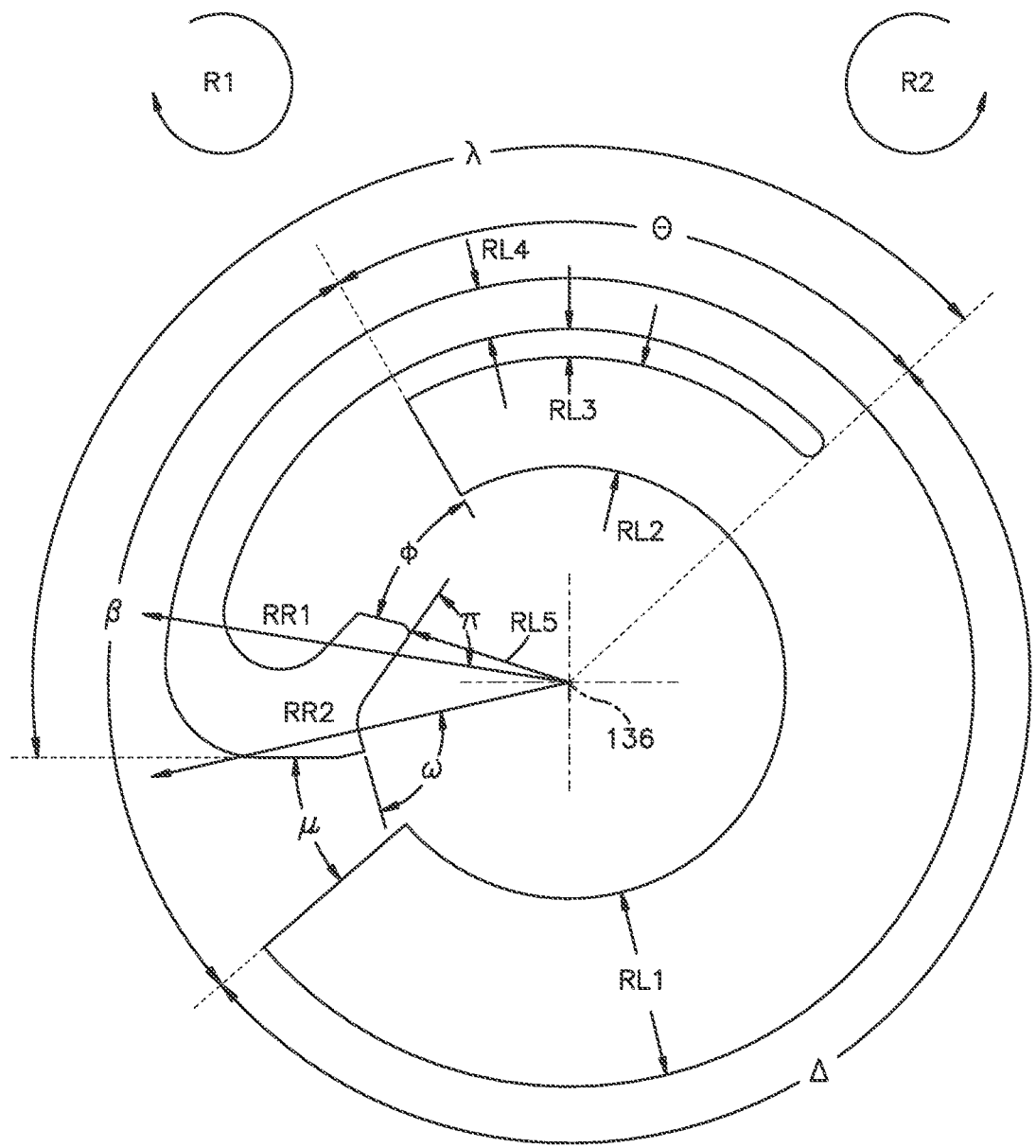
FIG. 4C is a front view of the ratchet tab illustrated in FIG. 4A.
Figure 4D:
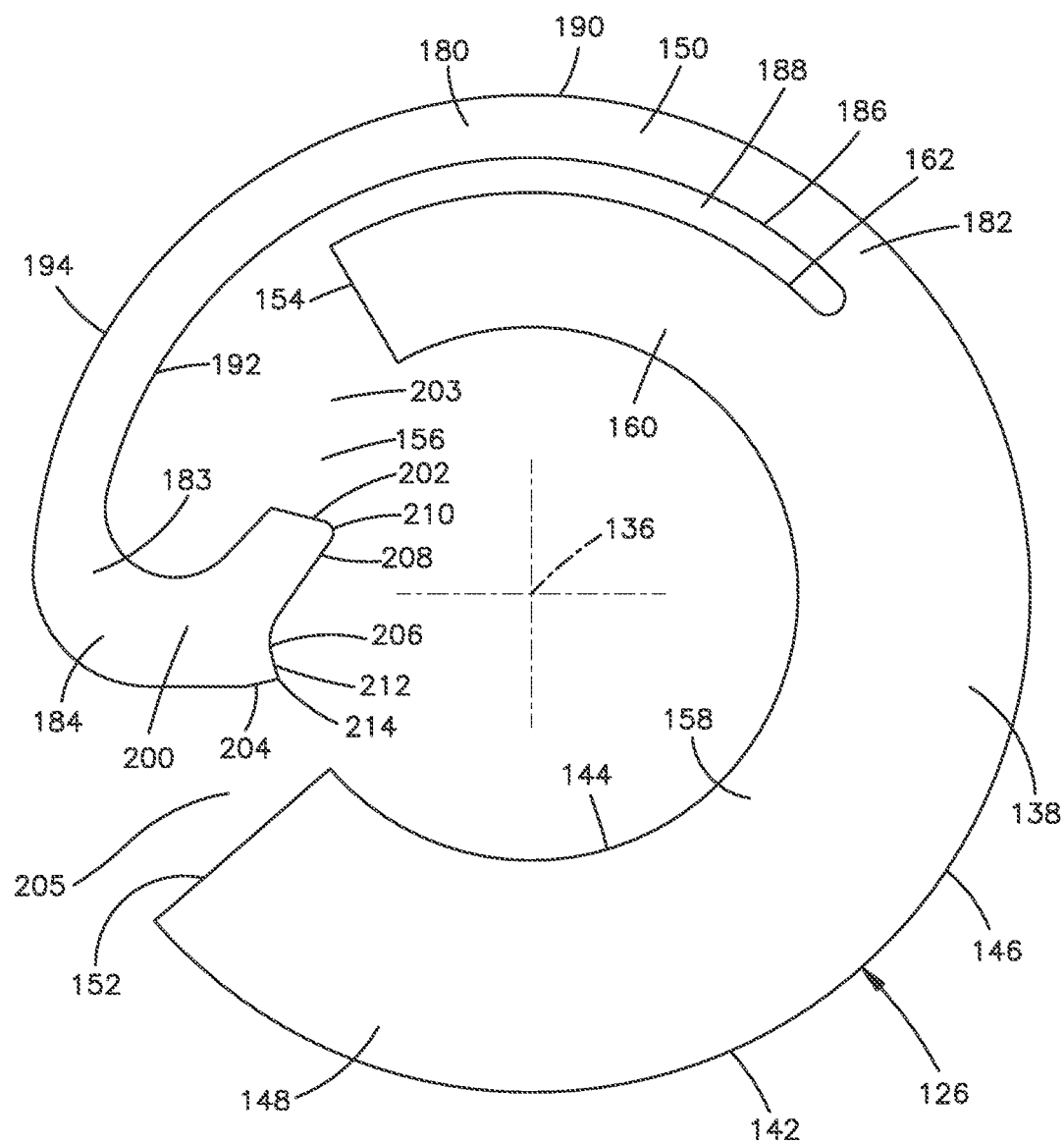
FIG. 4D is a front view of the ratchet tab illustrated in FIG. 4C.

Referring to FIGS. 4C-4D, the ratchet tab body 142 can be constructed, according to one embodiment, to include a base portion 148 and a boom arm portion 150. The base portion 148 includes a first surface 152 that faces in a first direction of rotation R1 about the ratchet axis 136 and a second surface 154 that faces in a second direction of rotation R2 about the ratchet axis 136. In one embodiment, the second direction of rotation R2 is opposite the first direction of rotation R1 with respect to the ratchet axis 136. In another embodiment, the first direction of rotation R1 is clockwise and the second direction of rotation R2 is counterclockwise. The first surface 152 and the second surface 154 are angularly spaced apart so as to define an angular gap 156 between the first surface 152 and the second surface 154. The angular gap 156 defines an angular length β (beta) about the ratchet axis 136 that can be described in terms of an angle measured between the first surface 152 and the second surface 154 about the ratchet axis 136. According to one embodiment, the ratchet tab body 142 can be constructed such that the first surface 152 is spaced from the second surface 154 by the angular gap 156 such that the angular length β (beta) is between about 75° and about 125°. In another embodiment the angular gap 156 defines an angular length β (beta) of about 100°.

The base portion 148 can further include a main portion 158 and an extension portion 160. The main portion 158 extends angularly about the ratchet axis 136 from the first surface 152 to the extension portion 160 so as to define an angular length Δ (delta), and the extension portion 160 extends angularly about the ratchet axis 136 from the main portion 158 to the second surface 154 so as to define an angular length θ (theta). The main portion 158 extends in the radial direction from the inner surface 144 to the outer surface 146 so as to define a radial length RL1.

In one embodiment, the angular length Δ (delta) is between about 135° and about 195°. In another embodiment, the angular length Δ (delta) is about 185°. In another embodiment, the angular length θ (theta) is between about 65° and about 125°. In another embodiment, the angular length θ (theta) is about 95°. In another embodiment the radial length RL1 is between about 0.5 mm and about 1.5 mm. In another embodiment the radial length RL1 is about 1.0 mm.

The extension portion 160 includes an intermediate outer surface 162 that extends angularly between the main portion 158 and the second surface 154, for example from the main portion 158 to the second surface 154. The intermediate outer surface 162 is positioned between the inner surface 144 and the outer surface 146 with respect to the radial direction such that the extension portion 160 defines a radial length RL2 that is less than the radial length RL1 of the main portion 158.

The boom arm portion 150, according to one embodiment, includes a boom arm body 180 that has a fulcrum portion 182 and a distractor body engagement structure 183. As shown in the illustrated embodiment, the distractor body engagement structure 183 can include a tip portion 184 that is configured to engage the ratchet engagement structure 56 of the screw 30. The fulcrum portion 182 is attached to the main portion 158. As shown in the illustrated embodiment, the fulcrum portion 182 can be monolithic, or a single integral piece, with the main portion 158. In another embodiment, the fulcrum portion 182 and the main portion 158 can be releasably attached. The boom arm portion 150 extends angularly about the ratchet axis 136 from the main portion 158 to the tip portion 184 so as to define an angular length λ (lambda). As shown in the illustrated embodiment, the tip portion 184 can be positioned within the angular gap 156 between the first surface 152 and the second surface 154 with respect to the angular direction. In one embodiment the angular length λ (lambda) is between about 120° and about 200°. In another embodiment, the angular length λ (lambda) is about 145°.

According to one embodiment, the fulcrum portion 182 includes an intermediate inner surface 186 that faces the intermediate outer surface 162 and is spaced from the intermediate outer surface 162 by a radial gap 188 that defines a radial length RL3. The fulcrum portion 182 further includes an outer surface 190 that is opposite the intermediate inner surface 186 so as to define a radial length RL4 of the fulcrum portion 182. In one embodiment the combined radial length of the radial lengths RL2, RL3, and RL4 along the same radial ray equals the radial length RL1. In another embodiment the radial length RL3 is about 0.1 mm to about 1.1 mm and the radial length RL4 is about 0.05 mm to about 0.35 mm. In another embodiment the radial length RL3 is about 0.15 mm and the radial length RL4 is about 0.25 mm.

The tip portion 184 includes an inner surface 192 that faces the ratchet axis 136 and an outer surface 194 spaced from the inner surface 192. The tip portion 184 further includes a pawl portion 200 configured to engage the ratchet engagement structure 56 of the screw 30. In one embodiment, the pawl portion 200 can include a first pawl surface 202 that faces in the first direction of rotation R1. As shown in the illustrated embodiment, the first pawl surface 202 is spaced from the second surface 154 of the base portion 148 by a gap 203 that defines an angular length Φ (phi). In one embodiment the ratchet tab 126 defines an angular length Φ (phi) of between about 15° and about 75°. In another embodiment, the ratchet tab 126 defines an angular length Φ (phi) of about 45°.

The pawl portion 200 can further include a second pawl surface 204 that faces in the second direction of rotation R2. As shown in the illustrated embodiment, the second pawl surface 204 is spaced from the first surface 152 of the base portion 148 by a gap 205 that defines an angular length μ (mu). In one embodiment the ratchet tab 126 defines an angular length μ (mu) of between about 10° and about 55°. In another embodiment, the ratchet tab 126 defines an angular length μ (mu) of about 25°.

In one embodiment, the pawl portion 200 can include an inner pawl surface 206 that extends radially between the first pawl surface 202 and the second pawl surface 204, for example from the first pawl surface 202 to the second pawl surface 204. The inner pawl surface 206, as shown, can include a first portion 208 that defines an angle π (pi) with respect to a radial ray RR1. As shown in the illustrated embodiment, the radial ray RR1 extends from the ratchet axis 136 along a straight line that is perpendicular to the ratchet axis 136 and intersects the first portion 208 at the angle π (pi). In one embodiment the ratchet tab 126 can be constructed so as to define an angle π (pi) of between about 20° and about 80°. In another embodiment, the ratchet tab 126 defines an angle π (pi) of about 50°.

According to the illustrated embodiment, the pawl portion 200 can further include an intersection 210 of the first pawl surface 202 and the first portion 208. As shown the intersection 210 can define a radial length RL5 from the ratchet axis 136 that is less than the radial length of any other surface of the ratchet tab body 142. The inner pawl surface 206 can further include a second portion 212 that defines an angle ω (omega) with respect to a radial ray RR2. As shown in the illustrated embodiment, the radial ray RR2 extends from the ratchet axis 136 along a straight line that is perpendicular to the ratchet axis 136 and intersects the second portion 212 at the angle ω (omega). According to the illustrated embodiment, the pawl portion 200 can further include an intersection 214 of the second pawl surface 204 and the second portion 212. In one embodiment the ratchet tab 126 can be constructed so as to define an angle ω (omega) of between about 110° and about 70°. In another embodiment, the ratchet tab 126 defines an angle ω (omega) of about 90°.

Referring to FIGS. 4A-4D, in one embodiment, the ratchet 120 can include at least one collar member, for example a first collar member 124 and a second collar member 128, configured to secure the ratchet tab 126 to the distractor 20 such that 1) the ratchet tab 126 is translationally and rotationally secured to the sleeve 90 relative to the axis of rotation R; and 2) the ratchet tab 126 is translationally secured and rotatable relative to the screw 30 with respect to the axis of rotation R.

As shown in the illustrated embodiment, the first collar member 124 can include a first end 230, a second end 232 spaced from the first end 230 along a first direction, for example the longitudinal direction L, and a first collar member body 234 that extends from the first end 230 to the second end 232 along the ratchet axis 136. The first collar member body 234 includes a first end surface 236 and a second end surface 238. As shown, the first end surface 236 is proximate the first end 230, and the second end surface 238 is opposite the first end surface 236 and is proximate the second end 232.

In one embodiment, the ratchet borehole 134 can extend through the first collar member body 234 from the first end 230 of the first collar member 124 to the second end 232 of the first collar member 124. In one embodiment, the first collar member body 234 can include an inner surface 240 that faces the ratchet axis 136 and at least partially defines the ratchet borehole 134. As shown, the first collar member body 234 can further include an outer surface 242 that is radially spaced from the inner surface 240 and faces opposite the inner surface 240.

The first collar member 124 can further include at least one recess, for example a first recess 244 and a second recess 246. As shown in the illustrated embodiment, the first recess 244 extends into the second end surface 238 of the first collar member body 234 in a direction, for example the longitudinal direction L, toward the first end surface 236 so as to define a first recess depth RD1. In one embodiment, the first collar member body 234 includes a first base surface 248 positioned between the first end surface 236 and the second end surface 238 with respect to the longitudinal direction L such that the first recess 244 terminates at first base surface 248. In one embodiment the first base surface 248 is substantially flat. In another embodiment the first base surface 248 is not flat, for example substantially curved.

The first recess 244 extends between the inner surface 240 and the outer surface 242 in the radial direction so as to define a radial length RL6. As shown in the illustrated embodiment, the first recess 244 can extend from the inner surface 240 to the outer surface 242 such that the radial length RL6 of the first recess 244 is the same as a radial length RL7 of the first collar member 124. In another embodiment the radial length RL6 of the first recess 244 is less than the radial length RL7 of the first collar member 124.

As shown in the illustrated embodiment, the first collar member body 234 can further include a first side wall 250 and a second side wall 252 that is spaced from the first side wall 250 with respect to an angular direction centered on the ratchet axis 136. The first side wall 250 and the second side wall 252 each: 1) extend between the inner surface 240 and the outer surface 242 in the radial direction; and 2) also extend between the second end surface 238 and the first base surface 248. The first recess 244 extends between the first side wall 250 and the second side wall 252 so as to define an angular length κ (kappa).

As shown in the illustrated embodiment, the second recess 246 can extend into the second end surface 238 of the first collar member body 234 in a direction, for example the longitudinal direction L, toward the first end surface 236 so as to define a second recess depth RD2. In one embodiment, the first collar member body 234 includes a second base surface 254 positioned between the first end surface 236 and the second end surface 238 with respect to the longitudinal direction L such that the second recess 246 terminates at second base surface 254. In one embodiment the second base surface 254 is substantially flat. In another embodiment the second base surface 254 is not flat, for example substantially curved.

The second recess 246 extends between the inner surface 240 and the outer surface 242 in the radial direction so as to define a radial length RL8. As shown in the illustrated embodiment, the second recess 246 can extend from the inner surface 240 to the outer surface 242 such that the radial length RL8 of the second recess 246 is the same as the radial length RL7 of the first collar member 124. In another embodiment the radial length RL8 of the second recess 246 is less than the radial length RL7 of the first collar member 124.

As shown in the illustrated embodiment, the first collar member body 234 can further include a third side wall 256 and a fourth side wall 258 that is spaced from the third side wall 256 with respect to an angular direction centered on the ratchet axis 136. The third side wall 256 and the fourth side wall 258 each: 1) extend between the inner surface 240 and the outer surface 242 in the radial direction; and 2) also extend between the second end surface 238 and the second base surface 254. The second recess 246 extends between the third side wall 256 and the fourth side wall 258 so as to define an angular length ρ (rho).

The second collar member 128 of the ratchet 120, according to one embodiment, is constructed similarly to the first collar member 124 except that instead of defining recesses the second collar member 128 includes projections. As shown in the illustrated embodiment, the second collar member 128 can include a first end 260, a second end 262 spaced from the first end 260 along a first direction, for example the longitudinal direction L, and a second collar member body 264 that extends from the first end 260 to the second end 262 along the ratchet axis 136. The second collar member body 264 includes a first end surface 266 and a second end surface 268. As shown, the first end surface 266 is proximate the first end 260, and the second end surface 268 is opposite the first end surface 266 and is proximate the second end 262.

In one embodiment, the ratchet borehole 134 can extend through the second collar member body 264 from the first end 260 of the second collar member 128 to the second end 262 of the second collar member 128. In one embodiment, the second collar member body 264 can include an inner surface 270 that faces the ratchet axis 136 and at least partially defines the ratchet borehole 134. As shown, the second collar member body 264 can further include an outer surface 272 that is radially spaced from the inner surface 270 and faces opposite the inner surface 270.

The second collar member 128 can further include at least one projection, for example a first projection 274 and a second projection 276. As shown in the illustrated embodiment, the first projection 274 extends out from the second end surface 268 of the second collar member body 264 in a direction, for example the longitudinal direction L, away from the first end surface 266 so as to define a first projection depth PD1. In one embodiment, the second collar member 128 includes a first tip surface 278 positioned outside (or not between) the first end surface 266 and the second end surface 268 with respect to the longitudinal direction L such that the first projection 274 terminates at first tip surface 278. In one embodiment the first tip surface 278 corresponds in shape to the first base surface 248. In another embodiment the first tip surface 278 is substantially flat. In another embodiment the first tip surface 278 is not flat, for example substantially curved.

The first projection 274 extends between the inner surface 270 and the outer surface 272 with respect to the radial direction so as to define a radial length RL9. As shown in the illustrated embodiment, the first projection 274 can extend from the inner surface 270 to the outer surface 272 such that the radial length RL9 of the first projection 274 is the same as a radial length RL10 of the second collar member 128. In one embodiment the radial length RL9 of the first projection 274 corresponds to the radial length RL6 of the first recess 244. In another embodiment the radial length RL9 of the first projection 274 is less than the radial length RL10 of the second collar member 128.

As shown in the illustrated embodiment, the first projection 274 can further include a first side wall 280 and a second side wall 282 that is spaced from the first side wall 280 with respect to an angular direction centered on the ratchet axis 136. The first side wall 280 and the second side wall 282 each: 1) extend between the inner surface 270 and the outer surface 272 in the radial direction; and 2) also extend between the second end surface 268 and the first tip surface 278. The first projection 274 extends between the first side wall 280 and the second side wall 282 so as to define an angular length ζ (zeta).

As shown in the illustrated embodiment, the second projection 276 can extend out from the second end surface 268 of the second collar member body 264 in a direction, for example the longitudinal direction L, away from the first end surface 266 so as to define a second projection depth PD2. In one embodiment, the second collar member 128 includes a second tip surface 284 positioned outside (or not between) the first end surface 266 and the second end surface 268 with respect to the longitudinal direction L such that the second projection 276 terminates at second tip surface 284. In one embodiment the second tip surface 284 corresponds in shape to the second base surface 254. In another embodiment the second tip surface 284 is substantially flat. In another embodiment the second tip surface 284 is not flat, for example substantially curved.

The second projection 276 extends between the inner surface 270 and the outer surface 272 in the radial direction so as to define a radial length RL11. As shown in the illustrated embodiment, the second projection 276 can extend from the inner surface 270 to the outer surface 272 such that the radial length RL11 of the second projection 276 is the same as the radial length RL10 of the second collar member 128. In another embodiment the radial length RL11 of the second projection 276 is less than the radial length RL10 of the second collar member 128.

As shown in the illustrated embodiment, the second projection 276 can further include a third side wall 286 and a fourth side wall 288 that is spaced from the third side wall 286 with respect to an angular direction centered on the ratchet axis 136. The third side wall 286 and the fourth side wall 288 each: 1) extend between the inner surface 270 and the outer surface 272 in the radial direction; and 2) also extend between the second end surface 268 and the second tip surface 284. The second projection 276 extends between the third side wall 286 and the fourth side wall 288 so as to define an angular length κ (iota).

The ratchet 120, in accordance with one embodiment, is configured to be assembled as described below. The first collar member 124, the ratchet tab 126, and the second collar member 128 are aligned such that the inner surfaces 240, 144, and 270 collectively define the ratchet borehole 134. The first collar member 124, the ratchet tab 126, and the second collar member 128 are further aligned such that the first recess 244, the gap 205, and the first projection 274 are aligned. Additionally, the first collar member 124, the ratchet tab 126, and the second collar member 128 are further aligned such that the second recess 246, the gap 203, and the second projection 276 are aligned. The ratchet 120 is further configured such that translation of the first collar member 124 toward the first end 138 of the ratchet tab 126 and translation of the second collar member 128 toward the second end 140 of the ratchet tab 126 results in the insertion of the first projection 274 through the gap 205 and into the first recess 244. The translation of the first collar member 124 toward the first end 138 of the ratchet tab 126 and translation of the second collar member 128 toward the second end 140 of the ratchet tab 126 further results in the insertion of the second projection 276 through the gap 203 and into the second recess 246.

Assembly of the ratchet 120 as described above, results in the first collar member 124, the ratchet tab 126, and the second collar member 128 being rotationally secured relative to each other with respect to the ratchet axis 136.

Referring to FIGS. 4A-5C, in accordance with one embodiment, the bone distraction system 10 includes the distractor 20 and the ratchet 120 assembled as described below. The shaft 40 of the screw 30 is inserted through the first opening 106 of the sleeve borehole 98 until the abutment surface 52 of the screw 30 comes into contact with the abutment surface 110 of the sleeve 90. When the abutment surface 52 of the screw 30 contacts the abutment surface 110 of the sleeve 90, the first portion 34 of the screw 30 is positioned at least partially outside the sleeve borehole 98 and the second portion 36 of the screw is positioned at least partially within the sleeve borehole 98.

According to one embodiment, the ratchet 120 is configured to be attached to the distractor 20 by inserting the first portion 34 of the screw 30 through the ratchet borehole 134 until the ratchet 120 contacts the abutment surface 110 of the sleeve 90. As shown in the illustrated embodiment, the first end 230 of the first collar member 124 abuts the abutment surface 110 of the sleeve 90. The ratchet 120 can then be secured to the sleeve 90 such that the ratchet 120 and sleeve 90 are rotationally and translationally secured relative to one another with respect to the axis of rotation R. For example, the first end surface 236 of the first collar member 124 can be welded to the abutment surface 110 of the sleeve 90. In another embodiment the ratchet 120 and sleeve 90 can be attached by other means.

As shown in the illustrated embodiment, the ratchet 120 can include a shoulder portion 290. The shoulder portion 290 is configured to capture the shoulder portion 50 of the screw 30 between the abutment surface 110 of the sleeve 90 and the shoulder portion 290 of the ratchet 120, with respect to the longitudinal direction L, once the ratchet 120 has been secured to the sleeve 90 as described above. In one embodiment, the shoulder portion 290 is defined by the first collar member 124, however in another embodiment the shoulder portion 290 can be defined within either the ratchet tab 126 or the second collar member 128.

In one embodiment the bone distraction system 10 can include a securing collar member 300 that is configured to further secure the ratchet 120 to the distractor 20. As shown in the illustrated embodiment, the securing collar member 300 includes a securing collar body 302 and a securing collar borehole 304 that extends through the securing collar body 302.

Subsequent to the first portion 34 of the screw 30 being inserted through the ratchet borehole 134, the securing collar member 300 can be attached to the distractor 20 by inserting the first portion 34 of the screw 30 through the securing collar borehole 304 such that at least a portion of the ratchet 120, for example an entirety of the ratchet 120, is captured between the sleeve 90 and the securing collar member 300, thus translationally securing the first collar member 124, the ratchet tab 126, and the second collar member 128 relative to each other with respect to the axis of rotation R.

The securing collar member 300 can then be secured to the screw 30, either permanently, for example by welding the securing collar body 302 to the first portion 34, or releasably, for example by threadedly engaging the securing collar body 302 to the first portion 34. As shown in the illustrated embodiment, the first portion 34 of the screw 30 can be inserted through the securing collar borehole 304 until the securing collar member 300 abuts the ratchet 120, for example the first end surface 266 of the second collar member 128.

In accordance with one embodiment, the bone distraction system 10 defines an assembled configuration in which: 1) the ratchet 120 is both translationally secured and rotationally secured to the sleeve 90 such that the ratchet 120 cannot translate along or rotate about the axis of rotation R relative to the sleeve 90; 2) the screw 30 is translationally secured relative to the sleeve 90 such that the screw 30 cannot translate relative to the sleeve 90 with respect to the axis of rotation R; 3) the screw 30 is rotatable relative to both the sleeve 90 and the ratchet 120 with respect to the axis of rotation R. In one embodiment when the bone distraction system 10 is in the assembled configuration: 4) the screw 30 is translationally secured relative to the ratchet 120 with respect to the axis of rotation R.

Referring to FIGS. 6A-6D, when the bone distraction system 10 is in the assembled configuration the distractor 20 can be actuated to rotate the screw 30 relative to the ratchet 120 about the axis of rotation R. The ratchet 120 is configured to engage the screw 30 such that rotation of the screw 30 in a first direction of rotation R1 is prevented until a first minimum torque value, for example the sufficient torque T, is applied to the actuation mechanism 38 of the screw 30. The ratchet 120 is further configured to engage the screw 30 such that rotation of the screw 30 in a second direction of rotation R2 is prevented until a second minimum torque value, for example the sufficient torque T', is applied to the actuation mechanism 38 of the screw 30.

In one embodiment the first minimum torque value is different than the second minimum torque value. In another embodiment the second minimum torque value is greater than the first minimum torque value. In another embodiment the second minimum torque value is less than the first minimum torque value. In another embodiment the second minimum torque value is at least five times greater than the first minimum torque value. In another embodiment the second minimum torque value is between about five times and about twenty times the first minimum torque value.

Figure 6A:
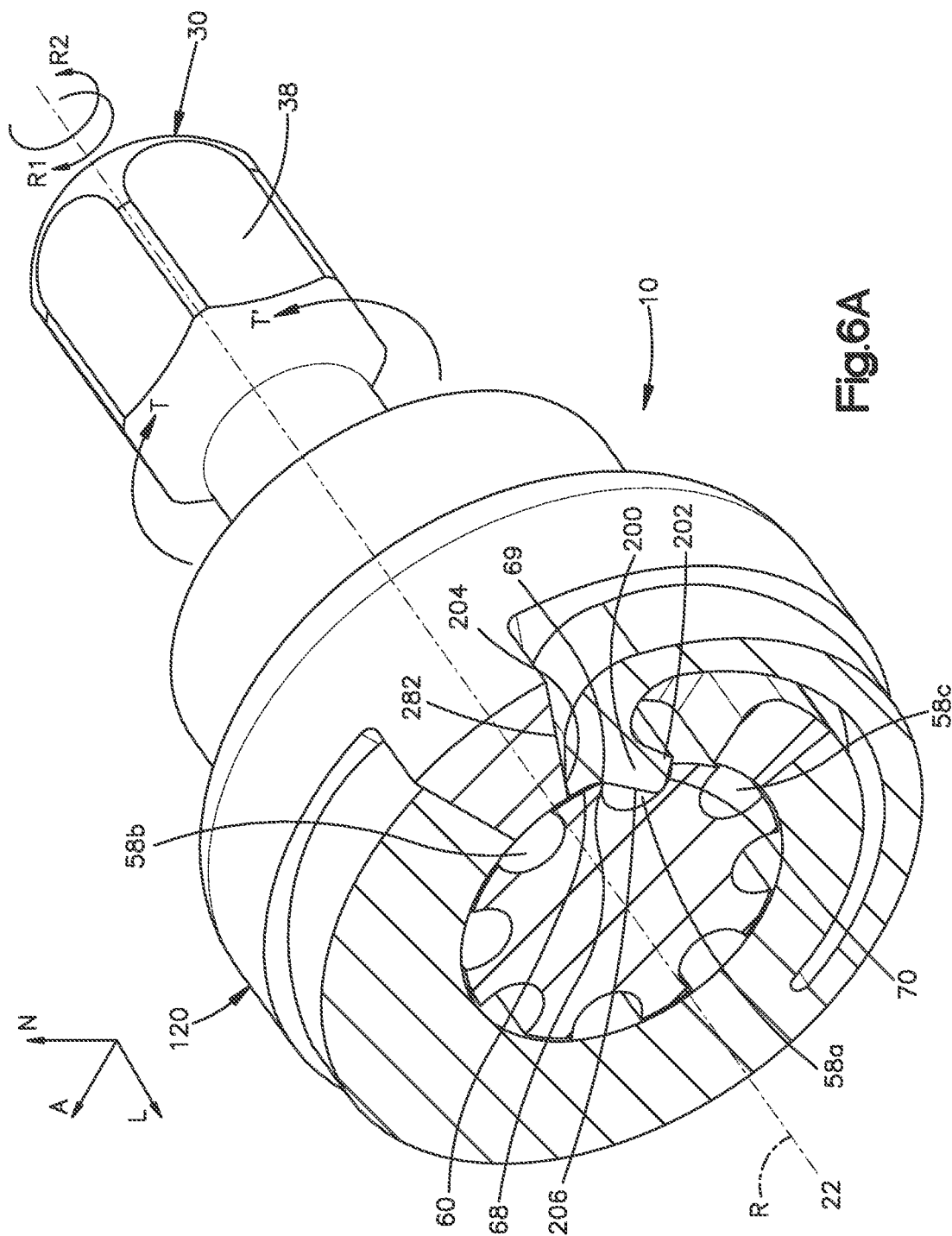
FIG. 6A is a perspective cross-sectional view of the distractor and ratchet illustrated in FIG. 5A along line 6A-6A, the ratchet and distractor in a first orientation.

Referring to FIGS. 6A and 6B, the bone distraction system 10 defines a first orientation, for example a neutral orientation, in which the screw 30 and the ratchet 120 are prevented from rotating relative to one another with respect to the axis of rotation R until either: 1) a sufficient torque T is applied in the first direction of rotation R1 to the actuation mechanism 38 of the screw 30 or 2) a sufficient torque T' is applied in the second direction of rotation R2 to the actuation mechanism 38 of the screw 30.

Referring to FIGS. 3D-3F, 4C, and 6A-6B, in the first orientation the pawl portion 200 of the ratchet tab 126 is positioned within a first recess 58*a* of the screw 30. As shown in the illustrated embodiment, the screw 30 abuts the inner pawl surface 206 blocking rotation of the screw 30 relative to the ratchet 120 in the first direction of rotation R1. In one embodiment, the outer surface 60 of the screw 30 abuts the inner pawl surface 206. In another embodiment, the first side wall 68 abuts the inner pawl surface 206. In another embodiment, both the outer surface 60 and the first side wall 68, for example an intersection 69 of the first side wall 68 and the outer surface 60 abuts the inner pawl surface 206.

Also as shown in the illustrated embodiment, the first pawl surface 202 abuts the second side wall 70 of the first recess 58*a* blocking rotation of the screw 30 relative to the ratchet 120 in the second direction of rotation R2. Additionally, the second pawl surface 204 can abut the second side wall 282 of the first projection 274, as shown in the illustrated embodiment to provide further resistance to rotation of the screw 30 relative to the ratchet 120 in the second direction of rotation R2. In one embodiment, both the inner pawl surface 206 and the second pawl surface 204 both abut the screw 30 in the first orientation such that rotation in both the first direction of rotation R1 and the second direction of rotation R2 are blocked until the torque T or T' is applied to the screw 30. The bone distraction system 10 can be configured such that when both the inner pawl surface 206 and the second pawl surface 204 engage the screw 30 simultaneously micro motion of the distractor 20, small rotation of the screw 30 relative to the sleeve 90 about the axis of rotation R is prevented.

Referring to FIGS. 3D-3F, 4C, and 6C, the bone distraction system 10 defines a second orientation in which the screw 30 rotates relative to the ratchet 120 about the axis of rotation R, in the first direction of rotation R1. A sufficient torque T is applied to the screw 30 in the first direction of rotation R1 so as to overcome the resistance to rotation provided by interference between the inner pawl surface 206 and the screw 30 and place the bone distraction system in the second orientation. In the second orientation, the screw 30 is rotatable relative to the ratchet 120 about the axis of rotation R in the first direction of rotation R1 as long as the sufficient torque T is applied to the screw 30. As shown, the screw 30, for example the intersection 69, rides along the inner pawl surface 206 causing the tip portion 184 of the ratchet 120 to cam over the screw 30. In one embodiment, the intersection 69 rides along the first portion 208 of the inner pawl surface 206 toward the intersection 214.

As the screw 30 is rotated relative to the ratchet 120 in the first direction of rotation R1, the inner pawl surface 206 cams over the screw 30 until the pawl portion 200 is completely removed from the first recess 58*a*. Further rotation of the screw 30 in the first direction of rotation R1 causes the pawl portion 200 to cam over the outer surface 60 between the first recess 58*a* and a second recess 58*b*. Rotation of the screw 30 can then be completed when the pawl portion 200 is positioned within the second recess 58*b*. Once the pawl portion 200 is positioned within the second recess 58*b*, the bone distraction system 10 is once again in the first orientation as described above, except that the pawl portion 200 is positioned within the second recess 58*b* and not the first recess 58*a*.

Referring to FIGS. 3D-3F, 4C, and 6D, the bone distraction system 10 defines a third orientation in which the screw 30 rotates relative to the ratchet 120 about the axis of rotation R, in the second direction of rotation R2. A sufficient torque T' is applied to the screw 30 in the second direction of rotation R2 so as to overcome the resistance to rotation provided by interference between the first pawl surface 202 and the second side wall 70 of the first recess 58*a*. As shown in the illustrated embodiment, the sufficient torque T' may also need to overcome the resistance to rotation provided by interference between the second pawl surface 204 and the second side wall 282 of the first projection 274. In the second orientation, the screw 30 is rotatable relative to the ratchet 120 about the axis of rotation R in the second direction of rotation R2 as long as the sufficient torque T' is applied to the screw 30.

As shown, the screw 30, for example the second side wall 70 of the first recess 58a abuts the first pawl surface 202 causing the second pawl surface 204 to abut the second side wall 282 of the first projection 274. As the sufficient torque T' is applied to the screw 30 the second pawl surface 204 slides along the second side wall 282 in the radial direction away from the axis of rotation R such that the pawl portion 200 is gradually removed from the first recess 58a. Once the second pawl surface 204 has slid along the second side wall 282 such that the pawl portion 200 is completely removed from the first recess 58a, the screw 30 is rotated in the second direction of rotation R2 until a third recess 58c is aligned with the pawl portion 200. Alignment of the third recess 58c with the pawl portion 200 causes the pawl portion 200 to enter the third recess 58c such that the bone distraction system 10 is once again in the first orientation as described above, except that the pawl portion 200 is positioned within the third recess 58c and not the first recess 58a.

Referring to FIGS. 6A-6D, according to one embodiment, the surfaces that abut to provide interference that blocks rotation in the first direction of rotation R1, for example the intersection 69 and the inner pawl surface 206, and the surfaces that abut to provide interference that blocks rotation in the second direction of rotation R2, for example the first pawl surface 202 and the second side wall 70, are each separate surfaces. According to another embodiment, the surfaces that abut to provide interference that blocks rotation in the first direction of rotation R1 and the surfaces that abut to provide interference that blocks rotation in the second direction of rotation R2 include some of, for example all of, the same surfaces.

Referring to FIGS. 6C and 6D, in one embodiment, interference between the first side wall 280 of the first projection 274 of the second collar member 128 and the first surface 152 of the ratchet tab 126 can prevent relative rotation of components of the ratchet 120, for example the ratchet tab 126 and the second collar member 128 when the screw 30 is rotated relative to the ratchet 120. The ratchet 120 can be configured such that when the first side wall 280 abuts with the first surface 152, the fourth side wall 288 of the second projection 276 and the second surface 154 of the ratchet tab 126 are spaced apart from each other by a gap 283. Alternatively, the ratchet 120 can be constructed such that the ratchet 120 is devoid of the gap 283 when the first side wall 280 abuts with the first surface 152.

In another embodiment, interference between the fourth side wall 288 of the second projection 276 of the second collar member 128 and the second surface 154 of the ratchet tab 126 can prevent relative rotation of components of the ratchet 120, for example the ratchet tab 126 and the second collar member 128 when the screw 30 is rotated relative to the ratchet 120. The ratchet 120 can be configured such that when the fourth side wall 288 abuts with the second base surface 254, the first side wall 280 and the first surface 152 of the second collar member 128 are spaced apart from each other by a gap 285. Alternatively, the ratchet 120 can be constructed such that the ratchet 120 is devoid of the gap 285 when the fourth side wall 288 abuts with the second surface 154.

Referring to FIGS. 4A-4D and 6A-6D, in one embodiment the sufficient torque T needed to rotate the screw 30 relative to the ratchet 120 about the axis of rotation R in the first direction of rotation R1 is equal to or greater than about 0.01 Newton meters ("N-m"). The value for the sufficient torque T can be changed by altering one or more of the properties of the ratchet 120 as described below. For example, the inner pawl surface 206 includes a first portion 208 that defines an angle π (pi) with respect to a radial ray RR1 that extends from the ratchet axis 136 and intersects the first portion 208. In one embodiment the angle π (pi) is about 50° which results in a value for the sufficient torque T equal to about 0.01 N-m. Increasing the angle π (pi) will decrease the value for the sufficient torque T. Decreasing the angle π (pi) will increase the value for the sufficient torque T.

Additional changes to the ratchet 120, for example increasing the angular length λ (lambda) of the boom arm portion 150, decreasing the radial length RL4, selecting a material for the ratchet 120 that has a relatively lower stiffness, etc. can result in lowering the value for the sufficient torque T. Similarly, changes to the ratchet 120, for example decreasing the angular length λ (lambda) of the boom arm portion 150, increasing the radial length RL4, selecting a material for the ratchet 120 that has a relatively higher stiffness, etc. can result in increasing the value for the sufficient torque T.

In one embodiment the sufficient torque T' needed to rotate the screw 30 relative to the ratchet 120 about the axis of rotation R in the second direction of rotation R2 is equal to or greater than about 0.05 N-m, or about 5 times the sufficient torque T. The value for the sufficient torque T' can be changed by altering one or more of the properties of the ratchet 120 as described below. For example, the first projection 274 of the second collar member 128, as shown in FIG. 6B, includes a second side wall 282 that defines an angle ν (nu) with respect to a radial ray RR3. As shown in the illustrated embodiment, the radial ray RR3 extends from the axis of rotation R along a straight line that is perpendicular to the axis of rotation R and intersects the second side wall 282 at the angle ν (nu). In one embodiment the angle ν (nu) is between about 2° and about 14°. In another embodiment, the angle ν (nu) is about 8° which results in a value for the sufficient torque T' equal to about 0.05 N-m. Increasing the angle ν (nu) will increase the value for the sufficient torque T', while decreasing the angle ν (nu) will decrease the value for the sufficient torque T'. As described above in reference to the sufficient torque T, additional changes to the ratchet 120 can result in raising or lowering the value for the sufficient torque T'.

Referring to FIGS. 7A-8B, in one embodiment the bone distraction system 10 is constructed so as to define an engaged configuration and a disengaged configuration. As shown in the illustrated embodiment, the bone distraction system 10 includes a ratchet 1120 according to another embodiment. The ratchet 1120 can be constructed similarly to the ratchet 120 as described above, except for the differences described below.

In the disengaged configuration the ratchet 1120 is disengaged from the screw 30 such that the screw 30 is rotatable relative to the ratchet 1120 with respect to the axis of rotation R, without applying a sufficient torque T or T' to the screw 30. In the disengaged configuration any torque T applied to the screw 30 will rotate the screw 30 in the first direction of rotation R1 relative to the ratchet 1120, and any torque T' applied to the screw 30 will rotate the screw 30 in the second direction of rotation R2 relative to the ratchet 1120.

In the engaged configuration the ratchet 1120 is engaged to the screw 30 similarly to as described above in reference to the ratchet 120 and the screw 30. In the engaged configuration the screw 30 is rotatable relative to the ratchet 1120 with respect to the axis of rotation R, only once a sufficient torque T or T' has been applied to the screw 30.

Figure 7A:
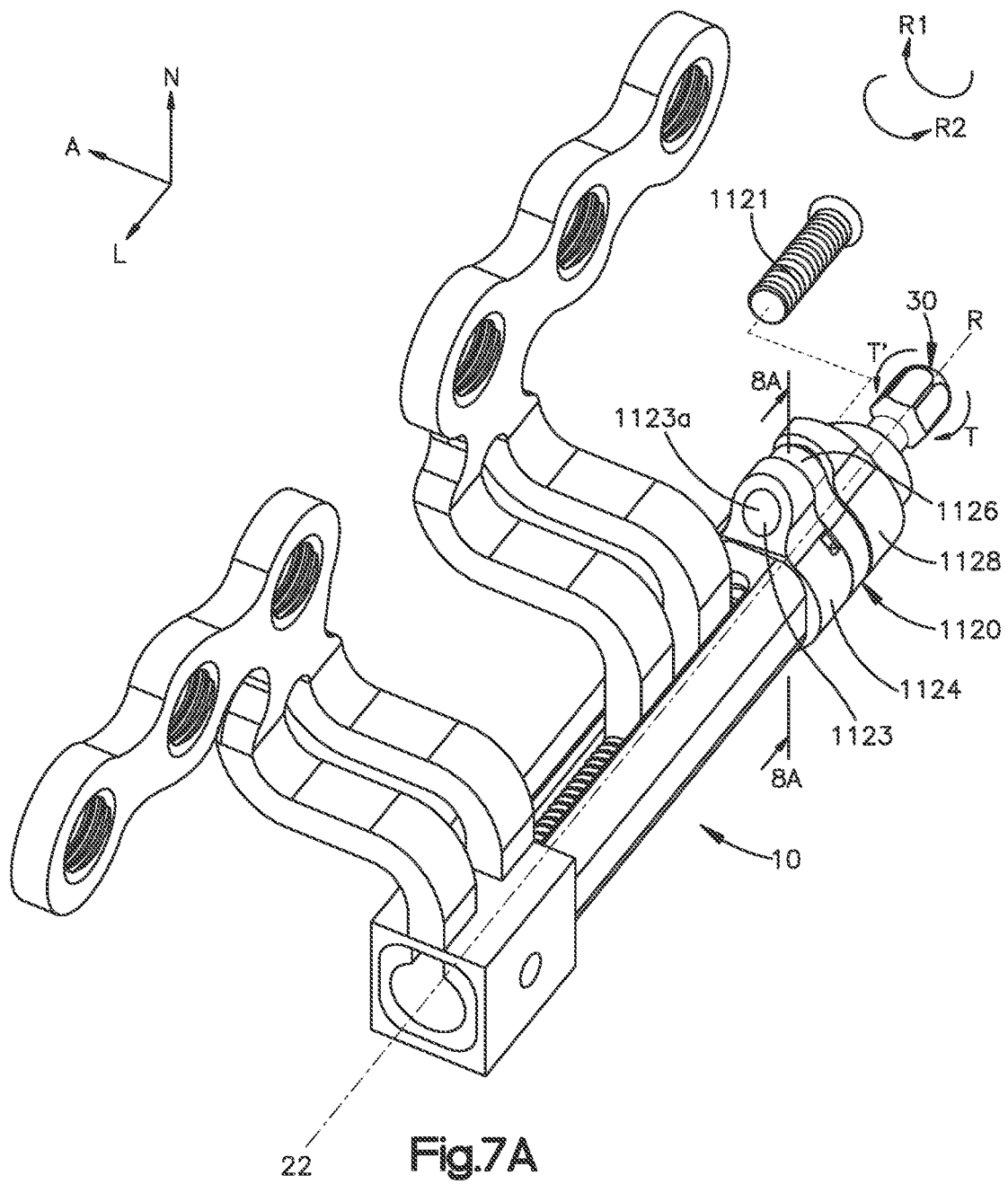
FIG. 7A is a perspective view of the bone distraction system illustrated in FIG. 1, the bone distraction system including the distractor, first footplate, and second footplate illustrated in FIG. 2A, and the bone distraction system including a ratchet according to another embodiment.

Referring to FIGS. 7A-7B and 8A, in the disengaged configuration the pawl portion 1200 of the ratchet tab 1126 is removed from contact with the screw 30. As shown the pawl portion 1200 is radially spaced from the recess 58 of the screw 30. Thus, in the disengaged configuration there is no interference between the ratchet 1120 and the screw 30. As a result, in the disengaged configuration any torque T or T' applied to the screw 30 will rotate the screw 30 relative to the ratchet 1120 with respect to the axis of rotation R.

In one embodiment, the ratchet 1120 includes a securing element 1121 that is configured to be inserted into a securing element recess 1123 that is defined by the ratchet 1120. As shown in the illustrated embodiment, the securing element recess 1123 includes a first securing element recess 1123a defined by the first collar member 1124, a second securing element recess 1123b defined by the ratchet tab 1126, and a third securing element recess 1123c defined by the second collar member 1128. When the securing element 1121 is inserted into the securing element recess 1123, the first, second, and third securing element recesses 1123a, 1123b, and 1123c are aligned and the pawl portion 1200 is spaced from the screw 30.

Referring to FIGS. 7A-7B and 8B, in the engaged configuration the securing element 1121 has been removed from the securing element recess 1123. The second securing element recess 1123b of the ratchet tab 1126 is biased so as to be out of alignment with the first and third securing element recesses 1123a and 1123c, such that the pawl portion 1200 of the ratchet tab 1126 is engaged with the screw 30, for example the pawl portion 1200 protrudes radially inward toward the axis of rotation R and at least partially into the recess 58. Thus, in the engaged configuration interference between the ratchet 1120 and the screw 30 requires a sufficient torque T or T' to be applied to the screw 30, as described in detail above with respect to ratchet 120, to rotate the screw 30 relative to the ratchet 1120 with respect to the axis of rotation R.

Referring to FIGS. 7A-7B and 9, in one embodiment the securing element 1121 is in the form of a threaded member 1122, for example a screw, that defines a first end 1125, a second end 1127 that is spaced from the first end 1125, and a securing element body 1129 that extends from the first end 1125 to the second end 1127. The first end 1125 is configured to be inserted into the securing element recess 1123 to place the bone distraction system 10 in the disengaged configuration. The second end 1127 is configured to receive an instrument to remove the securing element 1121 from the securing element recess 1123 so as to place the bone distraction system 10 in the engaged configuration.

Referring to FIG. 9, in one embodiment the first end 1125 of the securing element 1121 includes an externally threaded shaft 1131 that corresponds to internal threads within the securing element recess 1123. The second end 1127 can include an external hex drive configured to receive an instrument with a corresponding internal hex tip that provides a torque to the securing element 1121 to rotate the securing element 1121 and disengage the externally threaded shaft 1131 from the securing element recess 1123. In one embodiment the securing element body 1129 is flexible such that the first end 1125 is spaced from the second end 1127 along a nonlinear path. In one embodiment the securing element 1121 defines a length L1 measured from the first end 1125 to the second end 1127 such that when the externally threaded shaft 1131 is inserted into the securing element recess 1123 the second end 1127 is positioned proximate the actuation mechanism 38 of the screw 30. According to one embodiment the securing element defines a length L1 between about 10 mm and about 50 mm. In another embodiment the securing element defines a length L1 of about 33 mm.

Referring to FIGS. 7A-7B and 10A-10C, in one embodiment the securing element 1121 is in the form of an unthreaded member 1140, such as a stepped pull pin, that defines a first end 1142, a second end 1144 that is spaced from the first end 1142, and an unthreaded member body 1146 that extends from the first end 1142 to the second end 1144. The unthreaded member body 1146 includes a first portion 1148 that is configured to be inserted into the securing element recess 1123 and a second portion 1150 that is configured to be positioned outside the securing element recess 1123 when the first portion 1148 is inserted into the securing element recess 1123. As shown in the illustrated embodiment, the first portion 1148 defines a cross sectional dimension D5 that is less than the size of the securing element recess 1123.

According to one embodiment the first portion 1148 can include a tapered surface 1152 such that the cross sectional dimension D5 increases from a first location within the first portion to a second location within the first portion, the first location being positioned closer to the first end 1142 than the second location. The tapered surface 1152 can be configured such that the unthreaded member 1140 is easily insertable into the securing element recess at first, and then becomes gradually more difficult.

As shown in the illustrated embodiment, the unthreaded member 1140 can include a tip portion 1153 that is configured to be flexible such that the tip portion 1153 can be bent to provide additional securement of the unthreaded member 1140 within the securing element recess 1123. For example, the unthreaded member 1140 can be configured to be inserted into the securing element recess 1123 such that the tip portion 1153 extends all the way through the securing element recess 1123 and protrudes out from the first securing element recess 1123a. The tip portion 1153 can be configured to be bent such that the tip portion 1153 will abut the first collar member 1124 and resist translation of the unthreaded member 1140 through the securing element recess 1123. In another embodiment, the tip portion 1153 is configured to prevent accidental removal of the unthreaded member 1140 from the securing element recess 1123, but a sufficient force applied from a surgeon or other user will cause the tip portion 1153 to deflect until the tip portion 1153 is aligned with the securing element recess, allowing the unthreaded member 1140 to be removed from the securing element recess.

According to one embodiment, the tip portion 1153 can be positioned within the first portion 1148, for example within a portion of the first portion 1148 that is closest to the first end 1142. As shown, the tip portion 1153 can define a cross sectional dimension that is smaller than a remaining portion of the first portion 1148.

The unthreaded member 1140 can further include an intermediate portion 1149 positioned between the first portion 1148 and the second portion 1150. As shown in the illustrated embodiment, the intermediate portion 1149 defines a cross sectional dimension D6 that is greater than the cross sectional dimension D5 of the first portion 1148. In one embodiment, the unthreaded member 1140 and the securing element recess 1123 can each be configured such that the first portion 1148 is sized to fit through both the third securing element recess 1123c and the second securing element recess 1123b, while the intermediate portion 1149 is sized to fit through the third securing element 1123c but not the second securing element 1123b, such that the intermediate portion 1149 is configured to act as a stop and prevent over-insertion of the unthreaded member 1140 into the securing element recess 1123. In the embodiment described above, the second securing element recess 1123b is smaller than the third securing element recess 1123c.

The unthreaded member 1140 can further include one or more features configured to enable a force to be applied to the unthreaded member 1140, the force being sufficient to remove the unthreaded member 1140 from the securing element recess 1123 in order to actuate the ratchet 1120 from the disengaged configuration to the engaged configuration.

In one embodiment, the unthreaded member 1140 includes a hole 1154, for example a through hole, and a strand member 1156, such as a wire, the hole 1154 being configured to receive the strand member 1156. The strand member 1156 is configured to be attached to the unthreaded member 1140, for example by looping the strand member 1156 directly through the hole 1154, or by attaching the strand member 1156 to an intermediate member (not shown), such as a ring that is passed through and secured within the hole 1154. When the unthreaded member 1140 is inserted into securing element recess 1123, a force can be applied to the strand member 1156, for example by a surgeon pulling on the strand member 1156. The force causes the unthreaded member 1140 to translate out of the securing element recess 1123 which causes the ratchet 1120 to actuate to the engaged configuration.

In one embodiment the unthreaded member 1140 can include a gripping portion 1158 that is configured to receive a force that is applied to the unthreaded member 1140, the force being sufficient to remove the unthreaded member 1140 from the securing element recess 1123 in order to actuate the ratchet 1120 from the disengaged configuration to the engaged configuration. As shown in the illustrated embodiment, the gripping portion 1158 can include a left side wall 1160 and a right side wall 1162 that is opposite the left side wall 1160. As shown, the left side wall 1160 and the right side wall 1162 can be parallel to each other such that a forceps or other surgical instrument can easily grab the unthreaded member 1140 and apply a force to the unthreaded member 1140 sufficient to remove the unthreaded member 1140 from the securing element recess 1123. Alternatively, the left side wall 1160 and the right side wall 1162 can be non-parallel such that a forceps or other surgical instrument can easily grab the unthreaded member 1140 and apply a force to the unthreaded member 1140 sufficient to remove the unthreaded member 1140 from the securing element recess 1123.

In one embodiment, the gripping portion 1158 is positioned within the second portion 1150, specifically at the second end 1144 of the unthreaded member 1140. The gripping portion 1158 can further include a curved surface 1164 that extends between the left side wall 1160 and the right side wall 1162. As shown in the illustrated embodiment the curved surface 1164 is the portion of the unthreaded member 1140 that is closest to the second end 1144 of the unthreaded member 1140, such that during removal of the unthreaded member 1140 from the securing element recess 1123, the curved surface 1164 is the leading surface of the unthreaded member 1140. The curved surface 1164 being the leading surface during removal of the unthreaded member 1140 from the securing element recess 1123 may help prevent damage or trauma to tissues proximate the bone distraction system 10.

As shown in the illustrated embodiment, the unthreaded member 1140 can include both the hole 1154 and the gripping portion 1158. In another embodiment the unthreaded member includes either the hole 1154 or the gripping portion 1158.

Referring to FIGS. 11 and 12A-12C, according to one embodiment the bone distraction system 10 can include a distractor 20', a ratchet 120', the first footplate 320, and the second footplate 420. According to one embodiment, the distractor 20' includes a screw 30' and the sleeve 90 that are configured to be connected to each other such that the screw 30' is rotatable relative to the sleeve 90 about the axis of rotation R, and vice versa. The screw 30' is similar to the screw 30 (described in detail in reference to FIGS. 2A-2B and 3A-3B above) in many aspects such that the description of the screw 30 herein can be applied to the screw 30'. Differences between the screw 30 and the screw 30' are highlighted below.

The screw 30' includes the ratchet engagement structure 56', for example within the third portion 54 as shown in the illustrated embodiment. The ratchet engagement structure 56' is configured to engage the ratchet 120' such that interference between the ratchet 120' and the third portion 54 of the screw 30' restricts relative rotation of the ratchet 120' and the screw 30' such that a minimum torque value, for example the sufficient torque T, must be applied to the screw 30', to rotate the screw 30' relative to the ratchet 120', or vice versa, about the axis of rotation R.

As shown in the illustrated embodiment, the third portion 54 can be disposed within the first portion 34 such that when the screw 30' and sleeve 90 are assembled to form the distractor 20', the third portion 54 is positioned outside the sleeve borehole 98 of the sleeve 90. In another embodiment the third portion 54 can be disposed within the second portion 36 such that when the screw 30' and sleeve 90 are assembled to form the distractor 20', the third portion 54 is positioned inside the sleeve borehole 98 of the sleeve 90. In yet another embodiment the third portion 54 can be disposed between the first portion 34 and the second portion 36 such that when the screw 30' and sleeve 90 are assembled to form the distractor 20', the third portion 54 is positioned partially inside the sleeve borehole 98 and partially outside the sleeve borehole 98.

According to one embodiment the ratchet engagement structure 56' includes at least one flat 358. In another embodiment the ratchet engagement structure 56 can include a plurality of flats 358 that are radially spaced about the screw axis 44 from adjacent ones of the plurality of flats 358 by an angle α' (alpha prime). The angle α' (alpha prime) can be measured from a first radial ray RR4 to a second radial ray RR5 about the screw axis 44. The first radial ray RR4 extends from the screw axis 44 and passes perpendicularly through one of the plurality of flats 358. The second radial ray RR5 extends from the screw axis 44 and passes perpendicularly through an adjacent one of the plurality of flats 358.

As shown in the illustrated embodiment, the ratchet engagement structure 56' includes four flats 358, each of the flats 358 being equidistantly spaced such that the angle α' (alpha prime) equals about 90° between adjacent ones of the flats 358. In another embodiment the plurality of flats 358 can include from between one and twelve flats 358. In another embodiment the angle α' (alpha prime) between different pairs of adjacent ones of the plurality of flats 358 can vary such that each of the plurality of flats 358 is not equidistantly spaced from adjacent ones of the plurality of flats 358.

As shown in the illustrated embodiment, each of the plurality of flats 358 can be spaced from an adjacent one of the plurality of flats 358 by a curved surface 360. As shown each of the curved surfaces 360 extend between adjacent ones of the plurality of flats 358, for example from one of the plurality of flats 358 to an adjacent one of the plurality of flats 358. According to one embodiment, each of the curved surfaces 360, for example an entirety of each of the curved surfaces 360, intersect a circle that is centered on the screw axis 44.

Referring to FIGS. 12A-12C and 13A-13C, in one embodiment, the ratchet 120' includes a first end 130', a second end 132' spaced from the first end 130' in a direction, for example the longitudinal direction L, and a ratchet body 122' extending from the first end 130' to the second end 132'. The ratchet 120' defines a ratchet borehole 134' that extends through the ratchet body 122' from the first end 130' to the second end 132' along a ratchet axis 136'. As shown, the ratchet axis 136' can be positioned centrally within the ratchet borehole 134'.

The ratchet body 122' can include a ratchet tab 126' that is configured to be connected to the distractor 20' such that the ratchet tab 126' is translationally and rotationally secured to the sleeve 90 such that translation of the ratchet 120' along the axis of rotation R relative to the sleeve 90 and rotation of the ratchet 120' about the axis of rotation R relative to the sleeve 90 are both prevented. Additionally, the ratchet tab 126' is translationally secured and rotatable relative to the screw 30' such that translation of the ratchet 120' along the axis of rotation R relative to the screw 30' is prevented, but rotation of the ratchet 120' about the axis of rotation R relative to the screw 30' is permitted.

Figure 13A:
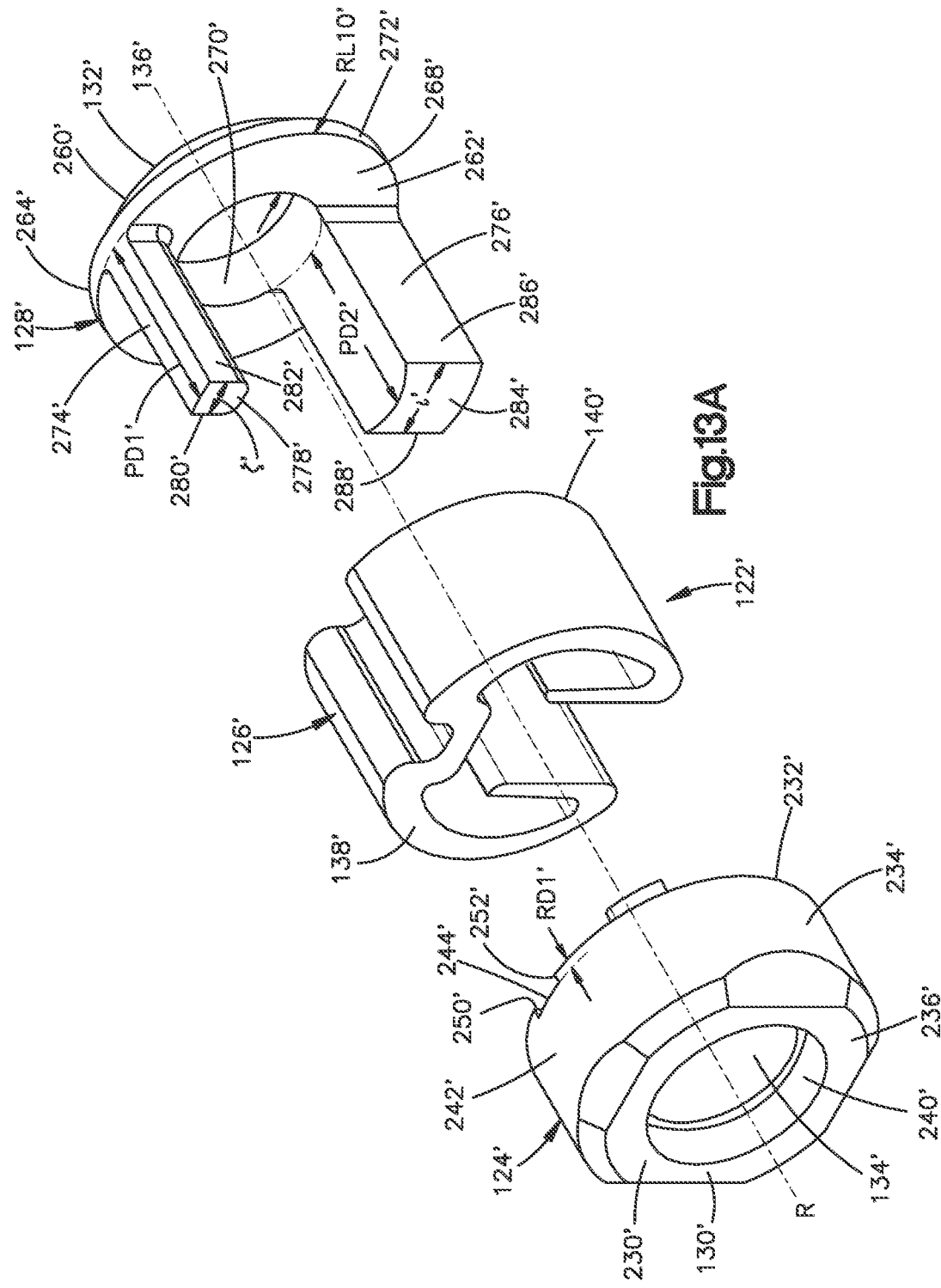
FIG. 13A is an exploded perspective view of the ratchet illustrated in FIG. 11, the ratchet including a first collar member, a ratchet tab according to one embodiment, and a second collar member.
Figure 13B:
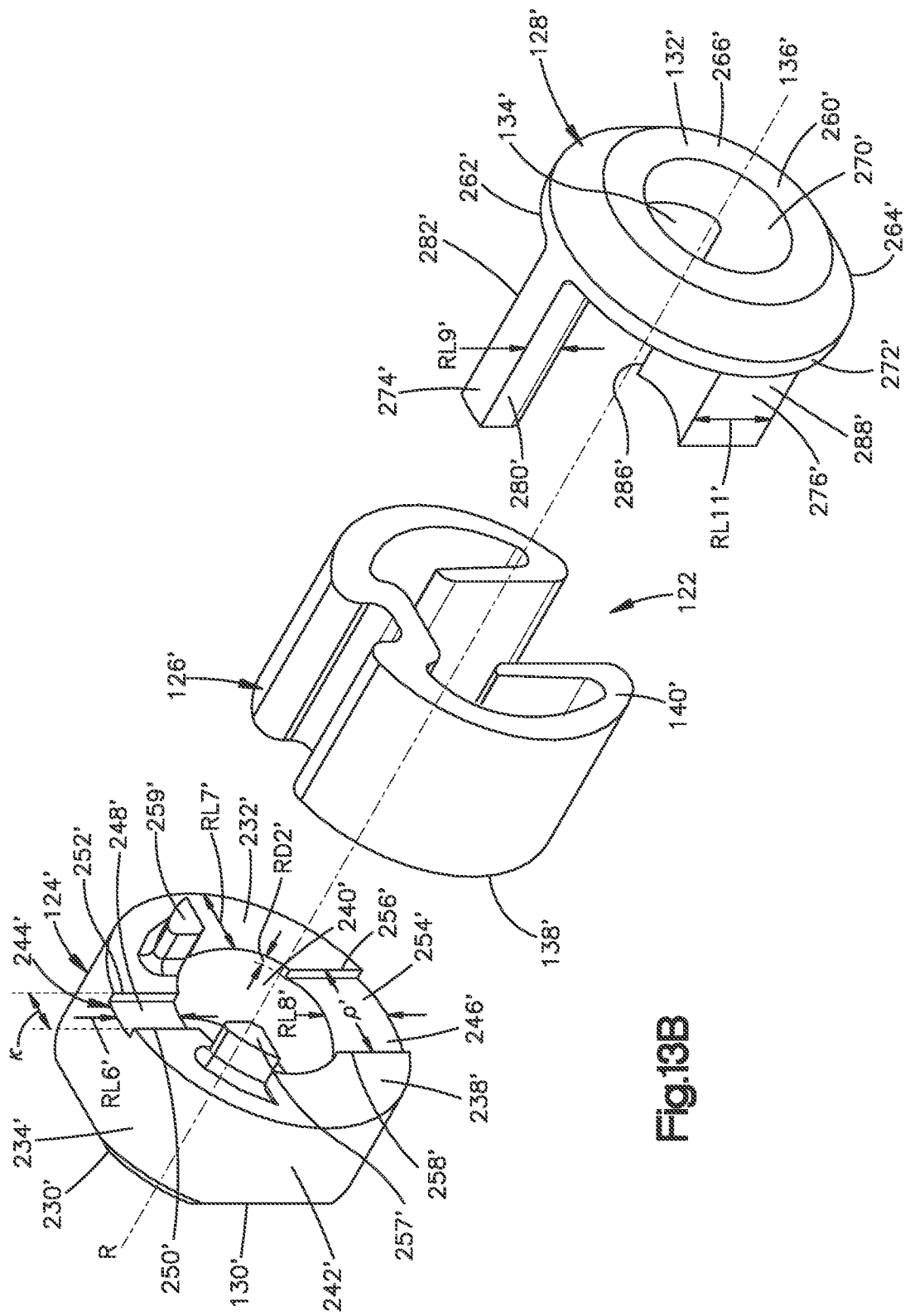
FIG. 13B is another exploded perspective view of the ratchet illustrated in FIG. 13A.
Figure 13C:
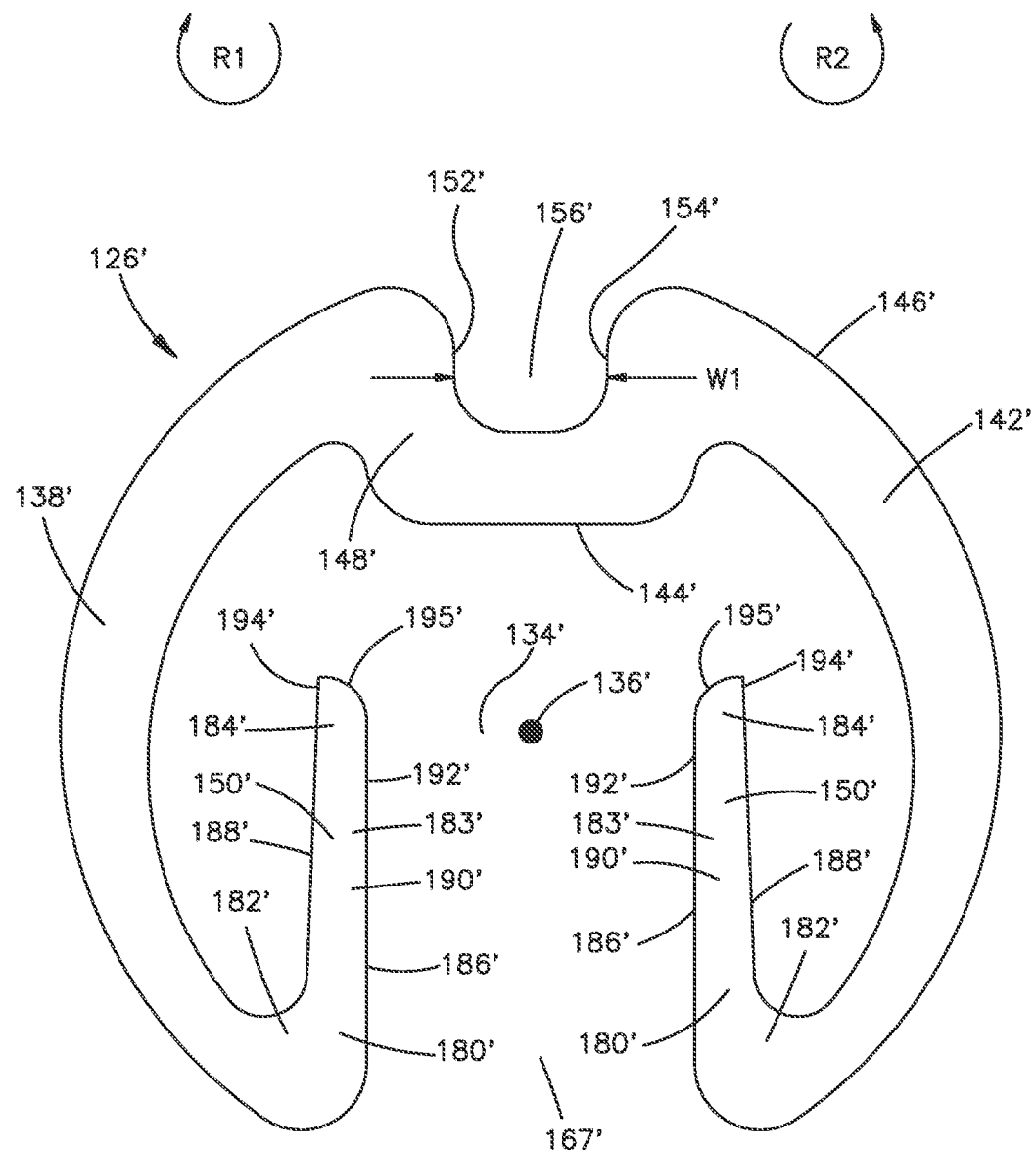
FIG. 13C is a front view of the ratchet tab illustrated in FIG. 13A.

Referring to FIGS. 13A-13C, the ratchet tab 126' includes a first end 138', a second end 140' spaced from the first end 138' along a first direction, for example the longitudinal direction L, and a ratchet tab body 142' that extends from the first end 138' to the second end 140' along the ratchet axis 136'. The ratchet borehole 134' extends through the ratchet tab body 142' from the first end 138' of the ratchet tab 126' to the second end 140' of the ratchet tab 126'. As shown in the illustrated embodiment, the ratchet tab body 142' can include an inner surface 144' that faces the ratchet axis 136' and at least partially defines the ratchet borehole 134'. As shown, the ratchet tab body 142' can further include an outer surface 146' that faces opposite the inner surface 144' of the ratchet tab body 142'.

According to one embodiment, the ratchet tab body 142' can be constructed to include a base portion 148' and at least one boom arm portion 150'. The base portion 148' includes a first surface 152' that faces in a first direction of rotation R1 about the ratchet axis 136' and a second surface 154' that faces in a second direction of rotation R2 about the ratchet axis 136'. In one embodiment, the second direction of rotation R2 is opposite the first direction of rotation R1 with respect to the ratchet axis 136'. In another embodiment, the first direction of rotation R1 is clockwise and the second direction of rotation R2 is counterclockwise. The first surface 152' and the second surface 154' are spaced apart so as to define a gap 156' between the first surface 152' and the second surface 154'. The gap 156' defines a width W1 measured in a direction perpendicular to the ratchet axis 136'.

The at least one boom arm portion 150' (referred to herein as the boom arm portion 150'), according to one embodiment, includes a boom arm body 180' that has a fulcrum portion 182' and a distractor body engagement structure 183'. As shown in the illustrated embodiment, the distractor body engagement structure 183' can include a tip portion 184' that is configured to engage the ratchet engagement structure 56', for example the flat 358, of the screw 30'. The fulcrum portion 182' is attached to the base portion 148'. As shown in the illustrated embodiment, the fulcrum portion 182' can be monolithic, or a single integral piece, with the base portion 148'. In another embodiment, the fulcrum portion 182' and the base portion 148' can be releasably attached.

According to one embodiment, the boom arm body 180' includes a first surface 186' and a second surface 188' that is opposite the first surface 186'. As shown, at least a portion of the first surface 186' can face the ratchet axis 136' and the second surface 188' can face away from the ratchet axis 136'.

The tip portion 184' includes an inner surface 192' that faces the ratchet axis 136', an outer surface 194' spaced from the inner surface 192', and an intermediate surface 195' that connects the inner surface 192' to the outer surface 194'. According to one embodiment the intermediate surface 195' is curved such that the tip portion 184' is tapered.

As shown in the illustrated embodiment, the ratchet tab body 142' can include, as shown, a pair of boom arm portions 150'. According to another embodiment, the ratchet tab body 142' can include a single boom arm portion 150'. According to another embodiment, the ratchet tab body 142' can include three or more boom arm portions 150'. According to one embodiment, the pair of boom arm portions 150' is arranged, as shown, such that the second surfaces 188' of the pair of boom arm portions 150' are parallel to one another. Referring to FIG. 13D, in another embodiment the pair of boom arm portions 150' can be arranged such that the second surfaces 188' of the pair of boom arm portions 150' are non-parallel, for example perpendicular, to one another. Referring again to FIGS. 13A-13C, according to one embodiment, the pair of boom arm portions 150' is arranged, as shown, such that the first surfaces 186' of the pair of boom arm portions 150' face one another and define a gap 167' therebetween. According to another embodiment, the pair of boom arm portions 150' can be arranged such that the first surfaces 186' of the pair of boom arm portions 150' face away from one another. According to one embodiment, the boom arm portion 150' consists of a single linear member 190' that extends from the fulcrum portion 182' and defines the tip portion 184'.

Referring to FIGS. 13D-13G, other embodiments of the ratchet tab 126' can include boom arm portions 150' that include a first linear member 190a' that extends from the fulcrum portion 182' and a second linear member 190b' that defines the tip portion 184'. As shown in FIG. 13D the first linear member 190a' can be monolithic with the second linear member 190b'. As shown in FIG. 13E the first linear member 190a' can be directly connected to the second linear member 190b'. As shown in FIGS. 13F and 13G the first linear member 190a' is connected to the second linear member 190b' through at least one intermediate linear member 190c' (referred to herein as the intermediate linear member 190c'). Adjacent ones of the first linear member 190a', the second linear member 190b' and the intermediate linear member 190c' can be arranged in various configurations. In one embodiment, adjacent ones of the first linear member 190a', the second linear member 190b' and the intermediate linear member 190c' are arranged perpendicularly. In another embodiment, adjacent ones of the first linear member 190a', the second linear member 190b' and the intermediate linear member 190c' are arranged at an acute angle. In another embodiment, adjacent ones of the first linear member 190a', the second linear member 190b' and the intermediate linear member 190c' are arranged at an obtuse angle.

Referring again to FIGS. 13A-13C, in one embodiment, the ratchet 120' can include at least one collar member, for example a first collar member 124' and a second collar member 128', configured to secure the ratchet tab 126' to the distractor 20' such that 1) the ratchet tab 126' is translationally and rotationally secured to the sleeve 90 relative to the axis of rotation R; and 2) the ratchet tab 126' is translationally secured and rotatable relative to the screw 30' with respect to the axis of rotation R.

As shown in the illustrated embodiment, the first collar member 124' can include a first end 230', a second end 232' spaced from the first end 230' along a first direction, for example the longitudinal direction L, and a first collar member body 234' that extends from the first end 230' to the second end 232' along the ratchet axis 136'. The first collar member body 234' includes a first end surface 236' and a second end surface 238'. As shown, the first end surface 236' is proximate the first end 230', and the second end surface 238' is opposite the first end surface 236' and is proximate the second end 232'.

In one embodiment, the ratchet borehole 134' can extend through the first collar member body 234' from the first end 230' of the first collar member 124' to the second end 232' of the first collar member 124'. In one embodiment, the first collar member body 234' can include an inner surface 240' that faces the ratchet axis 136' and at least partially defines the ratchet borehole 134'. As shown, the first collar member body 234' can further include an outer surface 242' that is radially spaced from the inner surface 240' and faces opposite the inner surface 240'.

The first collar member 124' can further include at least one recess, for example a first recess 244' and a second recess 246'. As shown in the illustrated embodiment, the first recess 244' extends into the second end surface 238' of the first collar member body 234' in a direction, for example the longitudinal direction L, toward the first end surface 236' so as to define a first recess depth RD1'. In one embodiment, the first collar member body 234' includes a first base surface 248' positioned between the first end surface 236' and the second end surface 238' with respect to the longitudinal direction L such that the first recess 244' terminates at first base surface 248'. In one embodiment the first base surface 248' is substantially flat. In another embodiment the first base surface 248' is not flat, for example substantially curved.

The first recess 244' extends between the inner surface 240' and the outer surface 242' in the radial direction so as to define a radial length RL6'. As shown in the illustrated embodiment, the first recess 244' can extend from the inner surface 240' to the outer surface 242' such that the radial length RL6' of the first recess 244' is the same as a radial length RL7' of the first collar member 124'. In another embodiment the radial length RL6' of the first recess 244' is less than the radial length RL7' of the first collar member 124'.

As shown in the illustrated embodiment, the first collar member body 234' can further include a first side wall 250' and a second side wall 252' that is spaced from the first side wall 250' with respect to an angular direction centered on the ratchet axis 136'. The first side wall 250' and the second side wall 252' each: 1) extend between the inner surface 240' and the outer surface 242' in the radial direction; and 2) also extend between the second end surface 238' and the first base surface 248'. The first recess 244' extends between the first side wall 250' and the second side wall 252' so as to define an angular length κ' (kappa prime).

As shown in the illustrated embodiment, the second recess 246' can extend into the second end surface 238' of the first collar member body 234' in a direction, for example the longitudinal direction L, toward the first end surface 236' so as to define a second recess depth RD2'. In one embodiment, the first collar member body 234' includes a second base surface 254' positioned between the first end surface 236' and the second end surface 238' with respect to the longitudinal direction L such that the second recess 246' terminates at second base surface 254'. In one embodiment the second base surface 254' is substantially flat. In another embodiment the second base surface 254' is not flat, for example substantially curved.

The second recess 246' extends between the inner surface 240' and the outer surface 242' in the radial direction so as to define a radial length RL8'. As shown in the illustrated embodiment, the second recess 246' can extend from the inner surface 240' to the outer surface 242' such that the radial length RL8' of the second recess 246' is the same as the radial length RL7' of the first collar member 124'. In another embodiment the radial length RL8' of the second recess 246' is less than the radial length RL7' of the first collar member 124'.

As shown in the illustrated embodiment, the first collar member body 234' can further include a third side wall 256' and a fourth side wall 258' that is spaced from the third side wall 256' with respect to an angular direction centered on the ratchet axis 136'. The third side wall 256' and the fourth side wall 258' each: 1) extend between the inner surface 240' and the outer surface 242' in the radial direction; and 2) also extend between the second end surface 238' and the second base surface 254'. The second recess 246' extends between the third side wall 256' and the fourth side wall 258' so as to define an angular length ρ' (rho prime).

The second collar member 128' of the ratchet 120', according to one embodiment, is constructed similarly to the first collar member 124' except that instead of defining recesses the second collar member 128' includes projections. As shown in the illustrated embodiment, the second collar member 128' can include a first end 260', a second end 262' spaced from the first end 260' along a first direction, for example the longitudinal direction L, and a second collar member body 264' that extends from the first end 260' to the second end 262' along the ratchet axis 136'. The second collar member body 264' includes a first end surface 266' and a second end surface 268'. As shown, the first end surface 266' is proximate the first end 260', and the second end surface 268' is opposite the first end surface 266' and is proximate the second end 262'.

In one embodiment, the ratchet borehole 134' can extend through the second collar member body 264' from the first end 260' of the second collar member 128' to the second end 262' of the second collar member 128'. In one embodiment, the second collar member body 264' can include an inner surface 270' that faces the ratchet axis 136' and at least partially defines the ratchet borehole 134'. As shown, the second collar member body 264' can further include an outer surface 272' that is radially spaced from the inner surface 270' and faces opposite the inner surface 270'.

The second collar member 128' can further include at least one projection, for example a first projection 274' and a second projection 276'. As shown in the illustrated embodiment, the first projection 274' extends out from the second end surface 268' of the second collar member body 264' in a direction, for example the longitudinal direction L, away from the first end surface 266' so as to define a first projection depth PD1'. In one embodiment, the second collar member 128' includes a first tip surface 278' positioned outside (or not between) the first end surface 266' and the second end surface 268' with respect to the longitudinal direction L such that the first projection 274' terminates at the first tip surface 278'. In one embodiment the first tip surface 278' corresponds in shape to the first base surface 248'. In another embodiment the first tip surface 278' is substantially flat. In another embodiment the first tip surface 278' is not flat, for example substantially curved.

The first projection 274' extends between the inner surface 270' and the outer surface 272' with respect to the radial direction so as to define a radial length RL9'. As shown in the illustrated embodiment, the first projection 274' can extend from the inner surface 270' to the outer surface 272' such that the radial length RL9' of the first projection 274' is the same as a radial length RL10' of the second collar member 128'. In one embodiment the radial length RL9' of the first projection 274' corresponds to the radial length RL6' of the first recess 244'. In another embodiment the radial length RL9' of the first projection 274' is less than the radial length RL10' of the second collar member 128'.

As shown in the illustrated embodiment, the first projection 274' can further include a first side wall 280' and a second side wall 282' that is spaced from the first side wall 280' with respect to an angular direction centered on the ratchet axis 136'. The first side wall 280' and the second side wall 282' each: 1) extend between the inner surface 270' and the outer surface 272' in the radial direction; and 2) also extend between the second end surface 268' and the first tip surface 278'. The first projection 274' extends between the first side wall 280' and the second side wall 282' so as to define an angular length $\zeta$ (zeta prime).

As shown in the illustrated embodiment, the second projection 276' can extend out from the second end surface 268' of the second collar member body 264' in a direction, for example the longitudinal direction L, away from the first end surface 266' so as to define a second projection depth PD2'. In one embodiment, the second collar member 128' includes a second tip surface 284' positioned outside (or not between) the first end surface 266' and the second end surface 268' with respect to the longitudinal direction L such that the second projection 276' terminates at second tip surface 284'. In one embodiment the second tip surface 284' corresponds in shape to the second base surface 254'. In another embodiment the second tip surface 284' is substantially flat. In another embodiment the second tip surface 284' is not flat, for example substantially curved.

The second projection 276' extends between the inner surface 270' and the outer surface 272' in the radial direction so as to define a radial length RL11'. As shown in the illustrated embodiment, the second projection 276' can extend from the inner surface 270' to the outer surface 272' such that the radial length RL11' of the second projection 276' is the same as the radial length RL10' of the second collar member 128'. In another embodiment the radial length RL11' of the second projection 276' is less than the radial length RL10' of the second collar member 128'.

As shown in the illustrated embodiment, the second projection 276' can further include a third side wall 286' and a fourth side wall 288' that is spaced from the third side wall 286' with respect to an angular direction centered on the ratchet axis 136'. The third side wall 286' and the fourth side wall 288' each: 1) extend between the inner surface 270' and the outer surface 272' in the radial direction; and 2) also extend between the second end surface 268' and the second tip surface 284'. The second projection 276' extends between the third side wall 286' and the fourth side wall 288' so as to define an angular length $\iota$' (iota prime).

The ratchet 120', in accordance with one embodiment, is configured to be assembled as described below. The first collar member 124', the ratchet tab 126', and the second collar member 128' are aligned such that the inner surfaces 240', 144', and 270' collectively define at least a portion of the ratchet borehole 134'. The first collar member 124', the ratchet tab 126', and the second collar member 128' are further aligned such that the first recess 244', the gap 156', and the first projection 274' are aligned. Additionally, the first collar member 124', the ratchet tab 126', and the second collar member 128' are further aligned such that the second recess 246', the gap 167', and the second projection 276' are aligned. The ratchet 120' is further configured such that translation of the first collar member 124' toward the first end 138' of the ratchet tab 126' and translation of the second collar member 128' toward the second end 140' of the ratchet tab 126' results in the insertion of the first projection 274' through the gap 156' and into the first recess 244'. The translation of the first collar member 124' toward the first end 138' of the ratchet tab 126' and translation of the second collar member 128' toward the second end 140' of the ratchet tab 126' further results in the insertion of the second projection 276' through the gap 167' and into the second recess 246'.

Assembly of the ratchet 120' as described above, results in the first collar member 124', the ratchet tab 126', and the second collar member 128' being rotationally secured relative to each other with respect to the ratchet axis 136'.

Referring to FIGS. 11 and 12A-12C, in accordance with one embodiment, the bone distraction system 10 defines an assembled configuration in which: 1) the ratchet 120' is both translationally secured and rotationally secured to the sleeve 90 such that the ratchet 120' cannot translate along or rotate about the axis of rotation R relative to the sleeve 90; 2) the screw 30' is translationally secured relative to the sleeve 90 such that the screw 30' cannot translate relative to the sleeve 90 with respect to the axis of rotation R; 3) the screw 30' is rotatable relative to both the sleeve 90 and the ratchet 120' with respect to the axis of rotation R. In one embodiment when the bone distraction system 10 is in the assembled configuration: 4) the screw 30' is translationally secured relative to the ratchet 120' with respect to the axis of rotation R.

When the bone distraction system 10 is in the assembled configuration the distractor 20' can be actuated to rotate the screw 30' relative to the ratchet 120' about the axis of rotation R. The ratchet 120' is configured to engage the screw 30' such that rotation of the screw 30' in a first direction of rotation R1 is prevented until a first minimum torque value, for example the sufficient torque T, is applied to the screw 30. The ratchet 120' is further configured to engage the screw 30' such that rotation of the screw 30' in a second direction of rotation R2 is prevented until a second minimum torque value, for example the sufficient torque T', is applied to the screw 30'.

In one embodiment the first minimum torque value is the same as the second minimum torque value. In another embodiment the first minimum torque value is different than the second minimum torque value. In another embodiment the second minimum torque value is greater than the first minimum torque value. In another embodiment the second minimum torque value is less than the first minimum torque value.

Referring to FIGS. 12A-12C and 14A-14B, in one embodiment, the ratchet 120' can include a ratchet body 122" that includes a ratchet tab 126" that is configured to be connected to the distractor 20' such that the ratchet tab 126" is translationally and rotationally secured to the sleeve 90 such that translation of the ratchet 120' along the axis of rotation R relative to the sleeve 90 and rotation of the ratchet 120' about the axis of rotation R relative to the sleeve 90 are both prevented. Additionally, the ratchet tab 126" is translationally secured and rotatable relative to the screw 30' such that translation of the ratchet 120' along the axis of rotation R relative to the screw 30' is prevented, but rotation of the ratchet 120' about the axis of rotation R relative to the screw 30' is permitted.

The ratchet body 122" can further include a first collar member 124" and a second collar member 128", each configured to secure the ratchet tab 126" to the distractor 20' such that 1) the ratchet tab 126" is translationally and rotationally secured to the sleeve 90 relative to the axis of rotation R; and 2) the ratchet tab 126" is translationally secured and rotatable relative to the screw 30' with respect to the axis of rotation R.

The ratchet tab 126", the first collar member 124", and the second collar member 128" are similar to the ratchet tab 126', first collar member 124', and second collar member 128', respectively, (described in detail in reference to FIGS. 13A-13C above) in many aspects such that the description of the ratchet tab 126', first collar member 124', and second collar member 128' herein can be applied to the ratchet tab 126", the first collar member 124", and the second collar member 128". Differences between the ratchet tab 126' and the ratchet tab 126", the first collar member 124' and the first collar member 124", and the second collar member 128' and the second collar member 128" are highlighted below.

The ratchet body 122" can include one or more projections 292" and corresponding recesses 294", each recess 294" configured to receive one of the one or more projections 292 when the ratchet tab 126", the first collar member 124", and the second collar member 128" are properly aligned. As shown in the illustrated embodiment, the ratchet tab 126" can include one of the one or more projections 292" and the second collar member 128" can include the recess 294" configured to receive the projection 292" of the ratchet tab 126". The projection 292" and the recess 294" can be positioned, for example, so as to replace the gap 156' of the ratchet tab 126' and the first projection 274' of the second collar member 128', respectively.

As shown in the illustrated embodiment, the second collar member 128" can include one of the one or more projections 292" and the first collar member 124" can include the recess 294" configured to receive the projection 292" of the second collar member 128". The projection 292" of the second collar member 128" can be positioned, for example, on a projection, for example the second projection 276" of the second collar member 128" such that the second projection 276" is a two stage projection. The recess 294" of the first collar member 124" can be positioned, for example, so as to replace the second recess 246' of the second collar member 128'.

According to one embodiment, the ratchet 120' can be assembled by aligning the components of the ratchet body 122" such that the one or more projections 292" of the ratchet body 122" are each aligned with and then inserted into a corresponding one of the recesses 294" of the ratchet body 122". For example, the ratchet 120' can be assembled by aligning the projection 292" of the ratchet tab 126" with the recess 294" of the second collar member 128", aligning the projection 292" of the second collar member 128" with the recess 294" of the first collar member 124", and then simultaneously inserting the projection 292" of the ratchet tab 126" and the projection 292" of the second collar member 128" into the recess 294" of the second collar member 128" and the recess 294" of the first collar member 124", respectively.

Referring to FIG. 15A, the bone distraction system 10 defines a first orientation, for example a neutral orientation, in which the screw 30' and the ratchet 120' are prevented from rotating relative to one another with respect to the axis of rotation R until either: 1) a sufficient torque T is applied in the first direction of rotation R1 to the screw 30' or 2) a sufficient torque T' is applied in the second direction of rotation R2 to the screw 30'.

In the first orientation the inner surface 192' of one of the boom arm portions 150' abuts one of the flats 358 of the screw 30' thereby blocking rotation of the screw 30' relative to the ratchet 120' in both the first direction of rotation R1 and the second direction of rotation R2. In one embodiment, in the first orientation the inner surface 192' of each of the boom arm portions 150', for example the pair of boom arm portions 150', each abuts a respective one of the flats 358 of the screw 30' thereby blocking rotation of the screw 30' relative to the ratchet 120' in both the first direction of rotation R1 and the second direction of rotation R2. The bone distraction system 10 can be configured such that when the inner surface 192' of one of the pair of boom arm portions 150' engages one of the flats 358 and the inner surface 192' of the other of the pair of boom arm portions 150' engages another of the flats 358 simultaneously, micro motion of the distractor 20', relatively small amounts of rotation of the screw 30' relative to the sleeve 90 about the axis of rotation R, is prevented.

Referring to FIGS. 15A and 15B, the bone distraction system 10 defines a second orientation in which the screw 30' rotates relative to the ratchet 120' about the axis of rotation R, in the first direction of rotation R1. A sufficient torque T is applied to the screw 30' in the first direction of rotation R1 so as to overcome the resistance to rotation provided by interference between the inner surface 192' and the first flat 358a and place the bone distraction system in the second orientation. In the second orientation, the screw 30' is rotatable relative to the ratchet 120' about the axis of rotation R in the first direction of rotation R1 as long as the sufficient torque T is applied to the screw 30'. The tip portion 184' of the boom arm portion 150' is configured to flex radially outward with respect to the ratchet axis 136' upon application of the sufficient torque T to the screw 30'. As shown, the screw 30', for example the first flat 358a, rides along the tip portion 184', for example the intermediate surface 195', causing the tip portion 184' of the ratchet 120' to cam over the screw 30'.

As the screw 30' is rotated relative to the ratchet 120' in the first direction of rotation R1, the inner surface 192' cams over the screw 30' until the second flat 358b abuts the inner surface 192'. Once the inner surface 192' abuts the second flat 358b, the bone distraction system 10 is once again in the first orientation as described above (and illustrated in FIG. 15A), except that the inner surface 192' abuts the second flat 358b and not the first flat 358a.

Referring to FIGS. 15A and 15C, the bone distraction system 10 defines a third orientation in which the screw 30' rotates relative to the ratchet 120' about the axis of rotation R, in the second direction of rotation R2. A sufficient torque T' is applied to the screw 30' in the second direction of rotation R2 so as to overcome the resistance to rotation provided by interference between the inner surface 192' and the first flat 358a and place the bone distraction system in the third orientation. In the third orientation, the screw 30' is rotatable relative to the ratchet 120' about the axis of rotation R in the second direction of rotation R2 as long as the sufficient torque T' is applied to the screw 30'. The tip portion 184' of the boom arm portion 150' is configured to flex radially outward with respect to the ratchet axis 136' upon application of the sufficient torque T' to the screw 30'. As shown, the screw 30', for example the first flat 358a, rides along the tip portion 184', for example the inner surface 192', causing the tip portion 184' of the ratchet 120' to cam over the screw 30'.

As the screw 30' is rotated relative to the ratchet 120' in the second direction of rotation R2, the inner surface 192' cams over the screw 30' until the third flat 358c abuts the inner surface 192'. Once the inner surface 192' abuts the third flat 358c, the bone distraction system 10 is once again in the first orientation as described above (and illustrated in FIG. 15A), except that the inner surface 192' abuts the third flat 358c and not the first flat 358a.

Referring to FIGS. 15B and 15C, in one embodiment, interference between the first side wall 280' of the first projection 274' of the second collar member 128' and the first surface 152' of the ratchet tab 126' can prevent relative rotation of components of the ratchet 120', for example the ratchet tab 126' and the second collar member 128' when the screw 30' is rotated, for example in the first direction of rotation R1, relative to the ratchet 120'. The ratchet 120' can be further configured such that interference between the second side wall 282' of the first projection 274' of the second collar member 128' and the second surface 154' of the ratchet tab 126' can prevent relative rotation of components of the ratchet 120', for example the ratchet tab 126' and the second collar member 128' when the screw 30' is rotated, for example in the second direction of rotation R2, relative to the ratchet 120'. The ratchet 120' can include additional projections, configured to prevent relative rotation of the parts of the ratchet 120' when the ratchet 120' is assembled as described above. For example, the first collar member 124' can define a first projection 257' and a second projection 259' that are each configured to abut the ratchet tab 126' to prevent relative rotation of the first collar member 124' and the ratchet tab 126'.

Referring to FIGS. 15A-15C, in one embodiment the sufficient torques T and T' needed to rotate the screw 30' relative to the ratchet 120' about the axis of rotation R in the first direction of rotation R1 and the second direction of rotation R2, respectively, is equal to about 0.05 N-m.

Referring to FIGS. 16A-16C, in one embodiment the bone distraction system 10 can include a distractor 2020 that is constructed so as to define an engaged configuration and a disengaged configuration as described in greater detail below. The distractor 2020 includes a distractor axis 2022, that according to one embodiment the distractor 2020 is elongate along. The distractor axis 2022 can be a straight line, as shown, that extends centrally through the distractor 2020 in the longitudinal direction L.

The distractor 2020 includes a distractor body 2024, the distractor body 2024 having a screw 2030 and a sleeve 2090 that are configured to be connected to one another such that the screw 2030 is rotatable relative to the sleeve 2090 about the distractor axis 2022. The screw 2030 is similar to the screw 30 in many aspects such that the description of the screw 30 herein can be applied to the screw 2030 with differences between the screw 30 and the screw 2030 highlighted below.

The screw 2030 includes a screw body 2032 having a first portion 2034 and a second portion 2036. The first portion 2034 includes an actuation mechanism 2038 configured to receive a torque T that rotates the screw 2030 about an axis of rotation R when the screw 2030 is connected to the sleeve 2090. The axis of rotation R can be coincident with the distractor axis 2022, as shown in the illustrated embodiment. In another embodiment the axis of rotation R can be displaced from the distractor axis 2022. The second portion 2036 includes a shaft 2040 having external threads 2042. The screw 2030 can be configured to be connected to the sleeve 2090 such that the second portion 2036 is disposed within a sleeve borehole 2098 and the first portion 2034 is disposed outside of the sleeve borehole 2098.

The screw 2030 can include a third portion 2054 that includes a screw ratchet surface 2056. The screw ratchet surface 2056 is configured to engage a corresponding sleeve ratchet surface 2156 such that interference between the screw ratchet surface 2056 and the sleeve ratchet surface 2156 restricts relative rotation of the sleeve 2090 and the screw 2030 about the axis of rotation R. In one embodiment, the screw ratchet surface 2056 defines a ring shaped cross-section with respect to a plane that is normal to the distractor axis 2022. The screw ratchet surface 2056 can define a plurality of peaks 2058 and valleys 2060, as shown in the illustrated embodiment. The screw ratchet surface 2056 can further include a plurality of teeth 2062, each of the plurality of teeth 2062 including a first surface 2064 that extends from one of the plurality of valleys 2060 to one of the plurality of peaks 2058, and a second surface 2066 that extends from the one of the plurality of peaks 2058 to another one of the plurality of valleys 2060 that is adjacent to the one of the plurality of valleys 2060. In one embodiment the first and second surfaces 2064 and 2066 each taper linearly from the respective peak 2058 to each of the respective valleys 2060. In another embodiment, at least one of the first and second surfaces 2064 and 2066 can taper non-linearly from the respective peak 2058 to the respective valley 2060.

The distractor 2020 defines a straight line 2068 that, in one embodiment, passes through one of the plurality of peaks 2058 and extends in a direction that is perpendicular to the distractor axis 2022. The screw ratchet surface 2056 can be described as including a first angle $\Theta 1$ (theta 1) that is defined between the straight line 2068 and the first surface 2064. The first angle $\Theta 1$ (theta 1) can be between from about 0° to about 90° including any angle inbetween, for example about 45°. The screw ratchet surface 2056 can be described as including a second angle $\Theta 2$ (theta 2) that is defined between the straight line 2068 and the second surface 2066. The second angle $\Theta 2$ (theta 2) can be between from about 0° to about 90° including any angle inbetween, for example about 45°.

As shown in the illustrated embodiment, the third portion 2054 can be disposed within the first portion 2034 such that when the screw 2030 and sleeve 2090 are assembled to form the distractor 2020, the third portion 2054 is positioned outside the sleeve borehole 2098 of the sleeve 2090. In another embodiment the third portion 2054 can be disposed within the second portion 2036 such that when the screw 2030 and sleeve 2090 are assembled to form the distractor 2020, the third portion 2054 is positioned inside the sleeve borehole 2098 of the sleeve 2090. In yet another embodiment the third portion 2054 can be disposed between the first portion 2034 and the second portion 2036 such that when the screw 2030 and sleeve 2090 are assembled to form the distractor 2020, the third portion 2054 is positioned partially inside the sleeve borehole 2098 and partially outside the sleeve borehole 2098.

The sleeve 2090 includes a sleeve body 2096 and a sleeve borehole 2098 that extends through the sleeve body 2096 between a first end 2092 and a second end 2094 (not shown), for example from the first end 2092 to the second end 2094. The sleeve body 2096 includes an outer surface 2100 that extends between the first end 2092 and the second end 2094. The sleeve body 2096 further includes an inner surface 2102 that is opposite the outer surface 2100 and that extends between the first end 2092 and the second end 2094 such that the inner surface 2102 at least partially defines the sleeve borehole 2098. The sleeve 2090 defines a slot 2104 (not shown) that extends through the sleeve body 2096 in a direction perpendicular to the distractor axis 2022 from the outer surface 2100 to the inner surface 2102 such that the sleeve borehole 2098 is open to an exterior of the sleeve 2090 through the slot 2104. The slot 2104 is similar to the slot 104 as described herein.

The sleeve 2090 can include a sleeve ratchet surface 2156 that is configured to engage the screw ratchet surface 2056 such that interference between the screw ratchet surface 2056 and the sleeve ratchet surface 2156 restricts relative rotation of the sleeve 2090 and the screw 2030 about the axis of rotation R. In one embodiment, the sleeve ratchet surface 2156 defines a ring shaped cross-section with respect to a plane that is normal to the distractor axis 2022. The sleeve ratchet surface 2156 can define a plurality of peaks 2158 and valleys 2160, as shown in the illustrated embodiment.

The sleeve ratchet surface 2156 can further include a plurality of teeth 2162, each of the plurality of teeth 2162 including a first surface 2164 that extends from one of the plurality of valleys 2160 to one of the plurality of peaks 2158, and a second surface 2166 that extends from the one of the plurality of peaks 2158 to another one of the plurality of valleys 2160 that is adjacent to the one of the plurality of valleys 2160. In one embodiment the first and second surfaces 2164 and 2166 each taper linearly from the respective peak 2158 to each of the respective valleys 2160. In another embodiment, at least one of the first and second surfaces 2164 and 2166 can taper non-linearly from the respective peak 2158 to the respective valley 2160.

The straight line 2068 can, as shown in the illustrated embodiment, pass through one of the plurality of valleys 2160. The sleeve ratchet surface 2156 can be described as including a third angle Θ3 (theta 3) that is defined between the straight line 2068 and the second surface 2166. The third angle Θ3 (theta 3) can be between from about 0° to about 90° including any angle inbetween, for example about 45°. The sleeve ratchet surface 2156 can be described as including a fourth angle Θ4 (theta 4) that is defined between the straight line 2068 and the first surface 2164. The fourth angle Θ4 (theta 4) can be between from about 0° to about 90° including any angle inbetween, for example about 45°.

In one embodiment, the first angle Θ1 (theta 1) is substantially equal to the third angle Θ3 (theta 3). In one embodiment, the second angle Θ2 (theta 2) is substantially equal to the fourth angle Θ4 (theta 4). In one embodiment, the first angle Θ1 (theta 1) is substantially equal to the third angle Θ3 (theta 3) and the second angle Θ2 (theta 2) is substantially equal to the fourth angle Θ4 (theta 4) such that the screw ratchet surface 2056 and the sleeve ratchet surface 2156 define substantially the same shape.

The distractor 2020 is constructed so as to define an engaged configuration and a disengaged configuration. In the disengaged configuration the screw ratchet surface 2056 is spaced apart from the sleeve ratchet surface 2156 along the distractor axis 2022 such that the screw 2030 is rotatable relative to the sleeve 2090 with respect to the axis of rotation R, without applying a sufficient torque T or T' to the screw 2030. In the disengaged configuration any torque T applied to the screw 2030 will rotate the screw 2030 in the first direction of rotation R1 relative to the sleeve 2090, and any torque T' applied to the screw 2030 will rotate the screw 2030 in the second direction of rotation R2 relative to the sleeve 2090.

In the engaged configuration the screw ratchet surface 2056 abuts the sleeve ratchet surface 2156 such that the screw 2030 is rotatable relative to the sleeve 2090 with respect to the axis of rotation R only once a sufficient torque T or T' is applied to the screw 2030. In the engaged configuration prior to the sufficient torque T being applied to the screw 2030 the screw 2030 will not rotate in the first direction of rotation R1 relative to the sleeve 2090. Additionally, prior to the sufficient torque T' being applied to the screw 2030 the screw 2030 will not rotate in the second direction of rotation R2 relative to the sleeve 2090.

The distractor 2020 can further include a biasing element 2300 and a collar 2400. The biasing element 2300 is configured to provide a biasing force that biases the distractor 2020 into the engaged configuration. The collar 2400 includes a first end 2402, a second end 2404, and a collar body 2406 that extends from the first end 2402 to the second end 2404. The collar 2400 further includes an inner cavity 2408 that extends from the first end 2402 into the collar body 2406 toward the second end 2404, and terminates at a base surface 2410. The base surface 2410 includes an opening 2412 that is configured to receive the screw 2030.

The collar 2400 is configured to be secured to the distractor 2020 such that the screw ratchet surface 2056 and the sleeve ratchet surface 2156 are both positioned within the inner cavity 2408. In one embodiment the biasing element 2300 includes a spring 2302 that provides a force that biases the screw ratchet surface 2056 toward the sleeve ratchet surface 2156. In one embodiment, the distractor 2020 defines an assembled configuration in which 1) the screw 2030 is passed through the spring 2302; 2) the collar 2400 is secured to the sleeve 2090 such that the spring 2302, the screw ratchet surface 2056, and the sleeve ratchet surface 2156 are all positioned within the inner cavity 2408; and 3) the spring 2302 is captured between the third portion 2054 of the screw 2030 and the base surface 2410 of the collar 2400.

In use, the spring 2302 biases the screw ratchet surface 2056 into abutment with the sleeve ratchet surface 2156 so that the distractor 2020 is biased into the engaged configuration. A force that is greater than the biasing force of the spring 2302 can be applied to first portion 2034 of the screw 2030 along the distractor axis 2022 in a direction away from the sleeve 2090 to separate the screw ratchet surface 2056 and the sleeve ratchet surface 2156 so that the distractor 2020 is in the disengaged configuration.

In the engaged configuration, rotation of the screw 2030 relative to the sleeve 2090 in the first direction of rotation R1 is resisted by the abutment of the first surface 2064 of the plurality of teeth 2062 with the second surface 2166 of the plurality of teeth 2162. And in the engaged configuration, rotation of the screw 2030 relative to the sleeve 2090 in the second direction of rotation R2 is resisted by the abutment of the second surface 2066 of the plurality of teeth 2062 with the first surface 2164 of the plurality of teeth 2162. The distractor 2020 can be constructed such that desired values for the sufficient torque T and T' are achieved.

For example, the larger the first angle Θ1 (theta 1) and the third angle Θ3 (theta 3) the smaller the value for the sufficient torque T that is required to rotate the screw 2030 relative to the sleeve 2090 in the first direction of rotation R1 about the distractor axis 2022. Similarly, the larger the second angle Θ2 (theta 2) and the fourth angle Θ4 (theta 4) the smaller the value for the sufficient torque T' that is required to rotate the screw 2030 relative to the sleeve 2090 in the second direction of rotation R2 about the distractor axis 2022. Likewise, the smaller the first angle Θ1 (theta 1) and the third angle Θ3 (theta 3) the larger the value for the sufficient torque T that is required to rotate the screw 2030 relative to the sleeve 2090 in the first direction of rotation R1 about the distractor axis 2022, and the smaller the second angle Θ2 (theta 2) and the fourth angle Θ4 (theta 4) the larger the value for the sufficient torque T' that is required to rotate the screw 2030 relative to the sleeve 2090 in the second direction of rotation R2 about the distractor axis 2022.

In one embodiment, the distractor 2020 can be constructed such that the first angle Θ1 (theta 1) and the third angle Θ3 (theta 3) are both greater than each of the second angle Θ2 (theta 2) and the fourth angle Θ4 (theta 4), thus setting the value for the sufficient torque T to be less than the value of the sufficient torque T'. In another embodiment, the distractor 2020 can be constructed such that the first angle Θ1 (theta 1) and the third angle Θ3 (theta 3) are both less than each of the second angle Θ2 (theta 2) and the fourth angle Θ4 (theta 4), thus setting the value for the sufficient torque T to be greater than the value of the sufficient torque T'.

In one embodiment, the distractor 2020 can be constructed such that the first angle Θ1 (theta 1) and the third angle Θ3 (theta 3) are both 0°, thus preventing the screw 2030 from rotating relative to the sleeve 2090 in the first direction of rotation R1 about the distractor axis 2022 regardless of the value of the torque T that is applied to the screw 2030. In another embodiment, the distractor 2020 can be constructed such that the second angle Θ2 (theta 2) and the fourth angle Θ4 (theta 4) are both 0°, thus preventing the screw 2030 from rotating relative to the sleeve 2090 in the second direction of rotation R2 about the distractor axis 2022 regardless of the value of the torque T' that is applied to the screw 2030.

Referring to FIGS. 1 and 17A-17D, according to one embodiment the bone distraction system 10 can include a distractor 2020', a friction assembly 2120', the first footplate 320, and the second footplate 420. According to one embodiment, the distractor 2020' includes a screw 2030' and a sleeve 2090' that are configured to be connected to each other such that the screw 2030' is rotatable relative to the sleeve 2090' about the axis of rotation R, and vice versa. The distractor 2020' is similar to the distractor 2020 (described in detail in reference to FIGS. 16A-16C above) in many aspects such that the description of the distractor 2020 herein can be applied to the distractor 2020'. Generally speaking, the distractor 2020' is similar to the distractor 2020 except that wherein the screw ratchet surface 2056 and the sleeve ratchet surface 2156 define peaks and valleys in distractor 2020, the mating surfaces of the friction assembly 2120' and the sleeve 2090' are devoid of peaks and valleys. This and other differences between the distractor 2020 and the distractor 2020' are highlighted below.

The bone distraction system 10 is configured to be attached to the first bone segment 2a and the second bone segment 2b such that actuation of the bone distraction system 10 adjusts the gap 3 between the first bone segment 2a and the second bone segment 2b. As shown in the illustrated embodiment, the first footplate 320 is configured to be attached to the first bone segment 2a and the second footplate 420 is configured to be attached to the second bone segment 2b, such that actuation of the distractor 2020 adjusts a distance D between the first footplate 320 and the second footplate 420 which adjusts the size of the gap 3 between the first bone segment 2a and the second bone segment 2b.

The distractor 2020' is elongate along a distractor axis 2022' and includes a distractor body 2024'. In one embodiment, the distractor axis 2022' is a straight line extending in the longitudinal direction L. In another embodiment the distractor axis 2022' extends centrally through the distractor 2020'. The distractor body 2024' includes the screw 2030' and the sleeve 2090' that are configured to be connected to one another such that the screw 2030' is rotatable relative to the sleeve 2090' about the distractor axis 2022'.

The screw 2030' includes a screw body 2032' having a first portion 2034' and a second portion 2036'. The first portion 2034' includes an actuation mechanism 2038' configured to receive a torque T that rotates the screw 2030' about an axis of rotation R when the screw 2030' is connected to the sleeve 2090'. In one embodiment the distractor 2020' is configured such that the torque T is applied in a first direction of rotation R1 to rotate the screw 2030' about the axis of rotation R in the first direction of rotation R1. The distractor 2020' can further be configured such that the screw 2030' is configured to receive a torque T' applied in a second direction of rotation R2, for example opposite the first direction of rotation R1, to rotate the screw 2030' about the axis of rotation R in the second direction of rotation R2.

As shown in the illustrated embodiment, the axis of rotation R can be coincident with the distractor axis 2022'. In another embodiment the axis of rotation R can be displaced from the distractor axis 2022'. In one embodiment the second portion 2036' includes a shaft 2040' having external threads 2042'. As shown in the illustrated embodiment, the screw 2030' is configured to be connected to the sleeve 2090' such that the second portion 2036' is disposed within the sleeve borehole 2098' and the first portion 2034' is disposed outside of the sleeve borehole 2098'.

The distractor 2020' can include a plurality of footplates, for example the first footplate 320 and the second footplate 420 as described in detail above in reference to FIGS. 2A and 2B. According to one embodiment, the first footplate 320 and the second footplate 420 are configured to be secured to the screw 2030' and the sleeve 2090' as described above in reference to the screw 30 and the sleeve 90 as illustrated in FIGS. 2A and 2B.

As shown in the illustrated embodiment the friction assembly 2120' includes an assembly body 2122' which includes, in accordance with one embodiment, a friction member 2124' and a biasing member 2126'. In one embodiment, the friction assembly 2120' is configured to be secured to the distractor body 2024' such that the sleeve 2090' and the friction member 2124' are translationally secured relative to one another such that the sleeve 2090' and the friction member 2124' cannot translate relative to each other along the axis of rotation R. In another embodiment, the friction assembly 2120' is configured to be secured to the distractor body 2024' such that the screw 2030' is translatable relative to both the sleeve 2090' and the friction member 2124'. For example compressing the biasing member 2126' could allow the screw 2030' to translate relative to both the sleeve 2090' and the friction member 2124' along the axis of rotation R. In another embodiment, the friction assembly 2120' is rotationally secured to the sleeve 2090' such that the friction member 2124' and the sleeve 2090' cannot rotate relative to each other about the axis of rotation R, and the screw 2030' is rotatable relative to both the friction member 2124' and the sleeve 2090' about the axis of rotation R.

In one embodiment the friction assembly 2120' is configured to be secured to the distractor body 2024' such that a portion of the friction assembly 2120', for example the biasing member 2126' biases a portion of the screw 2030' toward and into contact with the sleeve 2090' creating a friction force. The friction force restricts relative rotation of the sleeve 2090' and the screw 2030' such that a minimum torque value, referred to herein as a sufficient torque Ti, must be applied to the screw 2030' to rotate the screw 2030' relative to the sleeve 2090', or vice versa, about the axis of rotation R.

In one embodiment the friction assembly 2120' and the screw 2030' are configured such that the minimum torque value required to rotate the screw 2030' relative to the sleeve 2090' in the first direction of rotation R1, for example clockwise, is the same as the minimum torque value required to rotate the screw 2030' relative to the sleeve 2090' in the second direction of rotation R2, for example counterclockwise. In another embodiment the friction assembly 2120' and the screw 2030' are configured such that the minimum torque value required to rotate the screw 2030' relative to the sleeve 2090' in the first direction of rotation R1 is different than the minimum torque value required to rotate the screw 2030' relative to the sleeve 2090' in the second direction of rotation R2. In one embodiment rotation of the screw 2030' relative to the sleeve 2090' in the first direction of rotation R1 actuates the distractor 2020' so as to distract the distractor 2020', and rotation of the screw 2030' relative to the sleeve 2090' in the second direction actuates the distractor so as to contract the distractor 2020'.

As shown in the illustrated in embodiment, the screw 2030' can be elongate along a screw axis 2044'. The screw 2030' defines a first end 2046' and a second end 2048' spaced from the first end 2046' along the screw axis 2044' in a first direction. The screw body 2032' extends from the first end 2046' to the second end 2048'. In one embodiment the screw body 2032' can include a first portion 2034' and a second portion 2036'. As shown, the first portion 2034' extends from the first end 2046' toward the second end 2048', and the second portion 2036' extends from the second end 2048' toward the first end 2046'. In one embodiment the first portion 2034' extends from the first end 2046' to the second portion 2036', and the second portion 2036' extends from the second end 2048' to the first portion 2034'.

The first portion 2034' includes an actuation mechanism 2038' that is configured to receive a torque T that rotates the screw 2030' about the axis of rotation R. As shown in the illustrated embodiment, the axis of rotation R can be the screw axis 2044'. The first portion 2034' can further include a shoulder portion 2050', the shoulder portion 2050' including a first abutment surface 2052' and a second abutment surface 2053'. The first abutment surface 2052' faces the second end 2048' of the screw 2030' and the second abutment surface 2053' faces the first end 2046' of the screw 2030'. The shoulder portion 2050' defines an outer dimension D7 measured in a direction perpendicular to the axis of rotation R along a straight line that passes through the axis of rotation R. As shown, the shoulder portion 2050', the first abutment surface 2052', and the second abutment surface 2053' each define a circular shape such that the outer dimension D7 is a diameter. In another embodiment any or all of the shoulder portion 2050', the first abutment surface 2052', and the second abutment surface 2053' can define a non-circular shape.

The screw 2030' can further include a third portion 2054' that defines an outer dimension D8. According to one embodiment, the outer dimension D8 of the third portion 2054' is smaller than the outer dimension D7 of the shoulder portion 2050'. According to another embodiment, the outer dimension D8 of the third portion 2054' is greater than the outer dimension D7 of the shoulder portion 2050'.

As shown in the illustrated embodiment, the third portion 2054' can be disposed within the first portion 2034' such that when the screw 2030' and sleeve 2090' are assembled to form the distractor 2020', the third portion 2054' is positioned outside the sleeve borehole 2098' of the sleeve 2090'. In another embodiment the third portion 2054' can be disposed within the second portion 2036' such that when the screw 2030' and sleeve 2090' are assembled to form the distractor 2020', the third portion 2054' is positioned inside the sleeve borehole 2098' of the sleeve 2090'. In yet another embodiment the third portion 2054' can be disposed between the first portion 2034' and the second portion 2036' such that when the screw 2030' and sleeve 2090' are assembled to form the distractor 2020', the third portion 2054' is positioned partially inside the sleeve borehole 2098' and partially outside the sleeve borehole 2098'.

The friction assembly 2120', as shown in the illustrated embodiment, includes an assembly body 2122' that includes a friction member 2124' and a biasing member 2126'. The friction member 2124' defines a first end 2128', a second end 2130', a friction member body 2132' that extends from the first end 2128' to the second end 2130', and a friction member through hole 2134' that extends through the friction member body 2132' from the first end 2128' to the second end 2130'. The friction member body 2132' includes an outer surface 2136' and an inner surface 2138' that is opposite the outer surface 2136'. The inner surface 2138', as shown, defines the friction member through hole 2134'.

The friction member 2124' includes a first portion 2140' proximate the first end 2128' and a second portion 2142' proximate the second end 2130'. The first portion 2140' of the friction member 2124' defines an inner dimension D9 of the friction member through hole 2134' and the second portion 2142' defines an inner dimension D10 of the friction member through hole 2134'. According to one embodiment, the inner dimension D9 of the first portion 2140' is smaller than the inner dimension D10 of the second portion 2142'. According to another embodiment, the inner dimension D9 of the first portion 2140' can be greater than the inner dimension D10 of the second portion 2142'. The friction member body 2132' can include an abutment surface 2144' configured to receive a biasing force from the biasing member 2126'. As shown, the inner surface 2138' can define the abutment surface 2144', for example at the intersection of the first portion 2140' and the second portion 2142'.

The biasing member 2126' can include a spring 2146' that is configured to provide a biasing force F. As shown, the spring 2146' is configured to be compressed thereby generating the biasing force F within the spring 2146'. The spring 2146' includes a first end 2148', a second end 2150', and a length L2 measured from the first end 2148' to the second end 2150'. Prior to assembly of the friction assembly 2120', when the spring 2146' is devoid of outside forces acting upon the spring 2146', the length L2 is the natural length of the spring 2146' and the biasing force F is zero.

According to one embodiment, the friction assembly 2120' is configured to be assembled with the distractor 2020' as described below. The spring 2146' is positioned within the friction member through hole 2134' such that the first end 2148' of the spring 2146' abuts the abutment surface 2144' of the friction member 2124'. The first portion 2034' of the screw 2030' can then be inserted through the spring 2146' and the friction member through hole 2134' until the second end 2150' of the spring 2146' abuts the second abutment surface 2053', thereby capturing the spring 2146' between the abutment surface 2144' and the second abutment surface 2053'. The captured spring 2146' is compressed such that the length L2 of the captured spring is less than the natural length of the spring 2146'. The compression of the length L2 of the spring 2146' results in the application of the biasing force F to the abutment surface 2144' and the second abutment surface 2053'.

The shaft 2040' of the screw 2030' is configured to be inserted through the first opening 2106' of the sleeve borehole 2098 until both the first abutment surface 2052' of the screw 2030' and the second end 2130' of the friction member 2124' abut the abutment surface 2110' of the sleeve 2090'. The friction assembly 2120' can then be secured to the distractor 2020' such that the friction assembly 2120' and the distractor 2020' are prevented from translating with respect to one another, for example along the distractor axis 2022'. In one embodiment, the friction assembly 2120' can be secured to the distractor 2020' such that the friction assembly 2120' and the distractor 2020' also are prevented from rotating with respect to one another, for example about the distractor axis 2022'. For example, the second end 2130' of the friction member 2124' can be welded to the abutment surface 2110' of the sleeve 2090' to secure the friction assembly 2120' to the distractor 2020'.

Once the friction assembly 2120' is assembled with the distractor 2020', for example, such that the second end 2130' of the friction member 2124' is welded to the abutment surface 2110' of the sleeve 2090' as described above, the biasing force F applied by the spring 2146' biases the first abutment surface 2052' of the screw 2030' into contact with the abutment surface 2110' of the sleeve 2090' thereby creating friction that resists rotation of the screw 2030' relative to the sleeve 2090' about the axis of rotation R. To overcome the friction between the first abutment surface 2052' and the abutment surface 2110', the sufficient torque T, must be applied to the screw 2030' to rotate the screw 2030' relative to the sleeve 2090' in a first direction about the axis of rotation R. To overcome the friction between the first abutment surface 2052' and the abutment surface 2110', the sufficient torque T', must be applied to the screw 2030' to rotate the screw 2030' relative to the sleeve 2090' in a second direction about the axis of rotation R.

According to one embodiment, T and T' are equal such that the same minimum amount of torque is needed to overcome the friction between the first abutment surface 2052' and the abutment surface 2110' to rotate the screw 2030' relative to the sleeve 2090' in either the first direction about the axis of rotation R or the second direction about the axis of rotation R. For example one or both of the first abutment surface 2052' and the abutment surface 2110' can be coated with a surface treatment that is symmetric with respect to the first and second directions. According to another embodiment, T and T' are different such that the minimum amount of torque needed to overcome the friction between the first abutment surface 2052' and the abutment surface 2110' to rotate the screw 2030' relative to the sleeve 2090' in the first direction of rotation R1 about the axis of rotation R is different than the minimum amount of torque needed to overcome the friction between the first abutment surface 2052' and the abutment surface 2110' to rotate the screw 2030' relative to the sleeve 2090' in the second direction of rotation R2 about the axis of rotation R. For example one or both of the first abutment surface 2052' and the abutment surface 2110' can be coated with a surface treatment that is asymmetric with respect to the first and second directions of rotation R1 and R2.

Figure 17D:
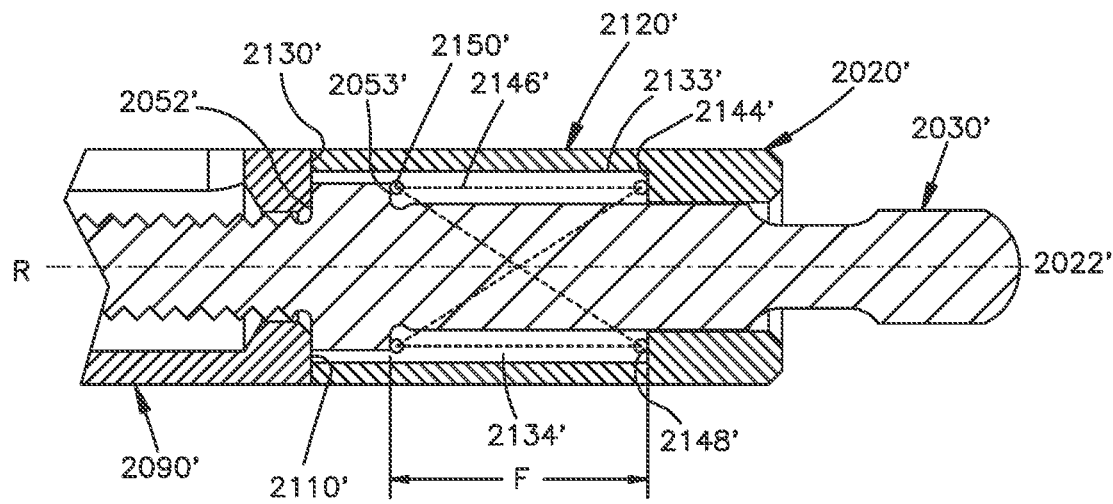
FIG. 17D is a cross sectional view of a portion of the distractor and friction assembly illustrated in FIG. 17A along line 17C-17C.
Figure 17E:
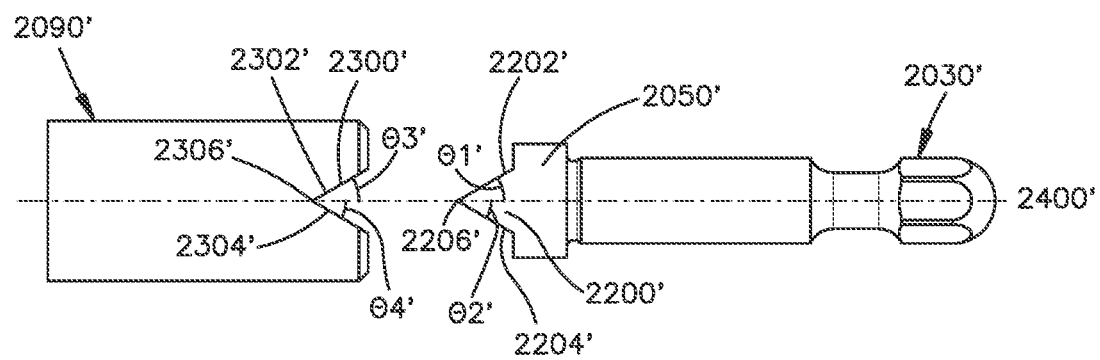
FIG. 17E is a top exploded view of a portion of the distractor and the friction assembly illustrated in FIG. 17A, according to another embodiment.
Figure 19D:
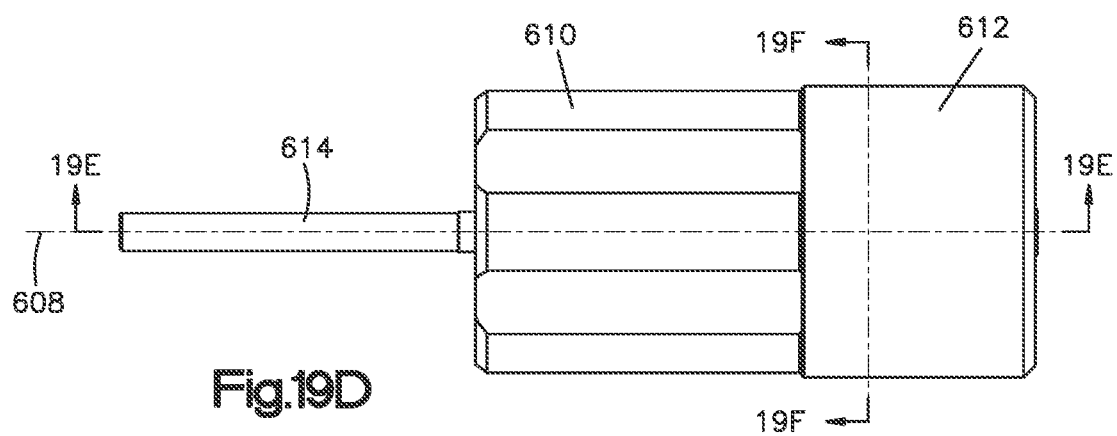
FIG. 19D is a top plan view of the instrument illustrated in FIG. 19A.
Figure 19E:
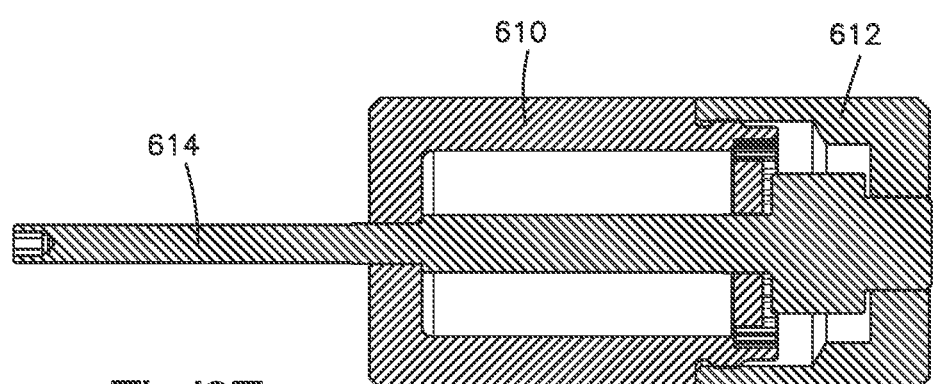
FIG. 19E is cross-sectional view of the instrument illustrated in FIG. 19D, along line 19E-19E.
Figure 19F:
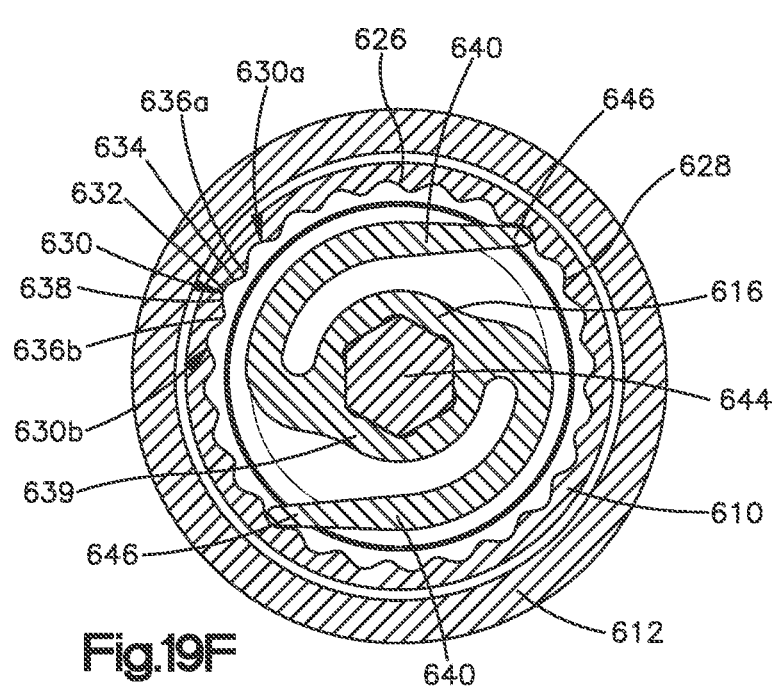
FIG. 19F is cross-sectional view of the instrument illustrated in FIG. 19D, along line 19F-19F.

Referring to FIG. 17E, the distractor 2020' can include at least one tooth 2200' (referred to herein as the tooth 2200') and at least one groove 2300' (referred to herein as the groove 2300') with a shape that corresponds to a shape of the tooth 2200'. The tooth 2200' includes a first surface 2202' that faces at least partially in the first direction of rotation R1, a second surface 2204' that faces at least partially in the second direction of rotation R2, and an apex 2206' between the first surface 2202' and the second surface 2204'. The tooth 2200' defines a first angle $\Theta1'$ (theta 1 prime) that is measured between a straight line 2400' (which passes through the apex 2206' and is parallel to the distractor axis 2022') and the first surface 2202'. The first angle $\Theta1'$ (theta 1 prime) can be between from about 0° to about 90° including any angle inbetween, for example about 45°. The tooth 2200' defines a second angle $\Theta2'$ (theta 2 prime) that is measured between the straight line 2400' and the second surface 2204'. The second angle $\Theta2'$ (theta 2 prime) can be between from about 0° to about 90° including any angle inbetween, for example about 45°. According to one embodiment, the tooth 2200' can be carried by the screw 2030', for example the tooth 2200' can be monolithic with the shoulder portion 2050', as shown. In another embodiment, the tooth 2200' can be carried by the sleeve 2090', for example the tooth 2200' can be monolithic with the sleeve 2090'.

According to one embodiment, the groove 2300' includes a first surface 2302' that faces at least partially in the first direction of rotation R1, a second surface 2304' that faces at least partially in the second direction of rotation R2, and an apex 2306' between the first surface 2302' and the second surface 2304'. The groove 2300' defines a third angle $\Theta3'$ (theta 3 prime) that is measured between a straight line (which passes through the apex 2306' and is parallel to the distractor axis 2022'), for example the straight line 2400' and the first surface 2302'. The third angle $\Theta3'$ (theta 3 prime) can be between from about 0° to about 90° including any angle inbetween, for example about 45°. The groove 2300' defines a fourth angle $\Theta4'$ (theta 4 prime) that is measured between the straight line 2400' and the second surface 2304'. The fourth angle $\Theta4'$ (theta 4 prime) can be between from about 0° to about 90° including any angle inbetween, for example about 45°. According to one embodiment, the groove 2300' can be carried by the sleeve 2090', for example the groove 2300' can be monolithic with the sleeve 2090', as shown. In another embodiment, the groove 2300' can be carried by the screw 2030', for example the groove 2300' can be monolithic with the shoulder portion 2050'.

Referring to FIGS. 2A and 18A, in one embodiment the bone distraction system 10 includes at least one instrument 500, for example a torque application instrument. The at least one instrument 500 can include a standard torque application instrument 502 configured to apply a torque to the screw 30. Although the at least one instrument 500 is described in relation to the screw 30, the at least one instrument 500 can be configured to apply a torque to any of the embodiments of the screw (30', 2030, 2030', etc.) described herein. The standard torque application instrument 502 includes a first end 504, a second end 506 spaced from the first end 504, and an instrument body 508 that extends from the first end 504 to the second end 506. The instrument body 508 can include a handle portion 510 proximate the first end 504 and a tip portion 512 proximate the second end 506. The handle portion 510 is configured to receive an input torque, for example from a human hand. The tip portion 512 includes a driving mechanism 514, for example an internal hex, that is configured to engage the actuation mechanism 38 of the screw 30 and output the torque from the handle portion 510 to the screw 30. The standard torque application instrument 502 is devoid of any torque limiting mechanisms, such that whatever input torque is received at the handle portion 510 is output by the tip portion 512 to the screw 30 when standard torque application instrument 502 is attached to the screw 30.

Referring to FIGS. 2A and 18B, in one embodiment the at least one instrument 500 can include a torque-limited torque application instrument 522 configured to apply a torque to the screw 30. The torque-limited torque application instrument 522 includes a first end 524, a second end 526 spaced from the first end 524, and an instrument body 528 that extends from the first end 524 to the second end 526. The instrument body 528 can include a handle portion 530 proximate the first end 524 and a tip portion 532 proximate the second end 526. The handle portion 530 is configured to receive an input torque, for example from a human hand. The tip portion 532 includes a driving mechanism 534, for example an internal hex, that is configured to engage the actuation mechanism 38 of the screw 30 and output the torque from the handle portion 530 to the screw 30. As shown, the torque-limited torque application instrument 522 includes a torque limiting mechanism 536.

According to one embodiment, the torque-limited torque application instrument 522 can define a maximum value for the output torque. In one embodiment the torque-limited torque application instrument 522 defines a first maximum value for the output torque in the first direction of rotation and a second maximum value for the output torque in the second direction of rotation. In one embodiment the first maximum value and the second maximum value are equal. In another embodiment the first maximum value is different than the second maximum value, for example the first maximum value can be greater than or less than the second maximum value.

In one embodiment the torque limiting mechanism 536 is configured so as to set each of the first and second maximum values to a respective selected torque value. Any amount of torque that is input to the handle portion 530 that is below the selected torque value will be output by the tip portion 532, for example to the screw 30 when the torque-limited torque application instrument 522 is attached to the screw 30 of the distractor 20. Any torque that is input at the handle portion 530 that exceeds the selected torque value will cause the handle portion 530 to slip, or rotate, relative to the tip portion 532. The slippage or rotation between the handle portion 530 and tip portion 532 prevents the tip portion 532 from outputting the amount of input torque that exceeds the selected torque value. The torque-limited torque application instrument 522 can include an adjustment mechanism 538 that allows the selected torque value to be adjusted as desired.

In one embodiment, the torque-limited torque application instrument 522 can be configured such that the selected torque value is greater than the sufficient torque T but less than the sufficient torque T'. For example, in one embodiment in which the sufficient torque T is 0.01 N-m and the sufficient torque T' is 0.05 N-m, the torque-limited torque application instrument 522 can be configured such that the selected torque value of the torque limiting mechanism 536 is between 0.01 N-m and 0.05 N-m, for example 0.03 N-m. The torque-limited torque application instrument 522 with a selected torque value that is between the sufficient torque T and the sufficient torque T' will be capable of actuating the distractor 20 such that the screw 30 rotates relative to the ratchet 120 in the first direction of rotation R1, but is incapable of actuating the distractor 20 such that the screw 30 rotates relative to the ratchet 120 in the second direction R2.

In another embodiment, the torque-limited torque application instrument 522 can be configured such that the selected torque value is greater than both the sufficient torque T and the sufficient torque T'. For example, in one embodiment in which the sufficient torque T is 0.01 N-m and the sufficient torque T' is 0.05 N-m, the torque-limited torque application instrument 522 can be configured such that the selected torque value of the torque limiting mechanism 536 is greater than 0.05 N-m, for example 0.1 N-m. The torque-limited torque application instrument 522 with a selected torque value that is greater than the sufficient torque T and is greater than the sufficient torque T' will be capable of actuating the distractor 20 such that the screw 30 rotates relative to the ratchet 120 in the first direction of rotation R1, and is capable of actuating the distractor 20 such that the screw 30 rotates relative to the ratchet 120 in the second direction R2.

Referring to FIGS. 19A-19F, the at least one instrument 500 of the system 10 can include a torque-limited torque application instrument 600 which is configured to apply a torque to the screw 30. The torque-limited torque application instrument 600 includes a first end 602, a second end 604, and a driver body 606 that extends from the first end 602 to the second end 604. According to one embodiment, the driver body 606 is elongate along an axis 608, which as shown can be a central axis. The driver body 606 includes a first sleeve member 610, a second sleeve member 612, a shaft member 614, and a ratchet tab 616. The torque-limited torque application instrument 600 defines an assembled configuration in which: 1) the torque-limited torque application instrument 600 is assembled such that the first sleeve member 610 is rotatable with respect to the ratchet tab 616 about the axis 608; and 2) the ratchet tab 616 is rotationally locked with respect to the shaft member 614 about the axis 608.

The driver body 606 includes a surface 618 configured to receive an input, for example a torque applied by the hands of a user of the torque-limited torque application instrument 600. As shown the surface 618 can be defined by an outer surface 620 of the first sleeve member 610. The driver body 606 further includes a transfer mechanism 622 configured to transfer an output, for example the torque applied by the hands of the user of the torque-limited torque application instrument 600. According to one embodiment, the transfer mechanism 622 can be defined by the shaft member 614. The transfer mechanism 622 can correspond in shape to the actuation mechanism 38 of the distractor 20. As shown, the transfer mechanism can be in the form of an internal hex drive 624.

The first sleeve member 610 includes an inner surface 626 that defines a ratchet surface 628. As shown the ratchet surface 628 includes a series of grooves 630. Each of the series of grooves 630 including an apex 632, a first surface 634 that extends between the apex 632 and an intersection 636a of the groove 630 and a first adjacent groove 630a, and a second surface 638 that extends between the apex 632 and an intersection 636b of the groove 630 and a second adjacent groove 630b.

The ratchet tab 616 includes a base portion 639 and a boom arm portion 640. The base portion 639 includes a hole 642 with a non-circular shape configured to receive a portion 644 of the shaft member 614 with a non-circular shape so as to couple the ratchet tab 616 to the shaft member 614 such that the ratchet tab 616 is rotationally locked with respect to the shaft member 614 about the axis 608. The boom arm portion 640 includes a tip portion 646 that is configured to engage the ratchet surface 628 of the first sleeve member 610. As shown, the ratchet tab 616 includes a plurality of boom arm portions 640, for example a pair of boom arm portions 640, each having a tip portion 646.

According to one embodiment, when the torque-limited torque application instrument 600 is in the assembled configuration, the tip portion 646 of the boom arm portion 640 abuts the ratchet surface 628 of the first sleeve member 610. As shown, the tip portion 646 of the boom arm portion 640 abuts the ratchet surface 628 of the first sleeve member 610 such that a first minimum torque value is defined, that is required to be applied to the first sleeve member 610 to rotate the first sleeve member 610 relative to the ratchet tab 616 in the first direction of rotation R1 about the axis 608. Further in the embodiment of the torque-limited torque application instrument 600 as shown, the tip portion 646 of the boom arm portion 640 abuts the ratchet surface 628 of the first sleeve member 610 such that a second minimum torque value is defined, that is required to be applied to the first sleeve member 610 to rotate the first sleeve member 610 relative to the ratchet tab 616 in the second direction of rotation R2 about the axis 608.

The torque-limited torque application instrument 600 can be configured such that the first minimum torque value is different than the second minimum torque value. For example, the first minimum torque value can be less than the second minimum torque value. In one embodiment, the first minimum torque value can be a minimal value that is close to 0 N-m and the second minimum torque value can be between about 0.01 N-m and about 0.10 N-m, for example 0.05 N-m. In another embodiment, the torque-limited torque application instrument 600 is configured such that the first minimum torque value in the first the first direction of rotation R1 is about 0.02 N-m and the second minimum torque value in the second direction of rotation R2 is about 0.35 N-m.

The values of the first and second minimum torque values of the torque-limited torque application instrument 600 can be adjusted by changing the number of boom arm portions 640 of the ratchet tab 616 and/or by changing the length of the one or more boom arm portions 640. In one example, a higher number of boom arm portions 640 and/or a shorter length of the boom arm portions 640 will increase the first and second minimum torque values, while a lower number of boom arm portions and/or a longer length of the boom arm portions 640 will decrease the first and second minimum torque values. In one embodiment, the torque-limited torque application instrument 600 is configured for use with an embodiment of the distractor 20, 20', 2020, 2020', etc. in which the sufficient torque T and the sufficient torque T' are equal, the first minimum torque value is less than both the sufficient torque T and the sufficient torque T', and the second minimum torque value is greater than both the sufficient torque T and the sufficient torque T'.

Referring to FIGS. 2A-19F, according to one embodiment the bone distraction system 10 can include: 1) a distractor 20; 2) a ratchet 120 configured to be attached to the distractor 20 such that a sufficient torque T is required to actuate the distractor 20 in a first direction of rotation R1 and a sufficient torque T' is required to actuate the distractor 20 in a second direction of rotation R2; 3) a first torque-limited torque application instrument 522 having a selected torque value that is greater than both the sufficient torque T and the sufficient torque T'; and 4) a second torque-limited torque application instrument 522 having a selected torque value that is greater than one of the sufficient torque T and the sufficient torque T' and less than the other of the sufficient torque T and the sufficient torque T'.

According to another embodiment the bone distraction system 10 can include: 1) a distractor 20; 2) a ratchet 120 configured to be attached to the distractor 20 such that a sufficient torque T is required to actuate the distractor 20 in a first direction of rotation R1 and a sufficient torque T' is required to actuate the distractor 20 in a second direction of rotation R2; 3) an instrument 500 configured to apply a torque to the distractor that is greater than both the sufficient torque T and the sufficient torque T'; and 4) a torque-limited torque application instrument 522 having a selected torque value that is greater than one of the sufficient torque T and the sufficient torque T' and less than the other of the sufficient torque T and the sufficient torque T'.

According to another embodiment the bone distraction system 10 can include: 1) at least one distractor 20; 2) at least one ratchet 120 configured to be attached to the at least one distractor 20 such that a sufficient torque T is required to actuate the at least one distractor 20 in a first direction of rotation R1 and a sufficient torque T' is required to actuate the at least one distractor 20 in a second direction of rotation R2; 3) at least one instrument 500. According to one embodiment, the at least one instrument 500 of the bone distraction system 10 described above can further include a first torque-limited torque application instrument 522 having a selected torque value that is greater than both the sufficient torque T and the sufficient torque T'; and a second torque-limited torque application instrument 522 having a selected torque value that is greater than one of the sufficient torque T and the sufficient torque T' and less than the other of the sufficient torque T and the sufficient torque T'. According to another embodiment, the at least one instrument 500 of the bone distraction system 10 can include a standard torque application instrument 502; and a torque-limited torque application instrument 522 having a selected torque value that is greater than one of the sufficient torque T and the sufficient torque T' and less than the other of the sufficient torque T and the sufficient torque T'.

In one embodiment the bone distraction system 10 according to any of the embodiments described herein can further include: a first footplate 320; and a second footplate 420, wherein the first footplate 320 and the second footplate 420 are each configured to be attached to the distractor 20 such that the first footplate 320 and the second footplate 420 define a distance D between them, and actuation of the distractor 20 causes the first footplate 320 to move with respect of the second footplate 420 such that the distance D is adjusted.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the claims.

What is claimed:

1. A method of using a bone distraction system comprising a ratchet and a distractor that includes a distractor body, which supports the ratchet and includes a screw and a sleeve that is connected to the screw, the method comprising:

blocking rotation of the screw, relative to the ratchet about an axis of rotation in a first direction of rotation, with interference between a first surface of the ratchet and the screw until a first torque equal to or greater than a first minimum value is applied to the screw in the first direction of rotation;

applying the first torque to the screw in the first direction of rotation such that the screw rotates relative to the sleeve and the ratchet in the first direction of rotation, thereby causing the screw to cam over the first surface; and blocking rotation of the screw, relative to the ratchet about the axis of rotation in a second direction of rotation that is opposite the first direction of rotation, with interference between a second surface of the ratchet and the screw until a second torque equal to or greater than a second minimum value, is applied to the screw in the second direction of rotation.

2. The method of claim 1, further comprising:
applying the second torque to the screw in the second direction of rotation such that the screw rotates relative to the sleeve and the ratchet in the second direction of rotation, thereby causing the screw to cam over the second surface.

3. The method of claim 1, wherein the first minimum value is about equal to the second minimum value.

4. The method of claim 1, wherein the bone distraction system further comprises an instrument including a handle portion and a tip portion, wherein the instrument is configured such that the instrument defines a maximum value for an output torque, the maximum value being greater than the first minimum value and the second minimum value, and wherein the method further comprises:
engaging the screw with the tip;
receiving an input torque with the handle; and
applying the output torque to the screw.

5. The method of claim 4, wherein the instrument includes a torque limiting mechanism that defines the maximum value for the output torque, and wherein the method further comprises:
inputting an input torque greater than the maximum value to the handle portion such that the torque limiting mechanism prevents the input torque from being transferred to the tip portion.

6. The method of claim 1, wherein the bone distraction system further comprises a first footplate attached to the sleeve and a second footplate attached to the screw, and wherein the method further comprises:
rotating the screw such that the first footplate translates along the axis of rotation relative to the screw and relative to the first footplate.

7. The method of claim 1, further including:
applying the first torque such that the screw rotates relative to the ratchet about the axis of rotation in the first direction of rotation, thereby causing the screw to simultaneously cam over both the first surface and the second surface.

8. The method of claim 1, wherein the first minimum value and the second minimum value are each equal to about 0.05 N-m.

9. The method of claim 1, wherein the step of blocking rotation of the screw, relative to the ratchet about the axis of rotation in the first direction of rotation, further comprises abutting the screw with the first surface of the ratchet so as to prevent rotation of the screw relative to the ratchet about the axis of rotation in the first direction of rotation; and wherein the step of blocking rotation of the screw, relative to the ratchet about the axis of rotation in the second direction of rotation further comprises abutting the screw with the second surface of the ratchet so as to prevent rotation of the screw relative to the screw about the axis of rotation in the second direction of rotation.

10. The method of claim 1, wherein the screw is rotatable at least 360 degrees in the first direction when the first torque is applied, and wherein the screw is rotatable at least 360 degrees in the second direction when the second torque is applied.

11. A method of using a bone distraction system comprising a ratchet and a distractor that includes a distractor body, which supports the ratchet and includes a sleeve and a screw that is positioned partially within the sleeve, the method comprising:
preventing, by engaging the ratchet with the screw, rotation of the screw, relative to the sleeve and the ratchet about an axis of rotation in a first direction of rotation, until a first torque equal to or greater than a first minimum torque value, that is greater than 0 N-m, is applied to the screw in the first direction of rotation;
applying the first torque to the screw in the first direction of rotation such that the screw rotates relative to the sleeve and the ratchet in the first direction of rotation, wherein the screw is rotatable relative to the sleeve in the first direction of rotation only upon application of the first torque in the first direction of rotation; and
preventing, by engaging the ratchet with the screw, rotation of the screw, relative to the sleeve and the ratchet about the axis of rotation in a second direction of rotation that is opposite the first direction of rotation, until a second torque equal to or greater than a second minimum torque value, that is greater than 0 N-m, is applied to the screw in the second direction of rotation, wherein the screw is rotatable relative to the sleeve in the second direction of rotation only upon application of the second torque in the second direction of rotation.

12. The method of claim 11, further comprising:
applying the second torque to the screw in the second direction of rotation such that the screw rotates relative to the sleeve and the ratchet in the second direction of rotation.

13. The method of claim 11, wherein the first minimum torque value is about equal to the second minimum torque value.

14. The method of claim 11, wherein the screw defines a plurality of flats that are angularly spaced about the axis of rotation, the ratchet defines a tip portion that is configured to abut a first one of the plurality of flats, and the method further comprises:
blocking rotation of the screw, relative to the ratchet about the axis of rotation in the first direction of rotation, with interference between the tip portion and flat until the first torque is applied to the screw.

15. The method of claim 11, wherein the ratchet remains translationally fixed relative to the screw with respect to the axis of rotation as the screw rotates relative to the ratchet about the axis of rotation.

16. The method of claim 11, wherein the ratchet comprises a first surface that faces in the first direction of rotation and a second surface that faces in the second direction of rotation, and the method further comprises:
blocking, with interference between the first surface and the second surface, rotation of the screw, relative to the ratchet about the axis of rotation in the first direction of rotation, until the first torque is applied to the screw in the first direction of rotation causing the first surface to cam over the second surface and the screw to rotate relative to the ratchet about the axis of rotation in the first direction of rotation.

17. The method of claim 16, wherein the first surface defines an angle with respect to a radial ray that extends from the axis of rotation in a straight line that is perpendicular to the axis of rotation and passes through the first surface at the angle, and the angle is about 90°.

18. The method of claim 16, wherein the screw comprises a third surface and the ratchet comprises a fourth surface, and the ratchet is configured to be supported by the distractor body such that interference between the third surface, and the method further comprises:
  blocking rotation of the of the screw relative to the ratchet about the axis of rotation in the second direction of rotation until a torque equal to or greater than the second minimum value is applied to the screw in the second direction causing the third surface to cam over the fourth surface and the screw to rotate relative to the ratchet about the axis of rotation in the second direction of rotation.

19. The method of claim 18, wherein the third surface is different than the first surface, and the second surface is different than the fourth surface.

20. The method of claim 19, wherein the screw defines a plurality of flats that are angularly spaced about the axis of rotation, the ratchet defines a tip portion that is configured to abut a first one of the plurality of flats, and the method further comprises:
  blocking rotation of the screw, relative to the ratchet about the axis of rotation in the first direction of rotation, with interference between the tip portion and flat blocks until the first torque is applied to the screw.

21. The method of claim 11, wherein the screw is rotatable at least 360 degrees in the first direction when the first torque is applied, and wherein the screw is rotatable at least 360 degrees in the second direction when the second torque is applied.

22. A method of using a bone distraction system comprising a ratchet and a distractor that includes a distractor body, which supports the ratchet and includes a screw and a sleeve that is connected to the screw, the method comprising:
  blocking rotation of the screw, relative to the ratchet about an axis of rotation in a first direction of rotation, with a first surface of the ratchet until a first torque equal to or greater than a first minimum value is applied to the screw in the first direction of rotation;
  applying the first torque to the screw in the first direction of rotation such that the screw rotates relative to the sleeve and the ratchet in the first direction of rotation, thereby causing the screw to cam over the first surface; and
  blocking rotation of the screw, relative to the ratchet about the axis of rotation in a second direction of rotation that is opposite the first direction of rotation, with a second surface of the ratchet until a second torque equal to or greater than a second minimum value, is applied to the screw in the second direction of rotation;
  wherein causing the screw to cam over the first surface causes the first surface to move relative to the second surface.

23. The method of claim 22, further comprising:
  applying the second torque to the screw in the second direction of rotation such that the screw rotates relative to the sleeve and the ratchet in the second direction of rotation, thereby causing the screw to cam over the second surface.

* * * * *